United States Patent
Hall et al.

(10) Patent No.: US 9,017,659 B2
(45) Date of Patent: *Apr. 28, 2015

(54) PATHOTROPIC TARGETED GENE DELIVERY SYSTEM FOR CANCER AND OTHER DISORDERS

(75) Inventors: Frederick L. Hall, Glendale, CA (US); Erlinda M. Gordon, Glendale, CA (US)

(73) Assignee: Epeius Biotechnologies Corporation, San Marino, CA (US)

( * ) Notice: Subject to any disclaimer, the term of this patent is extended or adjusted under 35 U.S.C. 154(b) by 1094 days.

This patent is subject to a terminal disclaimer.

(21) Appl. No.: 12/446,976

(22) PCT Filed: Nov. 5, 2007

(86) PCT No.: PCT/US2007/023305
§ 371 (c)(1),
(2), (4) Date: Oct. 5, 2009

(87) PCT Pub. No.: WO2008/054826
PCT Pub. Date: May 8, 2008

(65) Prior Publication Data
US 2010/0016413 A1   Jan. 21, 2010

Related U.S. Application Data

(63) Continuation of application No. 11/556,666, filed on Nov. 3, 2006, now abandoned, which is a continuation-in-part of application No. 10/829,926, filed on Apr. 21, 2004, now Pat. No. 8,052,966.

(60) Provisional application No. 60/464,571, filed on Apr. 21, 2003.

(51) Int. Cl.
| *A61K 48/00* | (2006.01) |
| *C12N 15/63* | (2006.01) |
| *C07H 21/04* | (2006.01) |
| *A61K 31/7088* | (2006.01) |
| *A61K 35/76* | (2006.01) |
| *A61K 38/17* | (2006.01) |
| *A61K 38/19* | (2006.01) |
| *A61K 38/45* | (2006.01) |
| *A01K 67/00* | (2006.01) |

(52) U.S. Cl.
CPC ............ *A61K 31/7088* (2013.01); *A61K 35/76* (2013.01); *A61K 38/1709* (2013.01); *A61K 38/193* (2013.01); *A61K 38/45* (2013.01)

(58) Field of Classification Search
USPC ............ 424/93.2; 435/320.1; 536/53.4, 23.4
See application file for complete search history.

(56) References Cited

U.S. PATENT DOCUMENTS

| 4,683,195 | A | 7/1987 | Mullis et al. |
| 4,777,127 | A | 10/1988 | Suni et al. |
| 4,897,355 | A | 1/1990 | Eppstein et al. |
| 5,171,678 | A | 12/1992 | Behr et al. |
| 5,219,740 | A | 6/1993 | Miller et al. |
| 5,279,833 | A | 1/1994 | Rose |
| 5,283,185 | A | 2/1994 | Epand et al. |
| 5,328,470 | A | 7/1994 | Nabel et al. |
| 5,354,674 | A | 10/1994 | Hodgson |
| 5,512,421 | A | 4/1996 | Burns et al. |
| 5,591,624 | A | 1/1997 | Barber et al. |
| 5,643,770 | A | 7/1997 | Mason et al. |
| 5,661,023 | A | 8/1997 | Hrinda et al. |
| 5,670,488 | A | 9/1997 | Gregory et al. |
| 5,681,746 | A | 10/1997 | Bodner et al. |
| 5,705,385 | A | 1/1998 | Bally et al. |
| 5,710,022 | A | 1/1998 | Zhu et al. |
| 5,800,811 | A | 9/1998 | Hall et al. |
| 5,821,234 | A | 10/1998 | Dzau |
| 5,952,225 | A * | 9/1999 | Pensiero et al. ............ 435/352 |
| 5,962,429 | A | 10/1999 | Welsh et al. |
| 5,976,567 | A | 11/1999 | Wheeler et al. |
| 5,980,935 | A | 11/1999 | Kirpotin et al. |
| 5,981,501 | A | 11/1999 | Wheeler et al. |
| 6,004,798 | A | 12/1999 | Anderson et al. |
| 6,096,335 | A | 8/2000 | Thierry |
| 6,110,745 | A | 8/2000 | Zhang et al. |
| 6,120,798 | A | 9/2000 | Allen et al. |
| 6,218,372 | B1 | 4/2001 | Nabel et al. |

(Continued)

FOREIGN PATENT DOCUMENTS

| CA | 2595915 | 8/1998 |
| EP | 0345242 A2 | 6/1988 |

(Continued)

OTHER PUBLICATIONS

Shidong, et al, "Dosimetric and Technical Considerations for Interstitial Adenoviral Gene Therapy as Applied to Prostate Cancer" Int. Journal Radiation Oncology Biol. Phys. 55(1):204-214 (2003).
Anderson, W. Human Gene Therapy. Nature, 1998; 392:25-30.
Arap, et al. Cancer Treatment by Targeted Drug Delively to Tumor Vasculature in a Mouse Model. Science, 1998; 279:377-380.
Asher, et al. Murine Tumor Cells Transduced with the Gene for Tumor Necrosis Factor-α. The Journal of Immunology. 1991; 146:3227-3234.
Behrens, et al. Retroviral gene therapy vectors for prevention of excimer laser-induced corneal haze. Invest Ophthalmol Vis Sci. 2002;43(4):968-77.

(Continued)

*Primary Examiner* — Quang Nguyen
(74) *Attorney, Agent, or Firm* — Wilson Sonsini Goodrich & Rosati

(57) ABSTRACT

Systems for pathotropic (disease-seeking) targeted gene delivery are provided, including viral particles with extremely high titers. In particular, the viral particles are engineered to specifically deliver therapeutic or diagnostic agents to a disease site, such as cancer metastic sites. Personalized dosing regimens are also provided to treat diseases such as cancer efficaciously with reduced adverse side effects.

7 Claims, 40 Drawing Sheets

(56) References Cited

U.S. PATENT DOCUMENTS

| | | | |
|---|---|---|---|
| 6,281,010 | B1 | 8/2001 | Gao et al. |
| 6,669,935 | B1 | 12/2003 | Oldfield et al. |
| 6,818,439 | B1 | 11/2004 | Jolly et al. |
| 7,060,811 | B2 | 6/2006 | Aldaz et al. |
| 7,347,998 | B2 | 3/2008 | Hall et al. |
| 7,708,986 | B2 * | 5/2010 | Gordon et al. ............ 424/93.2 |
| 8,052,966 | B2 * | 11/2011 | Hall et al. ............ 424/93.2 |
| 2002/0173538 | A1 | 11/2002 | Shiao |
| 2002/0177571 | A1 | 11/2002 | Gordon et al. |
| 2003/0027818 | A1 | 2/2003 | Redmond et al. |
| 2004/0253215 | A1 | 12/2004 | Hall et al. |
| 2006/0251627 | A1 | 11/2006 | Gordon |
| 2007/0178066 | A1 | 8/2007 | Hall et al. |
| 2007/0224188 | A1 | 9/2007 | Allan et al. |
| 2007/0225603 | A1 | 9/2007 | Jackson |
| 2008/0119572 | A1 | 5/2008 | Owens et al. |
| 2009/0123428 | A1 | 5/2009 | Hall et al. |
| 2010/0233127 | A1 | 9/2010 | Gordon et al. |

FOREIGN PATENT DOCUMENTS

| | | |
|---|---|---|
| EP | 0334301 B1 | 9/1998 |
| GB | 2200651 A | 8/1988 |
| JP | 2006-524057 | 10/2006 |
| WF | WO93/11230 | 6/1993 |
| WO | WO90/07936 | 7/1990 |
| WO | WO91/02805 | 7/1990 |
| WO | WO93/03769 | 3/1993 |
| WO | WO93/05162 | 3/1993 |
| WO | WO93/10218 | 5/1993 |
| WO | WO93/19191 | 9/1993 |
| WO | WO93/25234 | 12/1993 |
| WO | WO93/25698 | 12/1993 |
| WO | WO94/03622 | 2/1994 |
| WO | WO94/12649 | 6/1994 |
| WO | WO94/28938 | 12/1994 |
| WO | WO95/00655 | 1/1995 |
| WO | WO95/11964 | 5/1995 |
| WO | WO-95/25789 | 9/1995 |
| WO | WO 95/25789 A1 | 9/1995 |
| WO | WO 96/30504 A1 | 10/1996 |
| WO | WO 96/39430 A1 | 12/1996 |
| WO | WO-98-01582 A1 | 1/1998 |
| WO | WO 98/44938 A1 | 10/1998 |
| WO | WO 98/51700 A1 | 11/1998 |
| WO | WO98/58630 | 12/1998 |
| WO | WO01/06574 | 1/2001 |
| WO | WO01/07059 | 2/2001 |
| WO | WO01/31036 | 5/2001 |
| WO | WO01/64870 | 9/2001 |
| WO | WO 01/64870 A2 | 9/2001 |
| WO | WO 01/64870 A3 | 1/2002 |
| WO | WO/02/18572 | 3/2002 |
| WO | WO02/44394 | 6/2002 |
| WO | WO 02/44394 A2 | 6/2002 |
| WO | WO 02/44394 A3 | 2/2003 |
| WO | WO2004/093810 | 11/2004 |
| WO | WO2008/054826 | 5/2008 |

OTHER PUBLICATIONS

Blankenstein, et al. Tumor Suppression after Tumor Cell-targeted Tumor Necrosis Factor α Gene Transfer. The Journal of Experimental Medicine. 1991; 173:1047-1052.

Borrello, et al. A University Granulocyte-Macrophage Colony-Stimulating Factor-Producing Bystander Cell Line for Use in the Formulation of Autologous Tumor Cell-Based Vaccines. Human Gene Therapy. 1999; 10:1983-1991.

Cosset, et al. Retroviral Retargeting by Envelopes Expressing an N-Terminal binding Domain. J Virol. 1995;69:6314-6322.

Cosset, et al. Targeting Retrovirus Entry. Gene Therapy. 1996;3:946-956.

Coze, et al. Characteristics and Immunomodulatory Properties of Human Neuroblastoma Cells after Retrovirus-Mediated Transfer of the Cytokine Genes IL-2 and IFN-γ, Transgenics. 1995; 1:585-595.

Dang et al. Gene therapy and translational cancer research. Clin. Cancer Res. 1999; 5:471-474.

Dranoff, et al. Vaccination with irridiated tumor cells engineered to secrete murine granulocyte-macrophage colony-stimulating factor stimulates potent, specific, and long-lasting anti-tumor immunity, Proceedings of the National Academy of Sciences, 1993; 90:3539-3543.

El Kamar, et al. Metastatic Pancreatic Cancer: Emerging Strategies in Chemotherapy and Palliative Care. The Oncologist. 2003; 8:18-34.

Fearon, et al. Interleukin-2 Production by Tumor Cells Bypasses T Helper Function in the Generation of an Antitumor Response. Cell. 1990; 60:397-403.

Fong, et al. The Use and Development of Retroviral Vectors to Deliver Cytokine Genes for Cancer Therapy. Critical Reviews in Therapeutic Drug Carrier Systems. 2000; 17:1-60.

Foreman, et al. Mechanisms of selective killing of neuroblastoma cells by natural killer cells and lymphokine activated killer cells. Potential for residual disease eradication. British Journal of Cancer. 1993; 67:933-938.

Gansbacher, et al. Retroviral lymphokine gene transfer induced secretion of Interleukin-2 (IL-2) or Interferon-gamma (IFN-γ) by human melanoma cells. Eighty-Second annual meeting of the American Association for Cancer Research Proceedings, Houston, Texas. 1991;32:1514.

Gardlik, et al. Vectors and delivery systems in gene therapy. Med. Sci. Monit. 2005; 11:RA110-121.

Gilboa. Immunotherapy of Cancer with Genetically Modified Tumor Vaccines. Seminars in Oncology. 1996; 23:101-107.

Gulombek. Treatment of Established Renal Cancer by Tumor Cells Enginneered to Secrete Interleukin-4. Sciences. 1991;254:713-716.

Goncalves, M. A concise peer into the background, initial thoughts and practices of human gene therapy. BioEssays. 2005; 27:506-517.

Gordon, et al. Capture and expansion of bone marrow-derived mesenchymal progenitor cells with a transforming growth factor-β1-von Willebrand's factor fusion protein for retrovirus-mediated delivery of coagulation factor IX. Human Gene Therapy. 1997; 8:1385-1394.

Gordon, et al. First clinical experience using a 'pathotropic' injectable retroviral vector (Rexin-G) as intervention for stage IV pancreatic cancer. Int J Oncol. 2004;24(1):177-85.

Gordon, et al. Genetic Engineering of Targeted Retroviral Vectors. Vector Targeting Strategies for Therapeutic Gene Delivery. 2002; 293-320.

Gordon, et al. Inhibition of Metastic Tumor Growth in Nude Mice by Portal Vein Infusions of Matrix-targeted Retroviral Vectors Bearing a Cytocidal Cyclin G1 Construct. Cancern Research. 2000; 60:3343-3347.

Gordon, et al. Le morte du tumour: histological features of tumor destruction in chemo-resistant cancers following intravenous infusions of pathotropic nanoparticles bearing therapeutic genes. Int J Oncol. 2007; 30(6):1297-307.

Gordon, et al. Lesion-targeted injectable vectors for vascular restenosis. Hum Gene Ther. 2001;12(10):1277-87.

Gordon, et al. Pathotropic nanoparticles for cancer gene therapy Rexin-G IV: three-year clinical experience, Int J Oncol. 2006; 29(5):1053-64.

Gordon, et al. Systemic Administration of a Matrix-Targeted Retroviral Vector is Efficacious for Cancer Gene Therapy in Mice. Human Gene Therapy, 2001; 12:193-204.

Guinan, et al. Pivotal Role of the B7:CD28 Pathway in Transplantation Tolerance and Tumor Immunity. Blood. 1994; 84:3261-3282.

Hall, et al. Design, expression, and renaturation of a lesion-targeted recombinant epidermal growth factor-von Willebrand factor fusion protein: efficacy in an animal model of experimental colitis. *Int J Mol Med*. Dec. 2000;6(6):635-43.

Hall, et al. Molecular Engineering of Matrix-Targeting Retroviral Incorporating a Surveilance Function Inherent in von Willebrand Factor. Human Gene Therapy. 2000; 11:983-993.

Hall, et al. Targeting Retroviral Vectors to Vascular Lesions by Genetic Engineering of the MoMuIV gp70 Envelope Protein. Human Gene Therapy. 1997;8:2183-2192.

(56) References Cited

OTHER PUBLICATIONS

Handgretinger, et al. Interferon-Gamma Upregulates the Susceptibility of Human Neuroblastoma Cells to Interleukin-2-Activated Natural Killer Cells. Natural Immunity and Cell Growth Regulation. 1989; 8:189-196.
Hock, et al. Interleukin 7 Induces CD4+T Cell-dependent Tumor Rejection. The Journal of Experimental Medicine. 1991; 174:1291-1298.
Hu, et al. Design of Retroviral Vectors and Helper Cells for Gene Therapy. Pharmacology Reviews. 2000; 52:493-511.
Jaffee. Immunotherapy of Cancer. Annals of The New York Academy of Sciences. 886:67-72.
James, et al. Measuring response in solid tumors: unidimensional versus bidimensional measurement. J Natl Cancer Inst. Mar. 17, 1999;91(6):523-528.
Kasahara, et al. Tissue-Specific Targeting of Retroviral Vectors Through Ligand-Receptor interactions. Science. 1994; 266:1373-1376.
Kay, et al. Evidence for gene transfer and expression of factor IX in Hemophillia B Patients. Nature Genetics. 2000, 24:257-261.
Kim, et al. Macrophage Colony-Stimulating Factor Can Modulate Immune Responces and Attract Dendritic Cells in Vivo. Human Gene Therapy. 2000; 11:305-321.
Klagsbrun, et al. Regulators of Angiogenesis. Annual Review of Physiology. 1991; 53:217-239.
Knobloch, et al. T cell receptor diversity in severe combined immunodeficiency following HLA-haploidentical bone marrow transplantation. Bone Marrow Transplantation. 1991; 8:383-387.
Kotani, et al. Improved Methods of Retroviral Vector Transduction and production for Gene Therapy. Human Gene Therapy. 1994; 5:19-28.
Kurane, et al. Ctyokines as an Adjuvant to Tumor Vaccines: Efficacy of Local Methods of Delivery. Annals of Surgical Oncology. 1997: 4:579-585.
Kuvshinoff, et al. Treatment of Respectable and Locally Advanced Pancreatic Cancer. Cancer Control. 2000; 7:428-436.
Langreth, et al. Researchers get dose of reality as logistics stymie gene therapy. The Wall Street Journal. Oct. 27, 1999 (5 pages).
Lenz, et al. Tumor Site-Specific Phase I Evaluation of Safety of Hepatic Arterial Infusion of a matrix-Targeted Retroviral Vector Bearing a Dominant Negative Cyclin G1 Construct as Intervention for Colorectal Carcinoma Metastic to the Liver. Human Gene Therapy. 2002; 13:1515-1537.
Lieberman, et al. Innovative Treaatments for Pancreatic Cancer. Surg Clin North Am. 2001; 81:715-739.
Liu, et al. Incorporation of Tumor Vasculature Targeting Motifs into Moloney Murine Leukemia Virus Env Escort Protiens Enhances Retrovirus Binding and Transduction of Human Endothelial Cells. Journal of Virology. 2000; 74:5320-5328.
Mackensen, et al. Immunostimulatory Cytokines in Somatic Cells and Gene Therapy of Cancer. Cytokine and Growth Factor Reviews. 1997; 8:119-128.
Magovern, et al. Regional Angiogenesis Induced in Nonischemic Tissue by an Adenoviral Vector Expressing Vascular Endothelial Growth Factor. Human Gene Therapy. 1997; 8:215-227.
Main, et al. Human Neuroblastoma Cell Lines are Susceptible to Lysis by Natural Killer Cells but Not by Cytotoxic T Lymphocytes. The Journal of Immunology, 1985; 135:242-246.
Marin, et al. Targeted Infection of Human Cells via Major Histocompatibility Complex Class 1 Molecules by Moloney Murine Leukemia Virus-Derived Viruses Displaying Single-Chain Antibody Fragment-Envelope Fusion Proteins. Journal of Virology. 1996; 70:2957-2962.
Martin, et al. Retroviral Vector Targeting to Melanoma Cells by Single-Chain Antibody Incorporation in Envelope, Human Gene Therapy. 1998; 9:737-746.
Masood, et al. Retroviral Vectors Bearing IgG-binding Motifs for Antibody-Mediated Targeting of Vascular Endothelial Growth Factor Receptor. Int'l J Mol Med. 2001: 8:335-343.
Mellstedt, et al. Augmentation of the Immune response with granulocyte-macrophage colony-stimulating factor and other hematopoietic growth factors. Current Opinions in Hematology. 1999; 6:169-175.
Mendiratta, et al. Combination of Interleukin 12 and interferon α Gene therapy Induces a Synergistic Antitumor Response against Colon and Renal Cell Carcinoma. Human Gene Therapy. 2000; 11:1851-1862.
Miller, et al. Improved Retroviral Vectors for Gene Transfer and Expression. Biotechniques. 1989; 7:984-990.
Miller, et al. Intratumoral Administration of Adenoviral Interleukin 7 Gene-Modified Dendritic Cells Augments Specific Antitumor Immunity and Achieves Tumor Eradication. Human Gene Therapy. 2000; 11:53-65.
Morgan, et al. Analysis of the Functional and Host Range-Determining Regions of the Murine Ecotropic and Amphotropic Retrovirus Envelope Proteins. Journal of Virology. 1993; 67:4712-4721.
Nabel, et al. Direct Gene Transfer with DNA-liposome complexes in melanoma: Expression, biologic activity, and lack of toxicisity in humans. Proceedings of the National Academy of Sciences. 1993; 90:11307-11311.
Nagai, et al. Irradiated tumor cells adenovirally engineered to secrete granculocyte/macrophage-colony-stimulating factor establish antitumor immunity and eliminate pre-existing tumors in syngeneic mice. Cancer Immunology Immunotherapy. 1998; 47:72-80.
Neda, et al. Chemical Modification of an Ecotropic Murine Leukemia Virus Results in Redirection of Its Target Cell Specificity. The Journal of Biological Chemistry. 1991; 266:14143-14146.
Nishi, et al. Collagen-binding growth factors: Production and characterization of functional fusion proteins having a collagen-binding domain. Proc. Natl. Acad. Sci. USA. 1998; 95:7018-7023.
Office Action Dated Apr. 7, 2009 issued in U.S. Appl. No. 12/016,847.
Ohno, et al. Cell Specific Targeting of Sindbis Virus Vectors Displaying IgG-binding domains of Protein. A. Nat Biotechnol. 1997; 15:763-767.
O'Reilly, et al. Endostatin: An Endogenous Inhibitor of Angiogenesis and Tumor Growth. Cell. 1997; 88:277-285.
Peng, et al. Viral Vector Targeting. Curr Opin Biotechnol. 1999; 454-457.
Romano, et al. Latest Developments in gene transfer technology. Achievements, perspectives, and controversies over therapeutic applications. Stem Cells. 2000; 18:19-39.
Rosemurgy, et al. New Directions in Systemic Therapy of Pancreatic Cancer. Cancer Control. 2000; 7:437-444.
Rosenberg, et al. Gene Transfer into Human-Immunotherapy of Patients With Advanced Melanoma, Using Tumor Infiltrating Lymphocytes Modified By Retroviral Gene Transduction. New England Journal of Medicine. 1990; 323:570-578.
Rosenberg, S. Immunization of Cancer Patients Using Autologous Cancer Cells Modified by Insertion of the Gene for InterLeukin2. Human Gene Therapy. 1992; 3:75-90.
Russell, S. Retroviral Vectors Displaying Functional Antibody Fragments. Nucl Acid Res. 1993; 21:1081-1085.
Sadler, et al. Cloning and Characterization of two cDNAs coding for human von Willebrand factor. Natl. Acad. Sci. USA. 1985; 82:6394-6398.
Skotzko, et al. Retroviral Vector-mediated Gene Transfer of Antisense Cyclin G1 (CYCG1) Inhibits Proliferation of Human Osteogenic Sarcoma Cells. Cancer Research. 1995; 55:5493-5498.
Somia, et al. Generation of Targeted Retroviral Vectors by Using Single-Chain Variable Fragment: An Approach to In Vivo Gene Delivery. Proc Natl Acad Sci USA. 1995; 92:7570-7574.
Soneoka, et al. A transient three-plasmid expression system for the production of high titer retroviral vectors. Nucleic Acids Research. 1995; 23:628-633.
Song, et al. Phase I/II evaluation of safety and efficacy of a matrix-targeted retroviral vector bearing a dominant negative cyclin G1 construct (Md-dnG1) as adjunctive intervention for superficial corneal opacity/corneal scarring; Hum Gene Ther. 2003;14(3):306-9.
Stromblad, et al. Cell Adhesion and Angiogenesis. Trends Cell, Biol. 1996;64:462-467.

(56) References Cited

OTHER PUBLICATIONS

Suh, et al. Treatment of Liver Metastases form Colon Carcinoma with Autologous Tumor Vaccines Expressing Granulocyte-Macrophage Colony-stimulating Factor. Journal of Surgical Oncology. 1999; 72:218-224.
Takagi, et al. A Collagen/Gelatin-Binding Decapeptide Derived from Bovine Propolypeptide of von Willebrand Factor. Biochemistry. 1992; 31:8530-8534.
Takagi, et al. Collagen-Binding Domain Within Bovine Propolypeptide of Von Willebrand Factor. J. Biol Chem. 1991; 266:5575-5579.
Tepper, et al. Experimental and Clinical Studies of Cytokine Gene-Modified Tumor Cells. Human Gene Therapy. 1994; 5:153-164.
Tseng, et al. Gene Therapy for Pancreatic Cancer. Surg Oncol Clin N. Am. 2002; 11:537-569.
Ucar, et al. Sustained cytokine production and immunophenotype changes in human neuroblastoma cell lines transduced with a human gamma interferon vector. Cancer Gene Therapy. 1995; 2:171-181.
Valsesia-Wittman, et al. Modification in the Binding Domain of Avian Retrovirus Envelope Protein to Redirect the Host Range of Retroviral Vectors. Journal of Virology. 1994; 68:4609-4619.
Van Riel, et al. Pancreaticobiliary Cancer: The Future Aspects of Medical Oncology. Ann Oncol. 1999; 10:296-299.
Verma, et al. Gene Therapy: Promices, Problems and Prospects. Nature. 1997; 389:239-242.
Verma, et al. Gene Therapy: Twenty-first century medicine. Annu. Rev. Biochem. 2005; 74:711-738.
Warren, et al. Uses of Granulocyte-macrophage colony-stimulating factor in vaccine development. Current Opinion in Hematology. 2000, 7:168-173.
Watanabe, et al. Exogenous expression of mouse interferon γ cDNA in mouse neuroblastome C1300 cells results in reduced tumorigenicity by augmented anti-tumor immunity. Proceedings of the National Academy of Sciences. 1989; 86:9456-9459.
Wu, et al. Characterization of the Proline-Rich Region of Murine Leukemia Virus Envelope Protein. Journal of Virology. 1998; 72:5383-5391.
Wu, et al. Molecular Cloning of the Human CYCG1 Gene Encoding a G-Type Cyclin: Overexpression in Human Osteosarcoma Cells. Oncology Reports. 1994; 1:705-711.
Xie, et al. Elements within the First 17 Amino Acids of Human Osteonectin are Responsible for Binding to Type V Collagen. The Journal of Biological Chemistry. 1996; 271:8121-8125.
Xu, et al. Long Term Inhibition of Neointima Formation in Balloon-Injured Rat Arteriesby Intraluminal Instillation of a Matrix-Targeted Retroviral Vector Bearing an Improved Cytocidal Cyclin G1 Construct. Intl J Mol Med. 2001; 8:19-30.
Yang, et al. Development of Novel Cell Surface CD34-Targeted Recombinant Adenoassociated Virus Vector for Gene Therapy. Human gene Therapy. 1998; 9:1929-1937.
Yang, et al. Generation of Retroviral Vector for Clinical Studies using Transient Transfection. Human Gene Therapy. 1999; 10:123-132.
Zhao, et al. Identification of the Block in Targeted Retroviral-Mediated Gene Transfer. Proc National Academy of Science USA. 1999; 96:405-4010.
Zwiebel, J. Cancer Gene and Oncolytic Virus Therapy. Semin Oncol. 2001; 28:336-343.
Arnold et al. "Molecular Pathogenesis of Colorectal Cancer," Cancer 104:2035-2047 (2005).
Huang et al., "The structural and mechanical complexity of cell-growth control," Nature Cell Biol 1:E131-E138 (1999).
Lenz et al., "Tumor site-specific phase I/II evaluation of the safety and efficacy of hepatic atrerial infusion of a matrix-targeted retroviral vector bearing a dominant negative cyclin G1 (dnG1) construct as treatment for colorectal carcinoma metastatic to liver," Human Gene Therapy 12:1563-1565 (2001).
Liberman et al., "Breast cancer cancer diagnosis by scintimammography: a meta-analysis and review of the literature," Breast Cancer Research and Treatment 80:115-126 (2003).
Lowenfels et al., "Epidemiology and Prevention of Pancreatic Cancer," Jpn J Clin Oncol 34(5):238-244 (2004).
Nagano et al., "Gene therapy eradicating distant disseminated micrometastases by optimal ctyokine expression in the primary lesion only: novel concepts for successful cytokine gene therapy," Intl J Onc 24:549-558 (2004).
Therasse et al., "New Guidlines to evaluate the response to treatment in solid tumors," J Natl Cancer Inst 92:205-216 (2000).
Pan and Whitley, "Closed hollow-fiber bioreactor: a new approach to retroviral vector production," J. Gene Med. 1(6):433-440 (1999).
Reeves and Cornetta, "Clinical retroviral vector production: step filtration using clinically approved filters improves titers," Gene Therapy 7:1993-1998 (2000).
Baum et al, "Side effects of retroviral gene transfer into hematopoietic stem cells," Blood 101:2099-2144 (2003).
Hacien-Bey-Abina et al., "LMO2-Associated Clonal T Cell Proliferation in Two Patients after Gene Therapy for SCID-X1," Science 302:415-419 (2003).
Kustikova et al., "Dose finding with retroviral vectors: correlation of retroviral vector copy numbers in single cells with gene transfer efficiency in cell population," Blood 102:3934-3937 (2003).
Diehl et al., "A Dominant-Negative Cyclin D1 Mutant Prevents Nuclear Import of Cyclin-Dependent Kinase 4 (CDK4) and its Phosphorylation by CDK-Activating Kinase," Mol. Cell Biol. 17(12):7362-7374 (1997).
Geddis et al., "Thrombopoietin: a pan-hematopoietic cytokine," Cytokine & Growth Factor Reviews 13:61-67 (2002).
Ghezzi et al., "Erythropoietin as an antiapoptotic, tissue-protective cytokine," Cell Death & Differentiation 11:537-544 (2004).
Hinds et al., "Function of human cyclin gene as an oncogene,"PNAS USA 91:709-712 (1994).
Addison et al., "Comparison of the human versus murine cytomegalovirus immediate early gene promoters for transgene expression by adenoviral vectors," J. Gen. Virol. 78:1653-1661 (1997).
Chen et al., "Combination suicide and cytokine gene therapy for hepatic metastases of colon carcinoma: Sustained antitumor immunity prolongs animal survival," Cancer Res. 46:3758-3762 (1996).
Kafri et al., "Sustained expression of genes delivered directly into liver and muscle by lentiviral vectors," Nature Genetics 17:314-317 (1997).
Rousculp et al., "Quantitative evaluation of retroviral gene transduction efficiency in human lung cancer cells," Human Gene Therapy 3:471-477 (1992).
Benedetti et al, Limited Efficacy of the HSV-TK/GCV System for Gene Therapy of Malignant Gliomas and Perspectives for the Combined Transduction of the Interleukin-4 Gene, Human Gene Therapy, 8:1345-1353 (1997).
Brockstedt et al. Development of Anti-tumor Immunity against a Non-immunogenic Mammary Carcinoma through in Vivo Somatic GM-CSF, IL-2, and HSVtk Combination Gene Therapy. Molecular Therapy 6, 627-636 (2002).
Fields-Berry et al., A recombinant retrovirus encoding alkine phosphatase confirms clonal boundary assignment in lineage analysis of murine retina, PNAS, 89:693-697 (1992).
Gordon et al. (2000). Inhibition of metastatic tumor growth in nude by portal vein infusions of matrix-targeted retroviral vectors bearing a cytocidal cyclin G1 construct. Cancer Res. 60(13)3343-3347.
Hacein-Bey-Abina et al., "A Serious Adverse Event after Successful Gene Therapy for X-Linked Severe Combined Immunodefiency," N Engl J Med 348(3):255 (2003).
Lode et al. Targeted GMCSF therapy suppress metastases of murine neuroblastoma mediated by macrophages. Blood. 1998; 92(10) Suppl. 1: p. 19a (Abstract # 67).
Parekh-Olmedo et al. Gene Therapy progerss and prospects: targeted gene repair. Gene Ther. Apr. 2005;12(8)639-46.
Blackwell., et al, "Retargeting to EGFR enhances adenovirus infection efficiency of squamous cell carcinoma." *Arch Otolaryngol Head Neck Surg.*, Aug. 1999;(8):856-63.
Check, E., "A tragic setback," 2002, *Nature* 420:116-118.
Chu, et al, "Toward highly efficient cell-type-specific gene transfer with retroviral vectors displaying single-chain antibodies." *J Virol.* Jan. 1997;7(1):720-5.

(56) References Cited

OTHER PUBLICATIONS

Cripps, et al. "Phase II randomized study of ISIS 3521 and ISIS 5132 in patients with locally advanced of metastatic colorectal cancer: a National Cancer Institute of Canada clinical trails group study." *Clinical Cancer Research*. 2002; 8:2188-2192.
Drapkin, et al, "Targeting the urokinase plasminogen activator receptor enhances gene transfer to human airway epithelia."*J Clin Invest*. Mar. 2000;105(5):589-96.
Galanis et al., "Phase 1 Trial of a Pathotropic Retrovial Vector Expressing a Cytocidal Cyclin G1 Construct (Rexin-G) in Patients With Advanced Pancreatic Cancer," 2008 *Mol Ther* 16(5):979-984.
Goldman, et al, "Targeted gene delivery to Kaposi's sarcoma cells via the fibroblast growth factor receptor." *Cancer Res*. Apr. 15, 1997;57(8):1447-51.
Han, et al. "Ligand-directed retroviral targeting of human breast cancer cells." *Proc Natl Acad Sci U S A*. Oct. 10, 1995;92(21):9747-51.
Jones, et al. "Antibodies for targeted gene therapy: extracellular gene targeting and intracellular expression." *Advanced Drug Delivery Reviews*. 1998:31:153-170.
Kasono, et al. "Selective Gene Delivery to head and neck cancer cells via an integrin targeted adenoviral vector." *Clin Cancer Res*. Sep. 1999;5(9):2571-9.
Majumdar et al. "Efficacy of herpes simplex virus thymidine kinase combination with cytokine gene therapy in experimental metastatic breast cancer model." *Cancer Gene Ther*., 2000, 7(7):1086-99.
Marshall, et al. "A phase II trial of ISIS 3521 in patients with metastatic colorectal cancer," *Clinical Colorectal Cancer*. 2004; 4:268-274.
McDonald, et al. "Efficient adenoviral gene transfer to kidney cortical vasculature utilizing a fiber modified vector." *J Gene Med*. Mar.-Apr. 1999;(2):103-10 (Abstract Only).
Nicklin, et al. "Selective targeting of gene transfer to vascular endothelial cells by use of peptides isolated by phage display," *Circulation*. Jul. 11, 2000;102(2):231-7.
Ohno, et al. "Retrovirus vectors displaying the IgG-binding domain of protein A." *Biochem Mol Med*. Oct. 1997;62(1):123-7.
OZA, et al. "Phase II Study of CGP 69846A (ISIS 5132) in recurrent epithelial ovarian cancer: an NCIC clinical trails group study (NCIC IND.116)." *Gynecological Oncology*. 2003:89-129-133.
Palu et al. "Gene therapy of glioblastoma multiforme via combined expression of suicide and cytokine genes: a pilot study in humans." *Gene Therapy*, 1999,6: 330-337.
Printz, et al. "Fibroblast growth factor 2-retargeted adenoviral vectors exhibit a modified biolocalization pattern and display reduced toxicity relative to native adenoviral vectors." *Hum Gene Ther*. Jan. 1, 2000;11(1):191-204 (Abstract only).
Rancourt, et al, "Basic fibroblast growth factor enhancement of adenovirus-mediated delivery of the herpes simplex virus thymidine kinase gene results in augmented therapeutic benefit in a murine model of ovarian cancer." *Clin Cancer Res*. Oct. 1998;4(10);2455-61.
Reynolds, et al. "A targetable, injectable adenoviral vector for selective gene delivery to pulmonary endothelium in vivo." *Mol Ther*. Dec. 2000;2(6):562-78.
Romanczuk, et al. "Modification of an adenoviral vector with biologically selected peptides: a novel strategy for gene delivery to cells of choice." *Hum Gene Ther*. Nov. 1, 1999;10(16):2615-26. (Abstract only).
Tolcher, et al. "A randomized phase II and pharmacokinetic study of the antisense oligonucleotides ISIS 3521 and ISIS 5132 in patients with hormone-refractory prostate cancer." *Clinical Cancer Research*. 2002;8:2530-2535.
Tortora and Derrickson. *Principles of Anatomy and Physiology*, 2006, 11th ed. pp. 99-100 and 689-690. Wiley.
Transfiguracion, J. et al. "Size-Exclusion Cromatography Purification of High-Titer Vesicular Stomatitis Virus G Glycoprotein-Pseudotyped Tetrovectors for Cell and Gene Therapy Applications," *Human Gene Therapy*, Aug. 2003, 14: 1139-1153.

Van Beusechem, et al. "Efficient and selective gene transfer into primary human brain tumors by using single-chain antibody-targeted adenoviral vectors with native tropism abolished." *J Virol*. Mar. 2002;76(6):2753-62.
Vanderkwaak, et al. "An advanced generation of adenoviral vectors selectively enhances gene transfer for ovarian cancer gene therapy approaches."*Gynecol Oncol*. Aug. 1999:74(2):227-34. (Abstract only).
Wickham, et al. "Targeting endothelium for gene therapy via receptors up-regulated during angiogenesis and inflammation." *Cancer Immunol Immunother*, Nov.-Dec. 1997;45(3-4):149-51. (Abstract only).
Williams, et al. "Identification of a novel cyclin-like protein in human tumor cells," *Journal of Biological Chemistry*. 1993; 268:8871-8880.
Abeloff, M., Ed. "New endpoints needed in targeted Rx trials." (2006) Oncol. News Intl'l. 15:2,16.
Apperly et al., "Retroviral gene transfer of human adenosine deaminase in murine hematopoietic cells: effect of selectable marker sequences on long-term expression." Blood 78:310-317 (1991).
Armentano et al., "Expression of human factor IX in rabbit hepatocytes by retrovirus-mediated gene transfer: potential for gene therapy of hemophilia B." Proc. Natl. Acad. Sci. USA 87:6141-6145.
Behr, J. "Gene Transfer with synthetic cationic amphiphiles: prospects for gene therapy." Bioconjugate Chemistry. 5:382-389 (1994).
Belmont et al. "Expression of human adenosine deaminase in murine hematopoietic cells." Molec. and Cell Biol. 8(12):5116-5125 (1988).
Black et al. "Herpes simplex virus-1 thymidine kinase mutants created by semi-random sequence mutagenesis improve prodrug-mediated tumor cell killing." Cancer Res. 2001. 61:3022-3026.
Burris, H., et al, "Improvements in survival and clinical benefit with gemcitabine as first-line therapy for patients with with advanced pancreas cancer: a randomized trial." (1997) J. Clin. Oncol. 15:2403-2413.
Chu et al. "SV40 DNA transfection of cells in suspension: analysis of efficiency of transcription and translation of T-antigen." Gene 13:197-202 (1981).
Comitttee for medicinal products for human use (CHMTP): "Guidline on development and manufacture of lemtivar vectors", European Medicines Agency (EMEA), May 26, 2005, pp. 1/8-8/8, XP002636697, London, Retrieved from the Internet: URL: http:www.ema.europa.eu/docs/en_GB/document_library/Scientific_guideline/2009/10/WC500003984.pdf.
Culver et al. "In vivo gene transfer with retroviral vector-producer cells for treatmment of experimental brain tumors."(1992) Science 256, 1550-1552.
Curiel, D. et al., "High-efficiency gene transfer mediated by adenovirus coupled to DNA-polylysine complexes." Hum. Gene Ther. (1992) 3:147-154.
Dhawan et al., "Systemic delivery of human growth hormone by injection of genetically engineered myoblasts." Science 254:1509-1512 (1991).
Dranoff, G., "GM-CSF-based cancer vaccines." Immunol. Rev 188:147-154, 2002.
Eager R. and Nemunaitis J: "GM-CSF gene-transduced tumor vaccines." Molec Ther 12:18-27, 2005.
Fasbender et al. "Complexes of adenovirus with polycationic polymers and cationic lipids increase the efficiency of gene transfer in vitro and in vivo." J. Biol. Chem. 272:6479-6489.
Fornier and Norton, "Dose-dense adjuvant chemotherapy for primary breast cancer." (2005) Breast Cancer Res. 7:64-69.
Furlan, M. "Sticky and promiscuous plasma protiens maintain the equilibrium between bleeding and thrombosis." Swiss Med. Wkly 132(15-16):181-189 (2002).
Geddis et al., "Thrombopoietin: a pan-hematopoietic cytokine," Cytokine & Growth Factor Reviews 13:61-73 (2002).
Ghezzi et al., "Erythropoietin as an antiapoptotic, tissue-protective cytokine." Cell Death & Differentiation 11:S37-S44 (2004).
Graham, F. et al. "A new technique for the assay of infectivity of human adenovirus 5 DNA." Virology 52(2):456-467 (1973).
Halbert, C. et al. "Prevalence of neutralizing antibodies against adeno-associated virus (AAV) types 2, 5, and 6 in cystic fibrosis and normal populations: Implications for gene therapy using AAV vectors." (2006) Hum. Gene Ther. 17(4): 440-447.

(56) References Cited

OTHER PUBLICATIONS

Hawley-Nelson, P. et al. "LipofectAMINE reagent: a new, higher efficiency polycationic liposome transfection reagent." Focus 15(3):73-79 (1993).

Heitjan, D. "Generalized Norton-Simon models of tumor growth." (1991) Stat. Med. 10:1075-1088.

Hodgson and Solaiman, "Virosomes: cationic liposomes enhance retroviral transduction." Nature Biotechnology 14:339-342 (1996).

Jellinek, D. et al. "Potent 2'-amino-2'-deoxypyramidine RNA inhibitors of basic fibroblast growth factor." (1995) Biochemistry 34:11363-11372.

Khalighinejad, N. et al., "Adenoviral gene therapy in gastric cancer: a review." World Gastroenterol, 2008, 14:180-184.

Lazo, P., et al. "Splice acceptor site for the env message of Moloney murine leukemia virus." (1987) J. Virol 61(6): 2038-2041.

Leventis, R., et al., "Interactions of mammalian cells with lipid dispersions containing novel metabolizable cationic amphiphiles." Biochem. Biophys. Acta 1023:124-132 (1990).

Lin Y., et al., "Modified RNA sequence pools for in vitro selecion." (1994) Nucl. Acids Res. 22(24):5229-5234.

Markowitz, D., et al., "A safe packaging line for gene transfer: separating viral genes on two different plasmids." Journal of Virology 62(4):1120-1124, 1988.

Morecksi, S., et al., "Retrovirus-mediated gene transfer into CD4+ and CD8+ human T cell subsets derived from tumor-infiltrating lymphocytes and peripheral blood mononuclear cells." Cancer Immunol. Immunother,32:342-352 (1991).

Nicolaou, K.C., et al. "Calicheamicin $\Theta'_1$: a rationally designed molecule with extremely potent and selective DNA cleaving properties and apoptosis inducing activity," Angew. Chem. Intl. Ed. Engl., 33:183-186 (1994).

Nilsson, R., et al., "Extracorporeal immunoadsorption therapy on rats. In vivo depletion of specific antibodies." (1990) Clin. Exp. Immunol. 82(3)440-444.

Norton, L. "Conceptual and practical implications of breast tissue geometry: toward a more effective, less toxic therapy." (2005) Oncologist 10:370-381.

Norton, L. "Use of dose-dense chemotherapy in the management of breast cancer," (2006) Clin Adv Hematol Oncol. 4:36-37.

Pagratis, N., et al., "Potent 2'-amino-, and 2'-flouro-2'-deoxyribonucleotide RNA inhibitors of keratinocyte growth factor." (1997) Nature Biotechnol. 15:68-73.

Pear, W., et al., "Production of high-titer helper-free retroviruses by transient transfection." 1993, Proc. Natl. Acad. Sci. 90:8392-8396.

Pollack, A., "F.D.A. Halts 27 Gene Therapy Trials After Illness," The New York Times, Jan. 15, 2003; URL: http://www.nytimes.com/2003/01/15/us/fda-halts-27-gene-therapy-trials-after-illness.html.

Potter, M., et al., "Review—the use of immunosupressive agents to prevent neutralizing antibodies against a transgene product." (1999) Ann. N.Y. Acad. Sci. 875:159-174.

Puyal, C., et al., "A new cationic liposome encapsulating genetic material. A potential delivery system for polynucleotides." Eur. J. Biochem. 228(3):697-703 (1995).

Gordon E., et al., "Rexin-G, a targeted genetic medicine for cancer." Expert Opin Biol Ther. May 2010;10(5):819-832.

Stamatatos, L., et al., "Interactions of cationic lipid vesicles with negatively charged phospholipid vesicles and biological membranes." Biochemistry 27:3917-3925 (1998).

Yao, S., et al., "Expression of human factor IX in rat capillary endothelial cells: toward somatic gene therapy for hemophilia B." Proc. Natl. Acad. Sci. USA 88:8101-8105 (1991).

\* cited by examiner

Figure 1
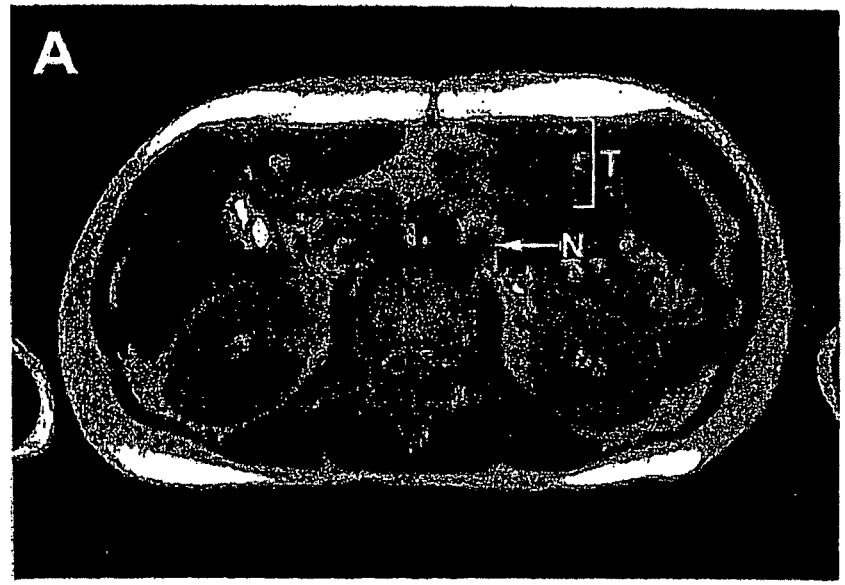
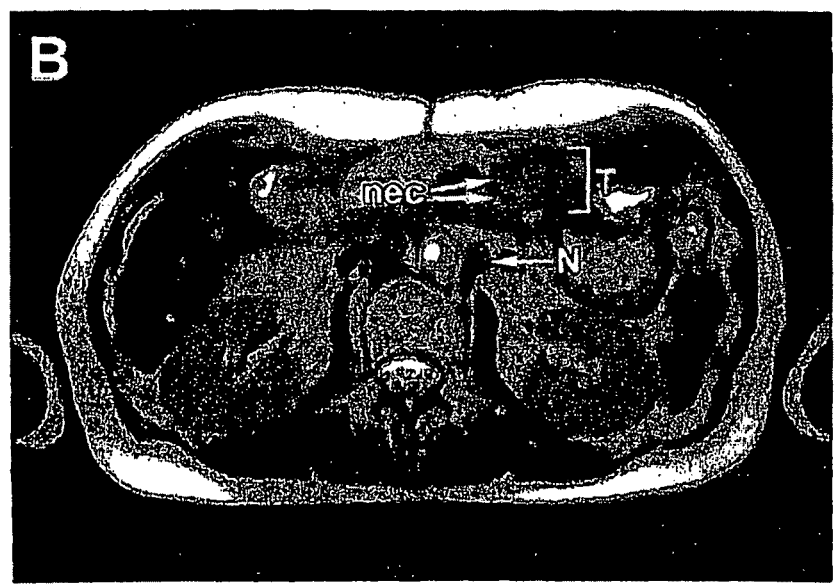

Figure 2
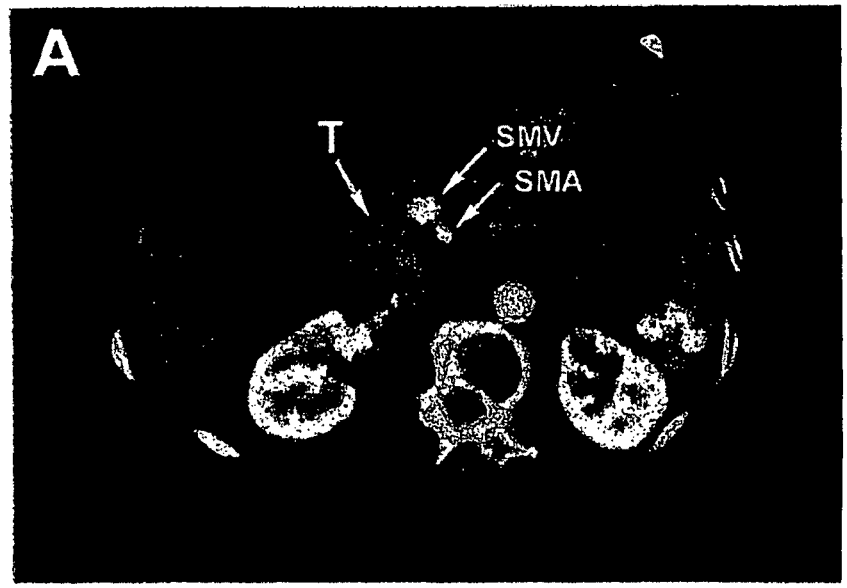
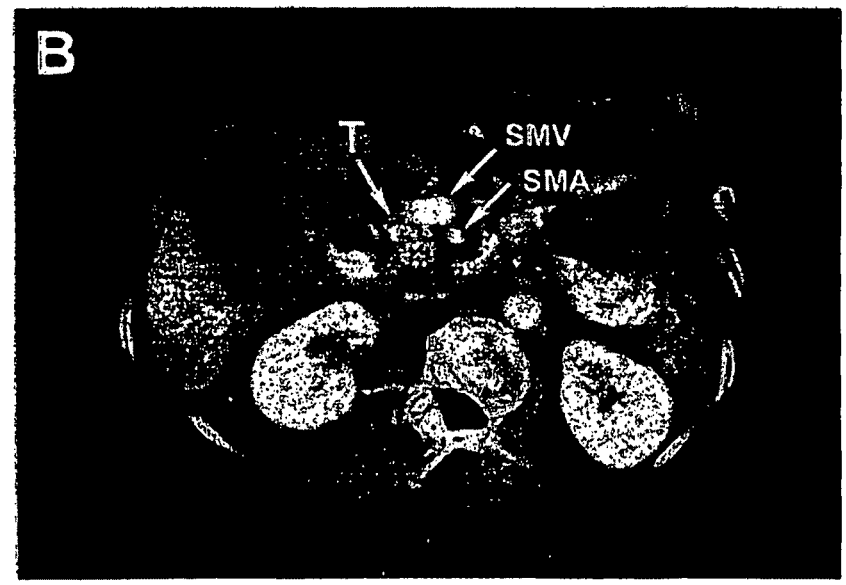

Figure 18

SEQ ID NO:2

```
              SspI MacI                                      SspI        BsrDI
                |   |                                         |          MscI
                                                                         |
TCAATATTGGCCATTAGCCATATTATTCATTGGTTATATAGCATAAATCAATATTGGCTATTGGCCATTG
AGTTATAACCGGTAATCGGTATAATAAGTAACCAATATATCGTATTTAGTTATAACCGATAACCGGTAAC
        10        20        30        40        50        60        70

BsrGI                                        Bgl I
                              |                                            |
CATACGTTGTATCTATATCATAATATGTACATTTATATTGGCTCATGTCCAATATGACCGCCATGTTGGC
GTATGCAACATAGATATAGTATTATACATGTAAATATAACCGAGTACAGGTTATACTGGCGGTACAACCG
        80        90       100       110       120       130       140

SpeI     AseI
                |        |
ATTGATTATTGACTAGTTATTAATAGTAATCAATTACGGGGTCATTAGTTCATAGCCCATATATGGAGTT
TAACTAATAACTGATCAATAATTATCATTAGTTAATGCCCCAGTAATCAAGTATCGGGTATATACCTCAA
       150       160       170       180       190       200       210

Bgl I                             AatII
                                         |                                 |
CCGCGTTACATAACTTACGGTAAATGGCCCGCCTGGCTGACCGCCCAACGACCCCCGCCCATTGACGTCA
GGCGCAATGTATTGAATGCCATTTACCGGGCGGACCGACTGGCGGGTTGCTGGGGGCGGGTAACTGCAGT
       220       230       240       250       260       270       280

AatII
                                               |
ATAATGACGTATGTTCCCATAGTAACGCCAATAGGGACTTTCCATTGACGTCAATGGGTGGAGTATTTAC
TATTACTGCATACAAGGGTATCATTGCGGTTATCCCTGAAAGGTAACTGCAGTTACCCACCTCATAAATG
       290       300       310       320       330       340       350

Bgl I                    NdeI                              AatII
                |                        |                                 |
GGTAAACTGCCCACTTGGCAGTACATCAAGTGTATCATATGCCAAGTCCGCCCCCTATTGACGTCAATGA
CCATTTGACGGGTGAACCGTCATGTAGTTCACATAGTATACGGTTCAGGCGGGGGATAACTGCAGTTACT
       360       370       380       390       400       410       420

Bgl I
                |
CGGTAAATGGCCCGCCTGGCATTATGCCCAGTACATGACCTTACGGGACTTTCCTACTTGGCAGTACATC
GCCATTTACCGGGCGGACCGTAATACGGGTCATGTACTGGAATGCCCTGAAAGGATGAACCGTCATGTAG
       430       440       450       460       470       480       490

SnaBI            NcoI
         |                |
TACGTATTAGTCATCGCTATTACCATGGTGATGCGGTTTTGGCAGTACACCAATGGGCGTGGATAGCGGT
ATGCATAATCAGTAGCGATAATGGTACCACTACGCCAAACCGTCATGTGGTTACCCGCACCTATCGCCA
       500       510       520       530       540       550       560

AatII
                                         |
TTGACTCACGGGGATTTCCAAGTCTCCACCCCCATTGACGTCAATGGGAGTTTGTTTTGGCACCAAAATCA
AACTGAGTGCCCCTAAAGGTTCAGAGGTGGGGTAACTGCAGTTACCCTCAAACAAAACCGTGGTTTTAGT
       570       580       590       600       610       620       630

SgfI
                                       PvuI
                                        |
ACGGGACTTTCCAAAATGTCGTAACAACTGCGATCGCCCGCCCCGTTGACGCAAATGGGCGGTAGGCGTG
TGCCCTGAAAGGTTTTACAGCATTGTTGACGCTAGCGGGCGGGGCAACTGCGTTTACCCGCCATCCGCAC
       640       650       660       670       680       690       700

SacI
                     Ecl136 II                                  HindIII
                       ||                                          |
TACGGTGGGAGGTCTATATAAGCAGAGCTCGTTTAGTGAACCGTCAGATCACTAGAAGCTTTATTGCGGT
ATGCCACCCTCCAGATATATTCGTCTCGAGCAAATCACTTGGCAGTCTAGTGATCTTCGAAATAACGCCA
       710       720       730       740       750       760       770
                                                                   SEQ ID NO:3
```

Figure 19B

| No. | Stedim P/N | Description | Material | Qty Ea. |
|---|---|---|---|---|
| | | *Units of Measure: Components = each/ Tubing = feet* | | |
| 1 | 100029 | Coupling Body, Female, 3/8" | POLYCARBNT | 2 |
| 2 | 100044 | Hose Barb, 3/8" to 3/8" | POLYCARBNT | 3 |
| 3 | 100045 | Hose Barb, Reducing, 1/4" 3/8" | POLYCARBNT | 1 |
| 4 | 100048 | Connector, Y, 3/8" 3/8" 3/8" | POLYCARBNT | 1 |
| 5 | 100061 | Additive Port (Latex Free) (TD | ABS/ISP/PP | 2 |
| 6 | 100066 | Plug, Tubing, Clear 1/2x1/2 | ACRYLIC | 1 |
| 7 | 100090 | Pinch Clamp for 3/8 & 1/2 Tub. | POLYESTER | 5 |
| 8 | 100128 | Spike Port/ EVA | EVA | 60 |
| 9 | 100138 | Connector, 5-Way(TD00-261) | | 10 |
| 10 | 100143 | Plug, MPC, Male | POLYCARBNT | 2 |
| 11 | 100144 | Plug, Tubing, 5/32" | POLYPROPYL | 60 |
| 12 | 100162 | Connector, T, (3/16") | POLYPROPYL | 8 |
| 13 | 100164 | Connector, Y, (1/4") | POLYPROPYL | 1 |
| 14 | 100173 | Hose Barb, (5/32" to 1/4") | POLYPROPYL | 60 |
| 15 | 100216 | Connector, T, 3/8x 3/8x 3/8 | PVC/NORTON | 1 |
| 16 | 100321 | Hose Barb, 3/8" to 1/8" | POLYCARBNT | 2 |
| 17 | 100332 | Cable Tie, 7" L.D. (w/ Flat su | NYLON | 60 |
| 18 | 100347 | Cable Tie, Black,5.6" x .14" | NYLON 12 | 225 |
| 19 | 200002 | Tubing, 3/8" ID x 3/32" Wall | SILICONE | 2 |
| 20 | 200004 | Tubing, Thick Wall, 3/8 x 1/8" | SILICONE | 11 |
| 21 | 200006 | Tubing, 3/16" ID x 1/16" WALL | SILICONE | 5 |
| 22 | 200039 | Tubing, 1/4" ID x 1/8" Wall | SILICONE | 4 |
| 23 | 200048 | Tubing, Tyg,Med Gr 1/8"IDx1/16W | PVC | 0.5 |
| 24 | 200053 | Tubing,Tygon,Med Gr 5/32x1/32W | PVC | 30 |
| 25 | 200054 | Tubing,Tygon,Med Gr 5/32x1/16W | PVC | 10 |
| 26 | 400261 | Flexboy, 10L, 3 Bare Ports, NS | STEDIM 71 | 1 |
| 27 | 400263 | Flexboy, 50L, 3 Bare Ports, NS | STEDIM 71 | 1 |
| 28 | 400503 | Bag, FLEXBOY, 500ml, 3 Bare Po | STEDIM71 | 60 |
| 29 | 500004 | Bag, Poly 8" x 10" | PLASTIC | A/R |
| 30 | 500007 | Bag, Poly 3" x 5" | PLASTIC | A/R |
| 31 | 500009 | Adhesive, Loctite, 4011 | CYANOACRYL | A/R |
| 32 | 500010 | Primer, Loctite, 7701 | N-HEPTANE | A/R |
| 33 | 500016 | Radiation Indicator, W/ Print | PAPER | A/R |
| 34 | 800003 | Bag, Poly, (42" x 26" x 63") | POLY | 0.2 |
| 35 | 800005 | Bag, Poly, 24" x 36" (6 mil) | POLY | 1 |
| 36 | 800009 | Carton, Packing, MEDIUM | CARDBOARD | 0.2 |
| 37 | 800012 | Cable Tie, Beaded, 8" | NYLON | A/R | plasmid DNA:   pB-RVE

Not I digestion to linearize:   (6.2 kb)

Hind III digestion pattern:

1.2 kb + 5.0 kb

Eco RI digestion pattern:

0.7 kb + 5.5 kb

Plasmid DNA: pdnG1/UBER-REX

Enzyme digestion pattern

| Enzymes | DNA Fragments |
|---|---|
| Sac II + Bgl II | 0.75, 1.6, 4.5 kb |
| Asc I + Not I | 0.6, 6.2 kb |

Figure 22
A. Wild Type (MoMLV ESA)
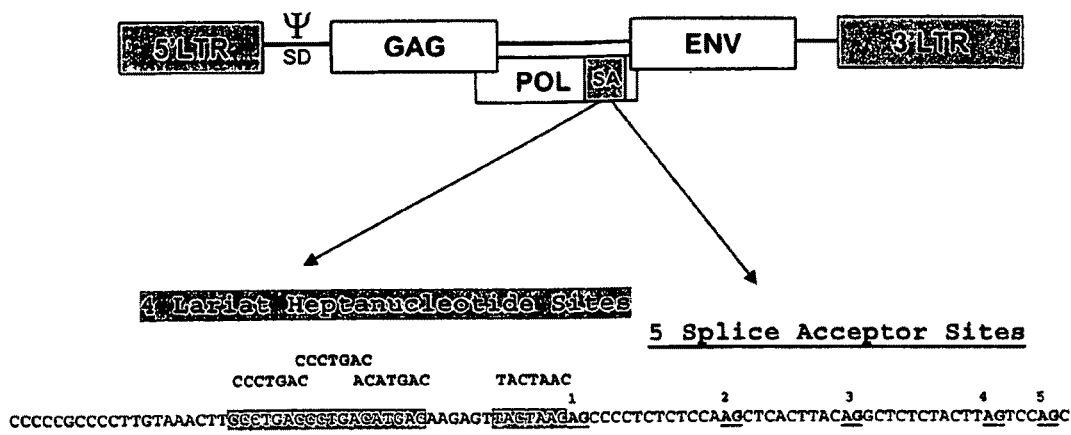
B. UBER-REX (variant ESA)
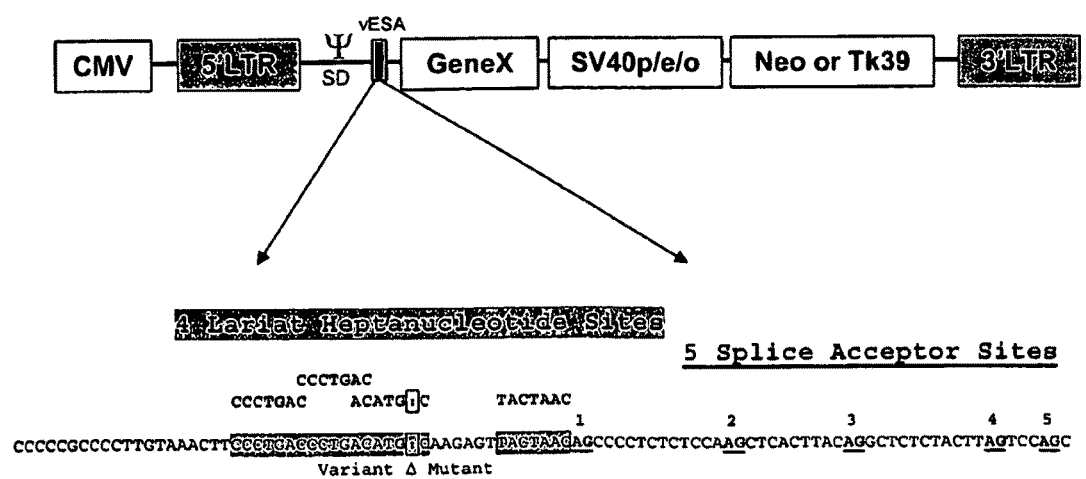

Figure 23
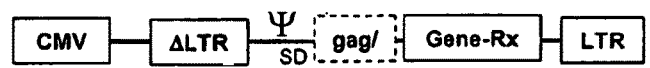
A. Schematic of the C-REX, and C-REX-II plasmids
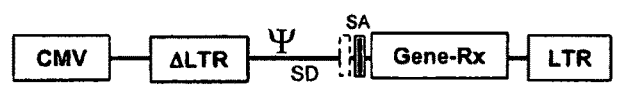
B. Schematic of the UBER-REX plasmid

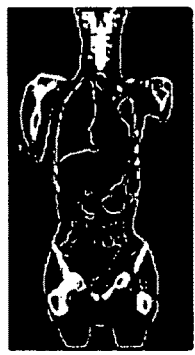
A. Baseline
04.19.07
Note: 3 target lesions
(large ellipse is heart)

B. Post-Rx
05.22.07
Note: decreased uptake
in target lesions

C. Post-Rx
07.17.07
Note: tumor calcification
and central necrosis
ePEIUS
BIOTECHNOLOGIES
Fig. 30

PATHOTROPIC TARGETED GENE DELIVERY SYSTEM FOR CANCER AND OTHER DISORDERS

CROSS-REFERENCE

This application is a §371 National Stage Application of PCT/US07/23305, filed Nov. 5, 2007, which is a continuation of U.S. application Ser. No. 11/556,666, filed Nov. 3, 2006, now abandoned which is a continuation-in-part of U.S. application Ser. No. 10/829,926, filed Apr. 21, 2004, now U.S. Pat. No. 8,052,966, which claims the benefit of U.S. Provisional Application Ser. No. 60/464,571, filed Apr. 21, 2003, which are incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 23, 2012, is named 30863-713-831-Seqlist.TXT and is 7 Kilobytes in size.

TECHNICAL FIELD

The present invention relates generally to methods and compositions for treating various diseases, disorders or conditions. Further, the invention relates to methods and systems for producing therapeutically effective vectors.

BACKGROUND OF THE INVENTION

Approximately 70% of all gene therapy protocols are aimed at treating metastatic cancer. The majority of active protocols involve some form of cancer immunotherapy via cell-based gene transfer of cytokines or tumor antigens, while others involve the intratumoral delivery of oncolytic viruses or vectors bearing prodrugs, chemoprotective agents, antisense constructs, or tumor suppressor genes. However, the major unresolved problem that has hindered the development and deployment of effective cancer gene therapy is that of inefficient delivery to target cells in vivo, a problem that obviates and precludes many direct therapeutic approaches (Tseng and Mulligan, Surg. Oncol. Clin. N. Am. 11:537-569, 2002). In this regard, the advent of pathotropic targeting launches a new paradigm in cancer gene therapy. By targeting the histopathology of the lesion—rather than the cancer cells per se—to optimize the effective vector concentration at metastatic sites, the safety and the efficacy of the circulating gene therapy vector was increased dramatically in preclinical studies (Gordon et al., Cancer Res. 60:3343-3347, 2000; Gordon et al., Hum. Gene Ther. 12:193-204, 2001). Further enhanced by the inherent properties of the murine leukemia virus-based vector (which selectively transduces dividing cells) and the strategic specificity of a cell cycle control gene which exhibits tumoricidal and anti-angiogenic activities (Gordon et al., Hum. Gene Ther. 12:193-204, 2001), the preclinical and clinical performance of the pathotropic vector establishes the potential for systemic delivery of genetic medicine for the physiologic surveillance and treatment of primary, remote, metastatic, and occult cancers.

Improved vectors, systems for producing the improved vectors, and treatment regimens for administering such vectors, are desired so that targeted delivery systems can be employed in a clinical setting.

SUMMARY OF THE INVENTION

This disclosure relates to "targeted" viral and non-viral particles, including retroviral vector particles, adenoviral vector particles, adeno-associated virus vector particles, Herpes Virus vector particles, and pseudotyped viruses such as with the vesicular stomatitis virus G-protein (VSV-G), and to non-viral vectors that contain a viral protein as part of a virosome or other proteoliposomal gene transfer vector.

Also provided are novel retroviral expression systems for the generation of targeted viral particles, the use of transiently transfected human producer cells to produce the particles, a manufacturing process for large scale production of the viral particles, and methods for collecting and storing targeted viral vectors.

In one embodiment, a method for producing a targeted delivery vector is provided. The method includes transiently transfecting a producer cell with 1) a first plasmid comprising a nucleic acid sequence encoding the 4070A amphotropic envelope protein modified to contain a collagen binding domain; 2) a second plasmid comprising i) a nucleic acid sequence operably linked to a promoter, wherein the sequence encodes a viral gag-pol polypeptide; ii) a nucleic acid sequence operably linked to a promoter, wherein the sequence encodes a polypeptide that confers drug resistance on the producer cell; and iii) an SV40 origin of replication; 3) a third plasmid comprising i) a heterologous nucleic acid sequence operably linked to a promoter, wherein the sequence encodes a diagnostic or therapeutic polypeptide; ii) 5' and 3' long terminal repeat sequences; iii) a $\Psi$ retroviral packaging sequence; iv) a CMV promoter upstream of the 5' LTR; v) a nucleic acid sequence operably linked to a promoter, wherein the sequence encodes a polypeptide that confers drug resistance on the producer cell; vi) an SV40 origin of replication. The producer cell is a human cell that expresses SV40 large T antigen. In one aspect, the producer cell is a 293T cell.

The method further includes culturing the transfected producer cells of under conditions that allow the targeted delivery vector to be produced in the supernatant of the culture and isolating and introducing the supernatant in to a closed loop manifold system for collecting the vector. An exemplary closed loop manifold system is set forth in FIG. 19A and FIG. 19B. In one embodiment, the targeted delivery vector is a viral particle. In another embodiment, the targeted delivery vector is a non-viral particle.

In one aspect, the first plasmid is the Bv1/pCAEP plasmid, the second plasmid is the pCgpn plasmid, and the third plasmid is the pdnG1/C-REX plasmid, pdnG1/C-REX II plasmid, pdnG1/UBER-REX plasmid.

The collected particles generally exhibit a viral titer of about $1 \times 10^7$ to $1 \times 10^{11}$, $1 \times 10^8$ to $1 \times 10^{11}$, $1 \times 10^9$ to $1 \times 10^{11}$, $5 \times 10^8$ to $5 \times 10^{10}$, $2 \times 10^9$ to $5 \times 10^{10}$, $3 \times 10^9$ to $5 \times 10^{10}$, $4 \times 10^9$ to $1 \times 10^{10}$, $5 \times 10^9$ to $1 \times 10^{10}$, $3 \times 10^9$ to $5 \times 10^{11}$, at least $5 \times 10^8$, $1 \times 10^9$, $2 \times 10^9$, $3 \times 10^9$, $4 \times 10^9$, $5 \times 10^9$, $8 \times 10^9$, $1 \times 10^{10}$, $5 \times 10^{10}$, or $1 \times 10^{11}$ colony forming units (cfu) per milliliter. In addition, the viral particles are generally about 10 nm to 1000 nm, 20 nm to 500 nm, 50 nm to 300 nm, 50 nm to 200 nm, or 50 nm to 150 nm in diameter.

In one embodiment, the collagen binding domain includes a peptide derived from the D2 domain of von Willebrand factor. Generally, the von Willebrand factor is derived from a mammal. The peptide includes the amino acid sequence Gly-His-Val-Gly-Trp-Arg-Glu-Pro-Ser-Phe Met-Ala-Leu-Ser-Ala-Ala (SEQ ID NO:1), or Gly-His-Val-Gly-Trp-Arg-Glu-Pro-Ser-Phe Met-Ala-Lys-Ser-Ala-Ala (SEQ ID NO:9).

In another embodiment, the peptide is contained in the gp70 portion of the 4070A amphotropic envelope protein.

In another embodiment, the therapeutic polypeptide is an N-terminal deletion mutant of cyclin G1, interleukin-2 (IL-2), granulocyte macrophage-colony stimulating factor (GM-CSF), or thymidine kinase.

Targeted delivery vectors disclosed herein generally contain nucleic acid sequences encoding diagnostic or therapeutic polypeptides. As described in greater detail in other portions of this specification, exemplary therapeutic proteins and polypeptides of the invention include, but are in no way limited to, those of the classes of suicidal proteins, apoptosis-inducing proteins, cytokines, interleukins, and TNF family proteins. Exemplary diagnostic proteins or peptides, include for example, a green fluorescent protein and luciferase.

The targeted gene delivery systems of the present invention can be used to selectively target tissues with an exposed extracellular matrix component, such as collagen (such as Type I collagen and Type IV collagen), laminin, fibronectin, elastin, glycosaminoglycans, proteoglycans or an RGD sequence. Cells in the tissues which may be infected or transduced with the vector particles of the present invention include, but are not limited to, endothelial cells, tumor cells, chondrocytes, fibroblasts and fibroelastic cells of connective tissues; osteocytes and osteoblasts in bone; endothelial and smooth muscle cells of the vasculature; epithelial and subepithelial cells of the gastrointestinal and respiratory tracts; vascular cells, connective tissue cells, and hepatocytes of a fibrotic liver, and the reparative mononuclear and granulocytic infiltrates of inflamed tissues.

Diseases or disorders which may be prevented or treated with the vector particles of the present invention include, but are not limited to, those associated with an exposed extracellular matrix component. Such diseases or disorders include, but are not limited to, pathologies characterized or associated with an abnormal or uncontrolled proliferation of cells and/or abnormal angiogenesis. Pathologies which involve abnormal cell proliferation and/or angiogenesis include, for example, cancer (such as solid and hematologic tumors, in particular, metastatic cancer), cardiovascular diseases (such as atherosclerosis and restenosis), chronic inflammation (rheumatoid arthritis, Crohn's disease), diabetes (diabetic retinopathy), psoriasis, endometriosis, neovascular glaucoma and adiposity cardiovascular diseases; cirrhosis of the liver; connective tissue disorders (including those associated with ligaments, tendons, and cartilage); vascular disorders associated with the exposition of collagen. The vector particles may be used to deliver therapeutic genes to restore endothelial cell function and to combat thrombosis, in addition to limiting the proliferative and fibrotic responses associated with neointima formation. The vector particles also may be employed in preventing or treating vascular lesions; restenosis; fibrosis such as liver and lung fibrosis; ulcerative lesions; areas of inflammation; sites of laser injury, such as the eye; corneal haze; sites of surgery; arthritic joints; scars; and keloids. The vector particles also may be employed in wound healing.

In particular, the vector particles can be employed in the prevention or treatment of tumors, including malignant and non-malignant tumors, either primary or secondary, hematological disorders, and for prevention or treatment of metastasis of cancer or tumors. Although Applicants do not intend to be limited to any theoretical reasoning, tumors, when invading normal tissues or organs, secrete enzymes such as collagenases or metalloproteinases which provide for the exposition of extracellular matrix components. By targeting vector particles to such exposed extracellular matrix components, the vector particles become concentrated at the exposed matrix components which are adjacent the tumor, whereby the vector particles then infect the tumor cells. Such tumors include, but are not limited to, carcinoma, sarcomas, such as breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, fibrosarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic lymphocytic leukemia, chronic myelogenous leukemia, the myelodysplastic syndromes, and sickle cell anemia.

In one embodiment, a method of preventing or reducing the risk of developing a disease or disorder associated with an exposed extracellular matrix component in a subject is provided. The method comprises administering to the subject a targeted vector of the present invention.

In another embodiment, a method of inhibiting metastasis of cancer in a subject having cancer is provided. The method comprises administering to the subject a targeted vector of the present invention.

In another embodiment, a method of treating a subject having a disease or disorder associated with an exposed extracellular matrix component is provided. The method comprises administering to the subject a targeted vector of the present invention. The method may optionally include administering to the subject another therapeutic agent such as a chemical therapeutic agent and a biological agent, or treating the subject in combination with other therapy such radiation, surgery and thermalysis, prior to, contemporaneously with, or subsequent to the administration of the targeted vector.

Examples of chemotherapeutic agents include, but are not limited to, alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33: 183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubincin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g. paclitaxel (TAXOL™, Bristol Meyers Squibb Oncology, Princeton, N.J.) and docetaxel (TAXOTERE™, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluromethylornithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above.

In a particular embodiment, the therapeutic agent in combination with the targeted vector is a tyrosine kinase inhibitor, such as ZD1839 (Iressa™ of AstraZeneca K.K.); IMC-C225 or cetuximab (Erbitux™); Trastuzumab (HERCEPTIN™); imatinib mesylate (GLEEVEC™, formerly STI-571); and Sorafenib (Nexavar™).

The biological agent may be a therapeutic antibody such as Rituximab (RITUXAN™); Alemtuzumab (CAMPATH™); and Gemtuzumab zogamicin (MYLOTARG™).

By practicing the present inventions using the targeted vectors, the subject being treated, especially a human subject, would not only have the disease being prevented or ameliorated, but also have an improved quality life as the inventive targeted therapy would have much reduced or eliminated side effects commonly associated with other types of therapies such as chemotherapies and biologic therapies, including alopecia or hair loss, bone marrow suppression, significant alteration in liver and kidney functions, nausea and vomiting, mucositis, skin rash or constipation.

In a variation of the embodiment, the method includes a first phase protocol comprising contacting a subject with a viral particle described herein, wherein the subject is contacted with i) a first viral particle dose level of about $1 \times 10^9$ to $6 \times 10^9$ Units/day administered to the subject for 1 to about 6 days in succession; ii) a second viral particle dose level of about $7 \times 10^9$ to about $1 \times 10^{10}$ Units/day administered to the subject for 1 to about 3 days in succession and subsequent to administration of the first vector dose; and iii) a viral particle dose level of about $1 \times 10^{10}$ to about $5 \times 10^{10}$ Units/day administered to the subject for 1 to about 3 days in succession and subsequent to administration of the second vector dose. The method further includes a second phase protocol comprising contacting a subject with a viral particle produced as described herein, wherein the subject is contacted with a viral particle dose level of about $1 \times 10^9$ to about $5 \times 10^{10}$ Units/day administered to the subject for 1 to about 15 days in succession and subsequent to the first phase protocol.

According to the variation, the method optionally includes administering a chemotherapeutic agent to the subject prior to, contemporaneously with, or subsequent to the phase one and phase two protocols. The first viral particle dose level can be about $4 \times 10^9$ to $5 \times 10^9$ Units/day. The second viral particle dose level can be about $9 \times 10^9$ to about $1 \times 10^{10}$ Units/day. The third viral particle dose level can be about $1 \times 10^{10}$ to about $2 \times 10^{10}$ Units/day.

Targeted delivery vectors disclosed herein can be administered topically, intravenously, intra-arterially, intracolonically, intratracheally, intraperitoneally, intranasally, intravascularly, intrathecally, intracranially, intramarrowly, intrapleurally, intradermally, subcutaneously, intramuscularly, intraocularly, intraosseously and/or intrasynovially.

In another embodiment, a plasmid including a multiple cloning site functionally-linked to a promoter, wherein the promoter supports expression of a heterologous nucleic acid sequence; 5' and 3' long terminal repeat sequences; a Ψ retroviral packaging sequence; a CMV promoter positioned upstream of the 5' LTR; a nucleic acid sequence operably linked to a promoter, wherein the sequence encodes a polypeptide that confers drug resistance on a producer cell containing the plasmid; and an SV40 origin of replication. Exemplary plasmids include pC-REX II, pC-REX and pUBER-REX. Additional derivatives of the exemplary include those that contain a heterologous nucleic acid sequence encoding a therapeutic or diagnostic polypeptide.

In other embodiments, a kit for the production of targeted delivery vectors is provided. The kit generally includes containers containing plasmids disclosed herein for the production of, for example, viral particle. Such kits can further include a producer cell suitable for transfecting with the plasmids, and instructions for transiently transfecting the producer cell with the plasmids. The instructions can further include methods for culturing the transfected producer cell under conditions that allow targeted delivery vectors to be produced. For example, a kit for the production of targeted viral particles can include containers containing the Bv1/pCAEP plasmid, the pCgpn plasmid, and the pdnG1/C-REX plasmid, the pdnG1/C-REX II plasmid, or the pdnG1/UBER-REX plasmid. Such a kit can further include 293T cells and instructions for transiently transfecting cells with the plasmids and culturing the transfected cell under conditions that allow targeted viral particles to be produced.

In another embodiment, a kit for treating a neoplastic disorder is provided. The kit includes a container containing a viral particle produced by a method described herein in a pharmaceutically acceptable carrier and instructions for administering the viral particle to a subject. The administration can be according to the exemplary treatment protocol provided in Table 1.

In another embodiment, a method for conducting a gene therapy business is provided. The method includes generating targeted delivery vectors and establishing a bank of vectors by harvesting and suspending the vector particles in a solution of suitable medium and storing the suspension. The method further includes providing the particles, and instructions for use of the particles, to a physician or health care provider for administration to a subject (patient) in need thereof. Such instructions for use of the vector can include the exemplary treatment regimen provided in Table 1. The method optionally includes billing the patient or the patient's insurance provider.

In yet another embodiment, a method for conducting a gene therapy business, including providing kits disclosed herein to a physician or health care provider, is provided.

In yet another embodiment, a method of treating a subject having a tumor or tumors containing cancer cells with therapeutic viral particles is provided. The method comprises a) determining the dose of the therapeutic viral particles by i) determining the subject's tumor burden as defined by the number of cancer cells residing in the subject's tumor, or the total number of tumor cells in the tumors; ii) multiplying the tumor burden by the physiological multiplicity of infection (pMOI) of the therapeutic viral particles; and iii) dividing the resultant figure by the titer of the therapeutic viral particles to yield the volume of the therapeutic viral particles to be administered to the subject; and b) administering the determined dose of the therapeutic viral particles to the subject.

According to the embodiment, the subject is treated with the therapeutic viral particles at the determined dose of the therapeutic viral particles per day for 1 to 5 days, or 1 to about 6 days in succession. Optionally, the subject is treated with the therapeutic viral particles at the determined dose of the therapeutic viral particles per day for on Monday, Wednesday, and Friday in succession. The subject may be allowed to rest 1 to 2 days, which constitutes a treatment cycle. The subject may be treated for 2-8 treatment cycles, preferably for 3-4 treatment cycles.

Also according to the embodiment, the dose of the therapeutic viral particles in a unit of milliliters may be calculated based on the following general formula:

$$\frac{\text{Tumor Burden (number of cancer cells)} \times pMOI}{\text{Viral } Titer \text{ (colony forming units } (C.F.U.)/\text{ml)}}$$

wherein pMOI is from 4 to 250, preferably 100.

Also according to the embodiment, the method may further include the following steps: after the subject is treated with the determined dose of the therapeutic viral particles, determining the tumor burden of the subject; recalculating the dose of the therapeutic viral particles; and administering the therapeutic viral particles to the subject at the recalculated dose.

Also according to the embodiment, the tumor burden is determined by the following formula:

$$\text{(the sum of the longest diameters (cm) of target lesion or tumor)} \times 1 \times 10^9 \text{ cancer cells/cm.}$$

The target lesion or tumor may be measured by calipers, or by radiologic imaging such as MRI, CT, PET, or SPECT scan.

Also according to the embodiment, the therapeutic viral particle is administered topically, intravenously, intra-arterially, intracolonically, intratracheally, intraperitoneally, intranasally, intravascularly, intrathecally, intracranially, intramarrowly, intrapleurally, intradermally, subcutaneously, intramuscularly, intraocularly, intraosseously and/or intrasynovially. Preferably the therapeutic viral particle is administered to the subject via intravenously infusion.

Also according to the embodiment, the subject is a mammal, preferably a human.

Also according to the embodiment, the cancer is selected from the group consisting of breast cancer, skin cancer, bone cancer, prostate cancer, liver cancer, lung cancer, brain cancer, uterine cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal gangiloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas. The cancer is preferably osteosarcoma, sarcoma, pancreatic cancer, breast cancer, or colon cancer.

Also according to the embodiment, the therapeutic viral particles are inventive viral vectors disclosed here, such as viral vectors which are retroviral (preferably amphotropic) vectors having an envelope protein modified to contain a collagen binding domain, and encodes a therapeutic agent (such as a cytocidal mutant of cyclin G1) against the cancer.

Also according to the embodiment, the method may further include the following step: administering to the subject a chemotherapeutic agent, a biologic agent, or radiotherapy prior to, contemporaneously with, or subsequent to the administration of the therapeutic viral particles.

These, and other aspects, embodiments, objects and features of the present invention, as well as the best mode of practicing the same, will be more fully appreciated when the following detailed description of the invention is read in conjunction with the accompanying drawings.

BRIEF DESCRIPTION OF THE DRAWINGS

FIG. 1A depicts a representative MRI from Patient #1 one day after completion of treatment cycle #1 showing a large round recurrent tumor (T; bracketed area) in the region of the pancreas within the area of the surgical bed and an enlarged para-aortic lymph node (N) indicating metastasis.

FIG. 1B depicts a follow-up MRI from Patient #1 four days after completion of treatment cycle #2 showing an irregularity in the shape of the recurrent tumor (T; bracketed area) with a large area of central necrosis (nec) involving 40-50% of the tumor mass, and a significant decrease in the size of the para-aortic lymph node metastasis (N).

FIG. 2A provides a representative abdominal CT scan from Patient #2 obtained at the beginning of treatment cycle #1 revealing a 6.0 cm3 mass in the region of the pancreatic head (T) encroaching on the superior mesenteric vein (SMV) and the superior mesenteric artery (SMA).

FIG. 2B provides a follow-up abdominal CT scan from Patient #2 two days after completion of treatment cycle #2, revealing that the pancreatic tumor mass (T) has decreased in size and regressed away from the superior mesenteric vessels (SMV and SMA). The start of each treatment cycle is indicated by arrows.

Figure 11A:
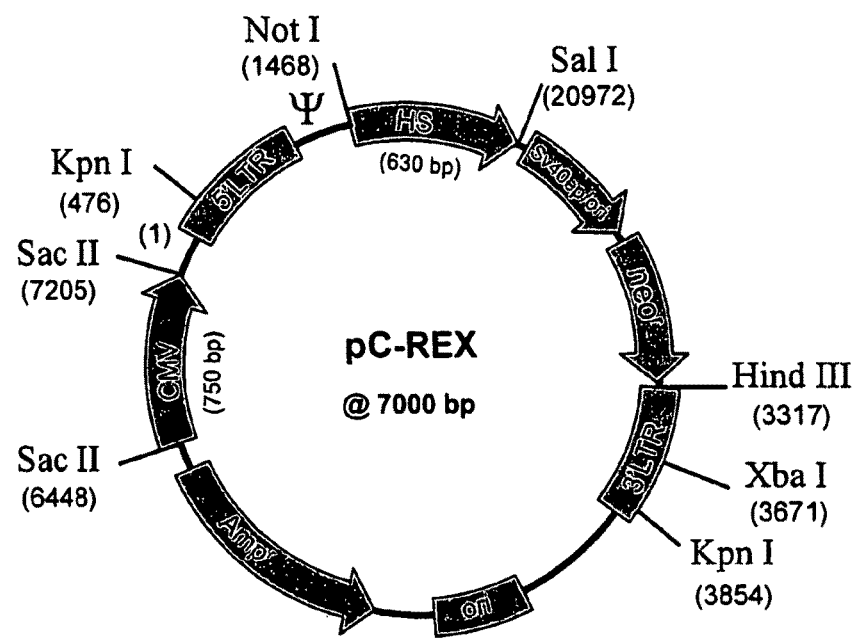
Figure 11:
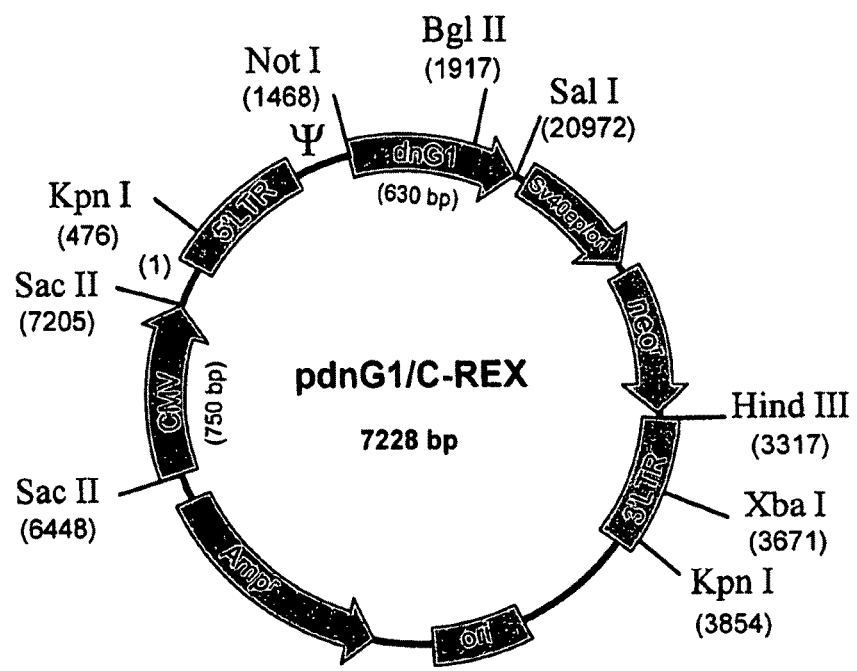

FIG. 11A depicts a restriction map of the pC-REX plasmid. The plasmid is derived from G1XSvNa (Genetic Therapy, Inc.), into which the CMV i.e. promoter enhancer was cloned at the unique Sac II site upstream of the 5' LTR. A heterologous nucleic acid sequence (HS) encoding a diagnostic or therapeutic polypeptide can be included between the Not 1 and Sal 1 restriction sites. The neo gene is driven by the SV40 e.p. with its nested ori. The resulting pC-REX plasmid was designed for high-titer vector production in 293T cells.

FIG. 11B depicts a restriction map of the pdnG1/C-REX plasmid. The plasmid is identical to the pC-REX plasmid shown in FIG. 11A except that it contains a nucleic acid sequence encoding the 209 aa (630 bp) dominant negative mutant dnG1 (472-1098 nt; 41-249 aa; Accession #U47413) which was prepared by PCR to include Not 1 and Sal 1 overhangs.

Figure 11C:
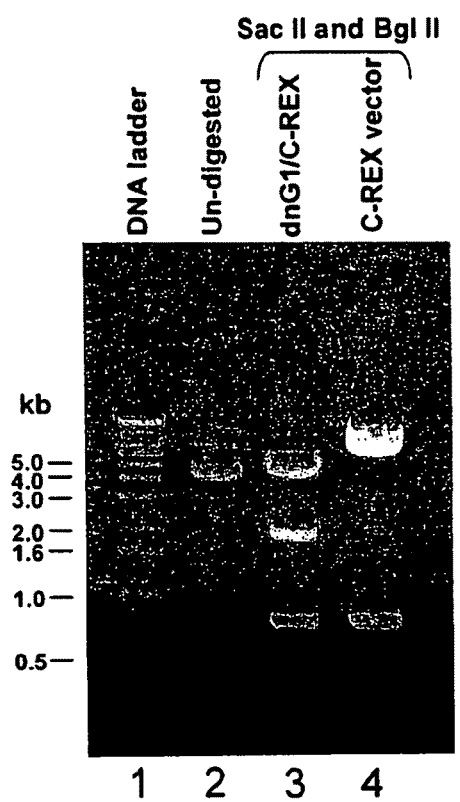

FIG. 11C depicts a restriction digest of pdnG1/C-REX.

Figure 12:
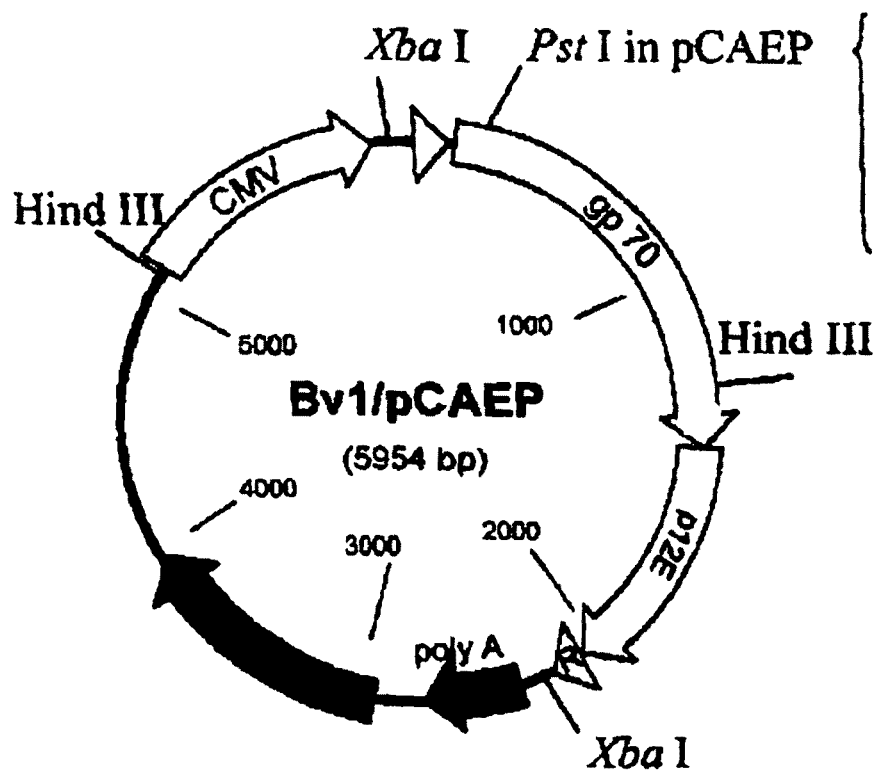

FIG. 12A depicts a restriction map of the Bv1/pCAEP plasmid. CAEP (P=Pst 1) was created by the addition of a unique Pst 1 site near the N-terminus of the CAE amphotropic envelope protein (4070A), between aa 6 and 7 of the mature gp70 polypeptide. Bv1 is a collagen-binding decapeptide derived from vWF, flanked by strategic linkers, and inserted as in-frame coding sequences into the Pst 1 site of PCAEP.

Figure 12B:
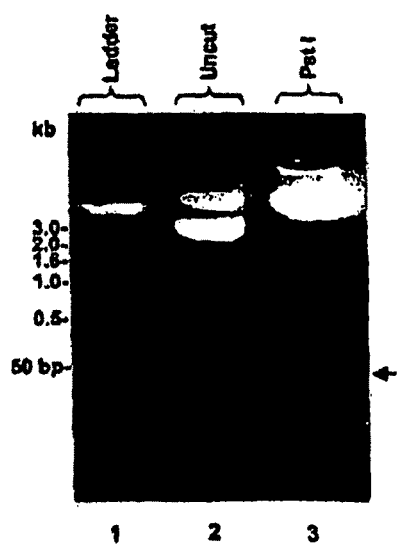

FIG. 12B depicts a restriction digest of Bv1/pCAEP.

Figure 13A:
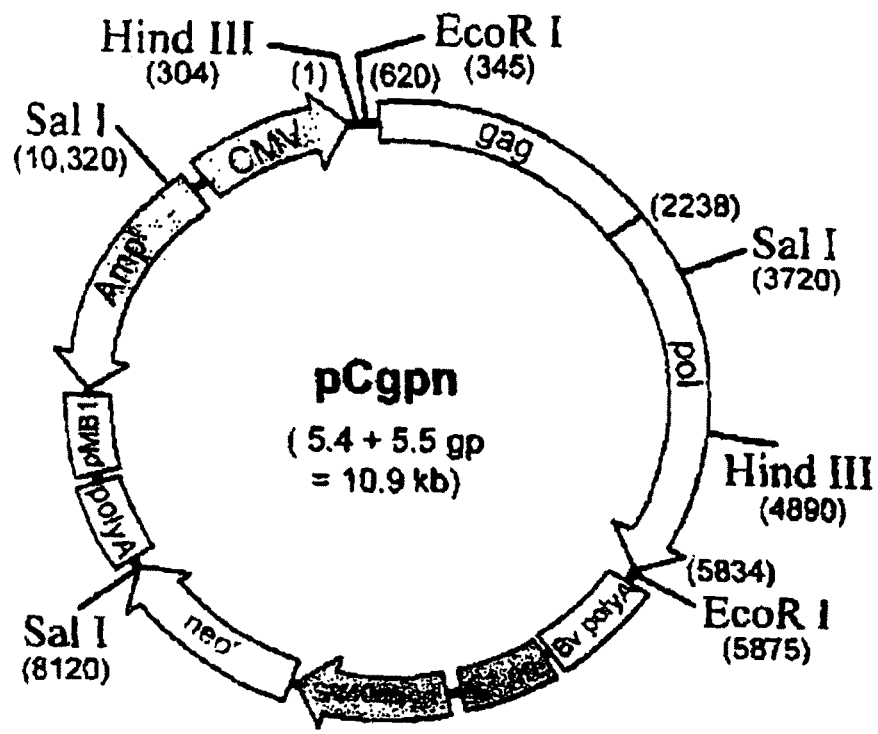

FIG. 13A depicts a restriction map of the pCgpn plasmid. This plasmid encodes the MoMuLv gag-pol driven by the CMV immediate-early promoter enhancer. The gag-pol coding sequence flanked by EcoR 1 cloning sites was derived from clone 3PO as pGag-pol-gpt (Moarkowitz et al., 1988). The vector backbone is pcDNA3.1+ (Invitrogen). Polyadenylation signal and transcription termination sequences from bovine growth hormone enhance RNA stability. An SV40 ori is featured along with the e.p. for episomal replication in cell lines that express SV40 large T antigen.

Figure 13B:
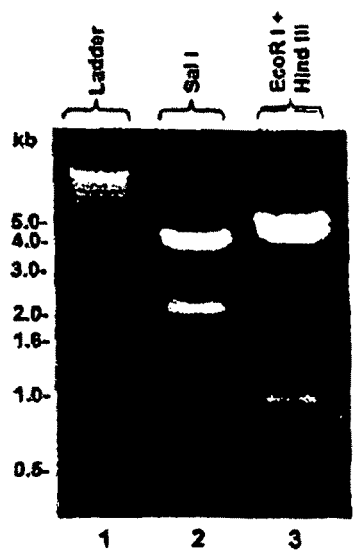

FIG. 13B depicts a restriction digest of pCgpn.

Figure 14:
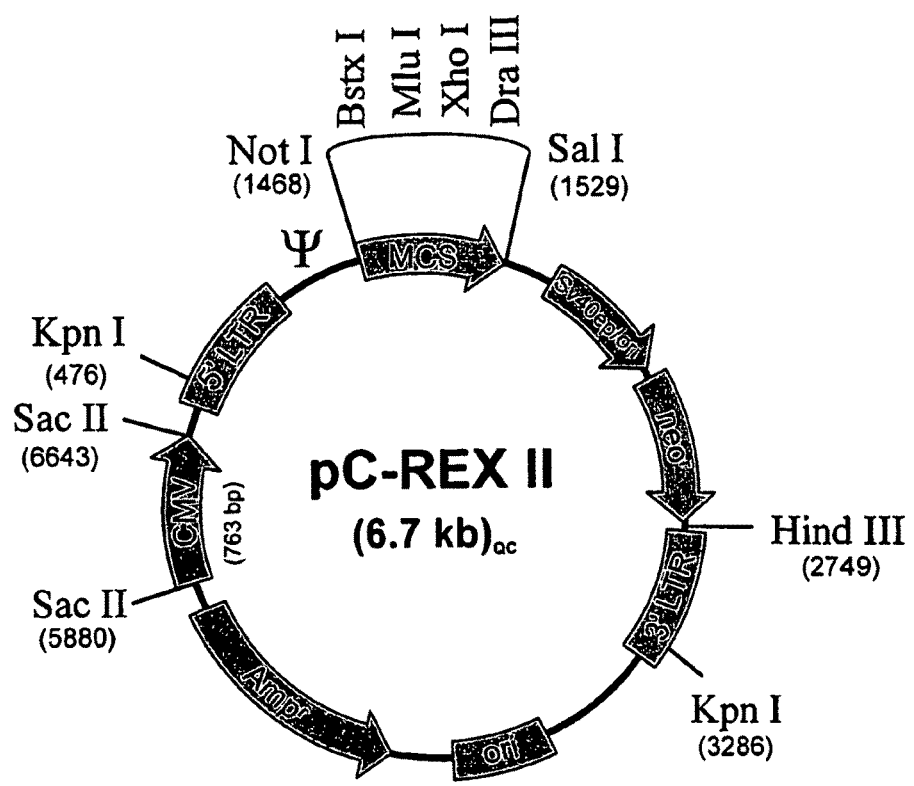

FIG. 14 depicts a map of the novel pC-REX II (i.e., EPEIUS-REX) plasmid.

Figure 15:
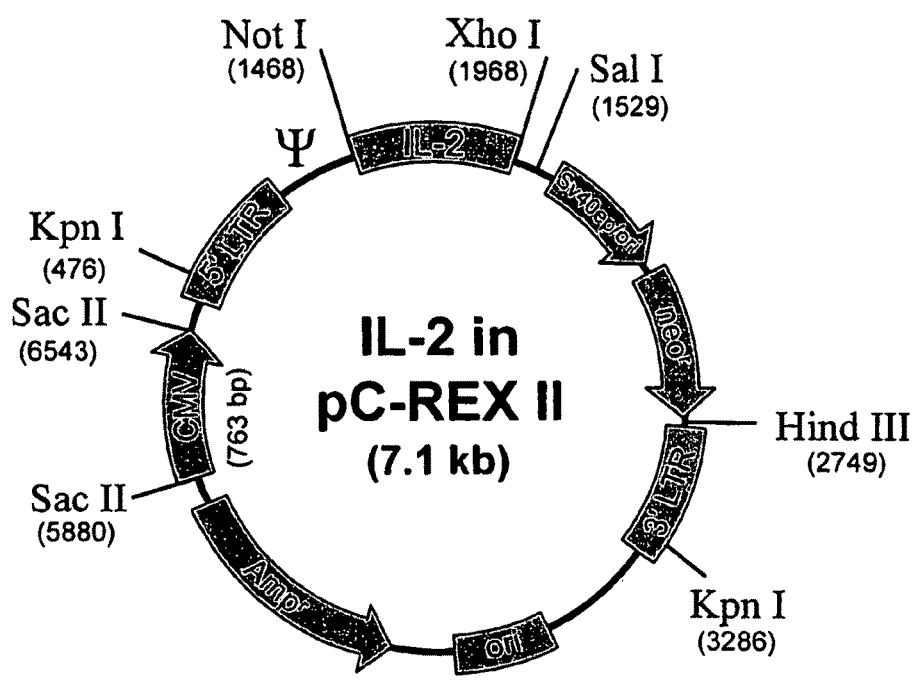

FIG. 15 depicts a map of the novel pC-REX II (i.e., EPEIUS-REX) plasmid with the therapeutic cytokine gene IL-2 inserted.

Figure 16:
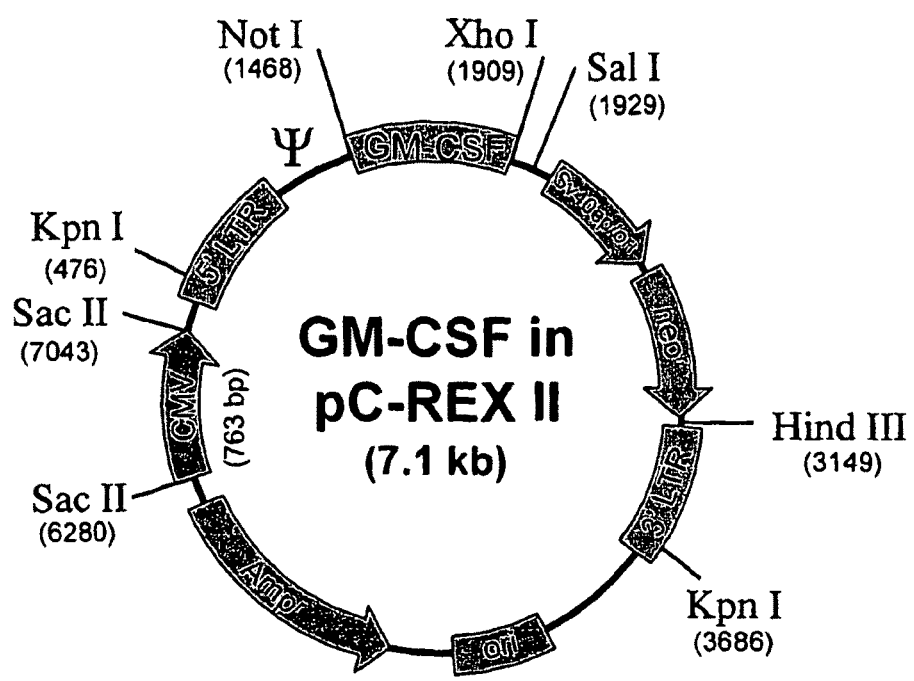

FIG. 16 depicts a map of the novel pC-REX II (i.e., EPEIUS-REX) plasmid with the therapeutic cytokine gene GM-CSF inserted.

FIG. 17A-G depicts a complex series of auxiliary promoters proximal to the HStk (reporter) gene utilizing the MCS sites of pC-REX II.

Figure 17:
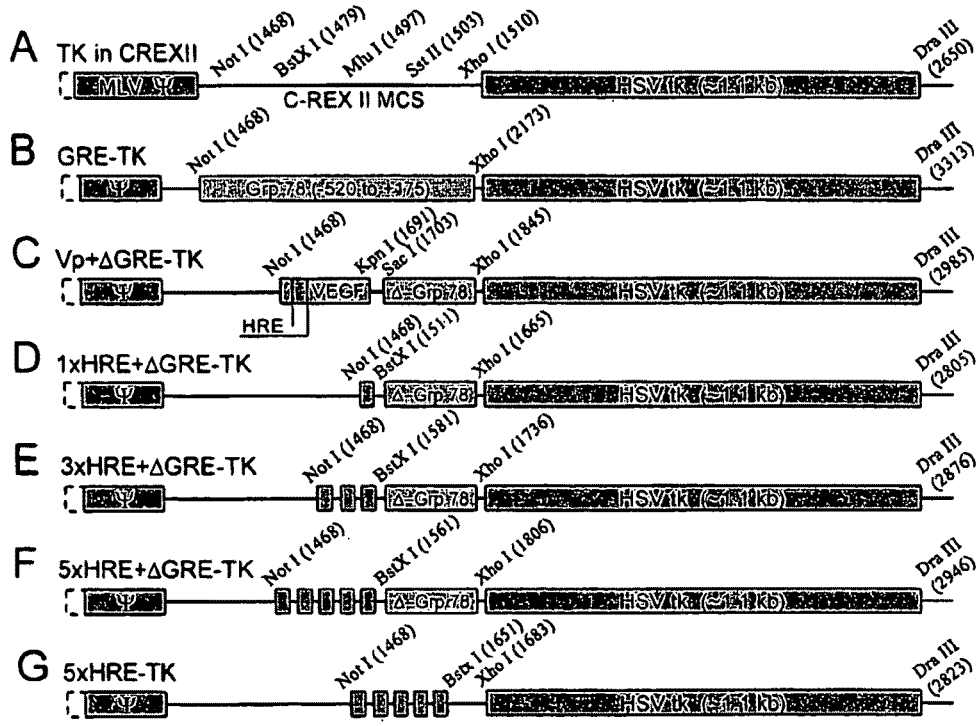
Figure 17H:
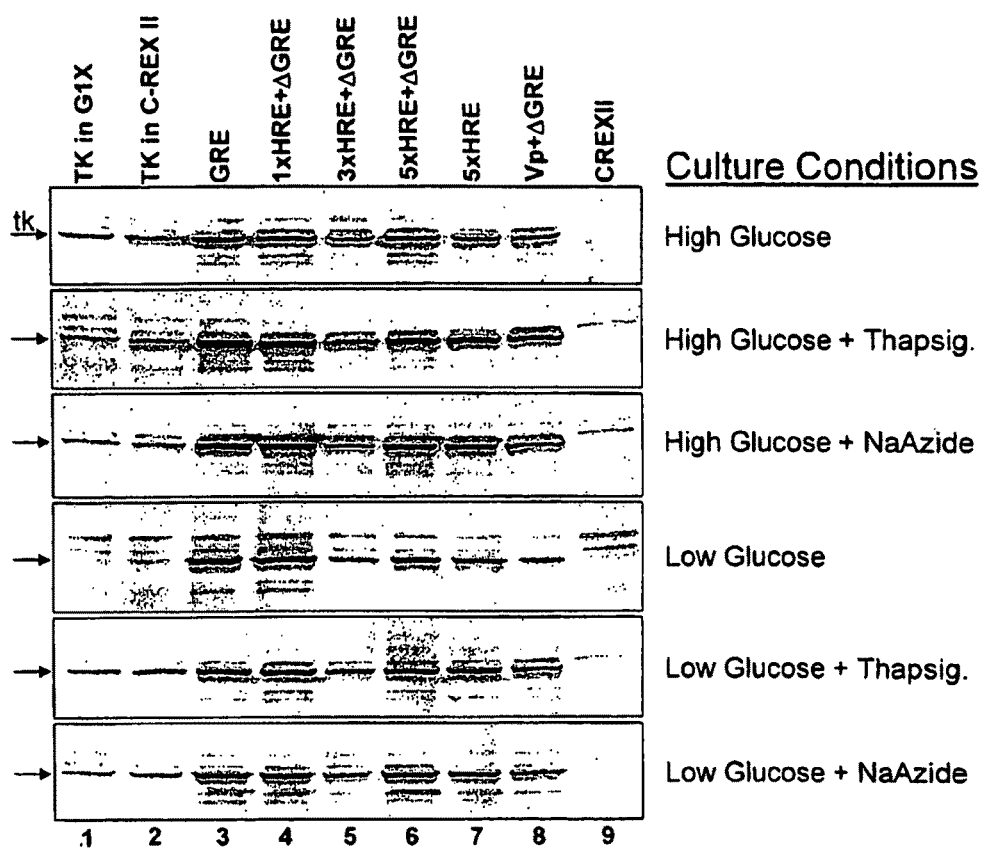

FIG. 17H depicts a Western blot of differential gene expression in tumor cells from the auxiliary promoters shown in FIGS. 17A-G.

FIG. 18 depicts the nucleic acid sequence of the CMV promoter sequence from pIRES. FIG. 18 discloses SEQ ID NOS 2-3, respectively, in order of appearance.

Figure 19A:
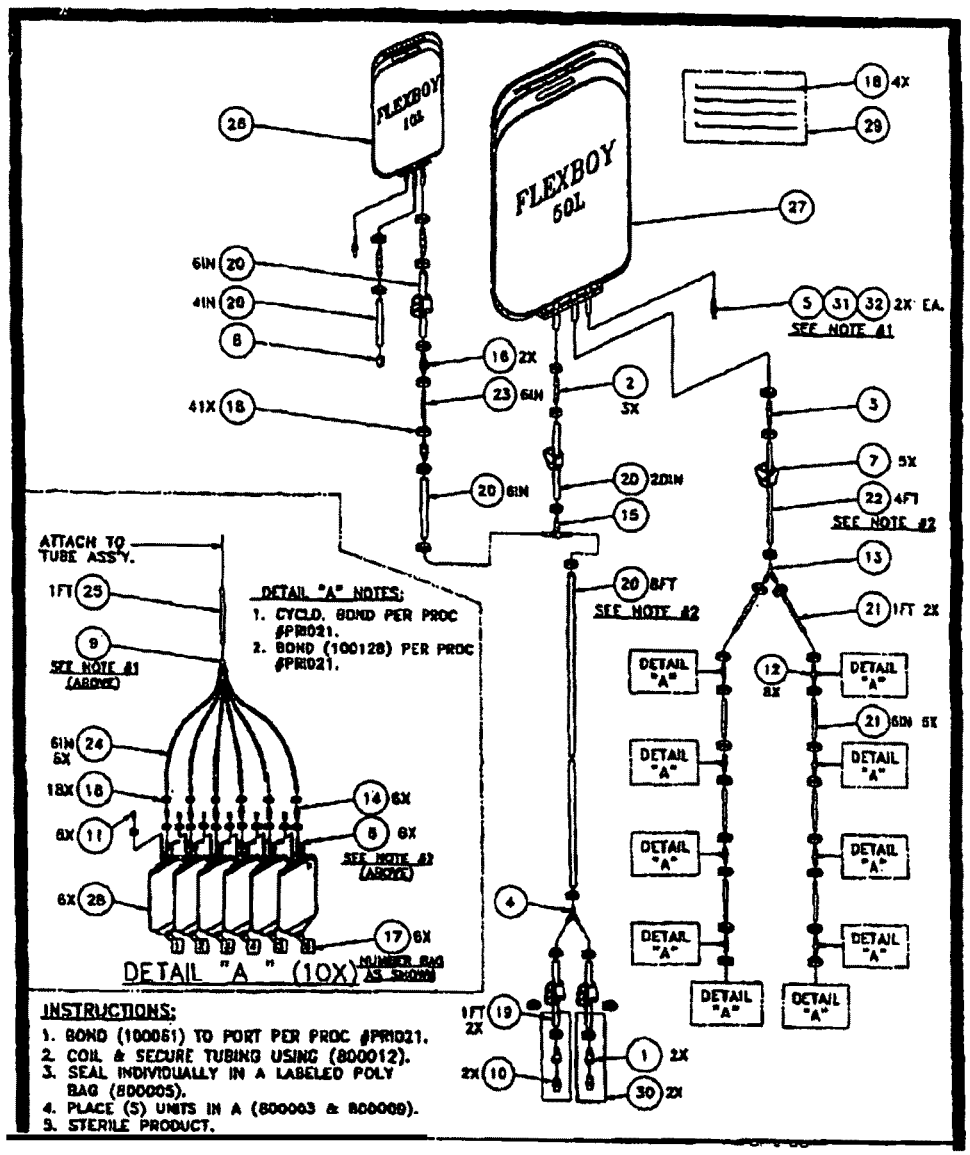

FIG. 19A depicts a closed-loop manifold system for producing targeted vectors.

FIG. 19B provides information regarding the components of the closed-loop manifold system.

Figure 20A:
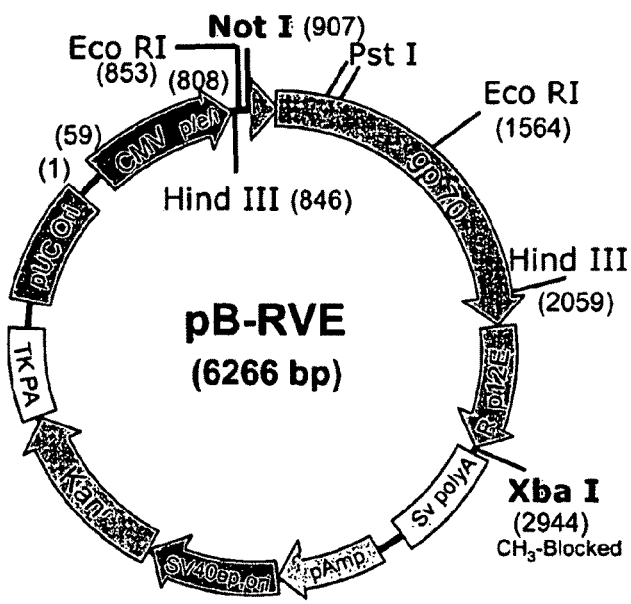

FIG. 20A depicts a map of the novel pB-RVE plasmid, an enhanced CMV expression plasmid bearing a targeted retroviral vector envelope construct (Epeius-BV1): a minimal amphotropic env (4070A) modified by the addition of a unique restriction site near the N-terminus of the mature protein (CAE-P); engineered to exhibit a collagen-binding motif (GHVGWREPSFMALSAA; SEQ ID NO: 1); and re-generated by PCR to eliminate all upstream (5') and downstream (3') viral sequences. The plasmid backbone (ph-CMV1) provides an optimized CMV prompter/enhancer/intron to drive the expression of env, in addition to an SV40 promotor/enhancer, which enables episomal replication in vector producer cells expressing the SV40 large T antigen (293T). Positive selection is provided by the kanamycin resistance gene.

Figure 20B:
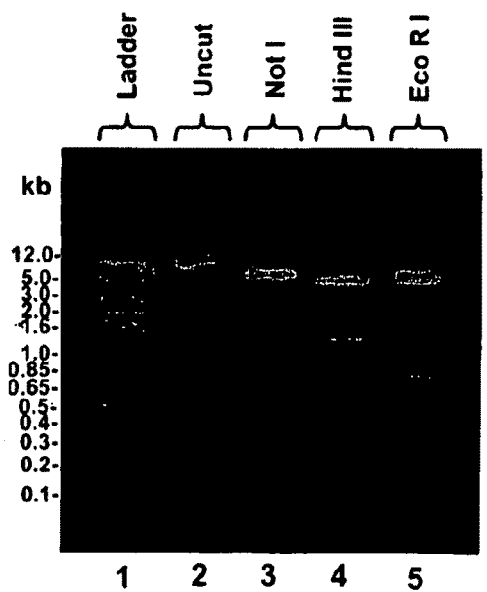

FIG. 20B depicts a restriction digest of pB-RVE.

Figure 21A:
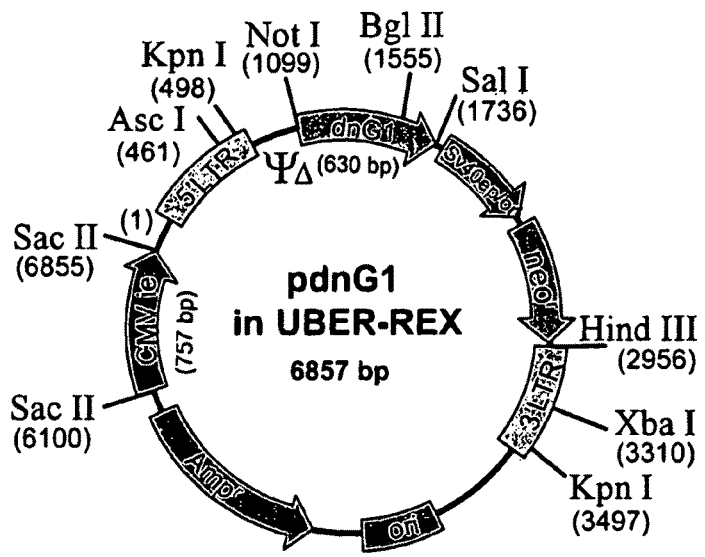
Figure 21B:
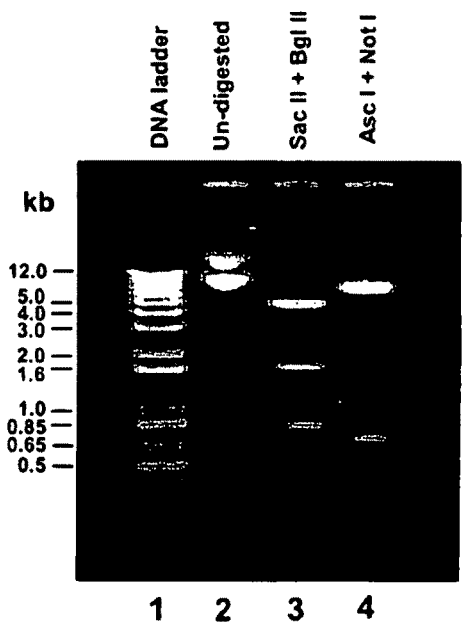

FIG. 21A depicts a map of the novel pdnG1/UBER-REX plasmid. This plasmid encodes the 209 aa (630 bp) dominant-negative mutant dnG1 (472-1098 nt; 41-249 aa; Accession #U47413). The plasmid is derived from G1XSvNa (GTI), into which the CMV i.e. promoter enhancer was cloned at the unique Sac II site upstream of the 5' LTR. 487 bp of residual gag sequences were removed (D) to reduce the possibility of RCR, and a 97 bp splice acceptor site (ESA) was added upstream of dnG1. The dnG1 coding sequence (nt 472-1098 plus stop codon=1101) was prepared by PCR, including Not I and Sal I overhangs. The neo gene is driven by the SV40 e.p. with its nested ori. The pdnG1/UBER-REX plasmid was designed for high-titer vector production in 293T cells FIG. 21B depicts the restriction digest of pdnG1/UBER-REX.

FIG. 22A depicts a map of the wild type Moloney Murine Leukemia Virus (MoMLV) Envelope Splice Acceptor Site (ESA) (SEQ ID NO: 10).

FIG. 22B depicts a map of the pUBER-REX Envelope Splice Acceptor Site (ESA) (SEQ ID NO: 11).

FIG. 23A illustrates a schematic representation of the C-REX plasmid.

FIG. 23B illustrates a schematic representation of the UBER-REX plasmid.

Figure 24:
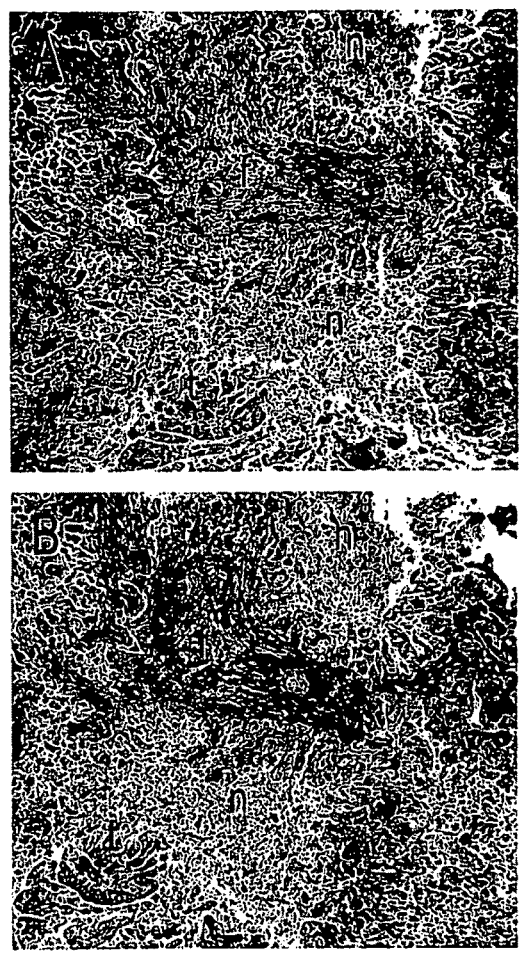

FIG. 24 depicts intravenous Rexin-G™ induced necrosis and fibrosis in metastatic tumor nodules, as observed in surgically excised liver sections from a patient with Stage IV pancreatic cancer (Patient A3). (A) Representative hematoxylin-eosin stained tissue section of a tumor nodule in biopsied liver; t=tumor cells; n=necrosis; f=fibrosis. (B) Trichrome stain of a tissue section of same tumor nodule. Blue-staining material indicates presence of collagenous proteins in fibrotic areas.

Figure 25:
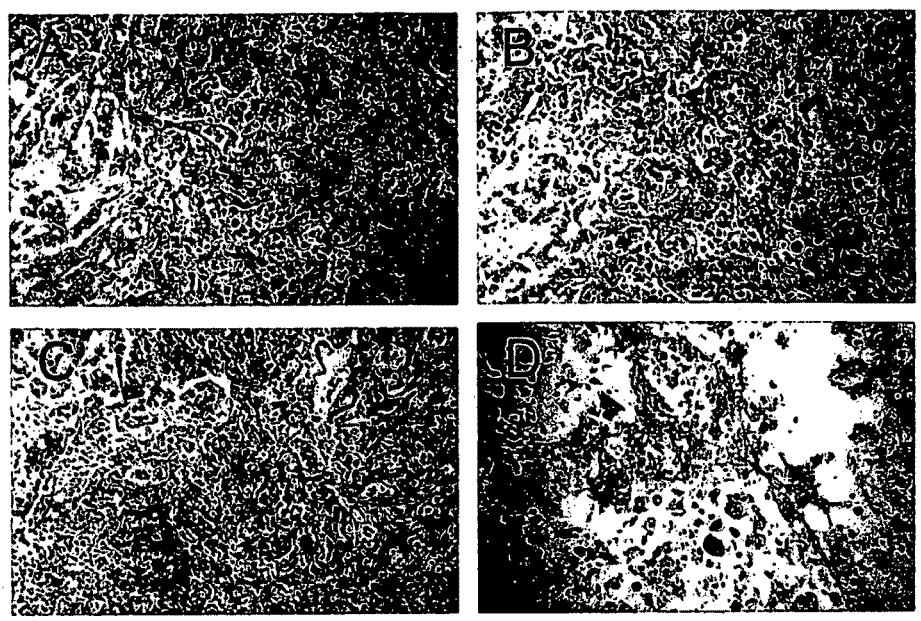

FIG. 25 depicts intravenous Rexin-G™ induced overt apoptosis in metastatic tumor nodules, seen of a patient with pancreatic cancer (Patient A3). (A-D) Representative immunostained tissue sections of tumor nodules from biopsied liver indicating an appreciable incidence of Tunel-positive apoptotic nuclei (brown-staining material).

Figure 26:
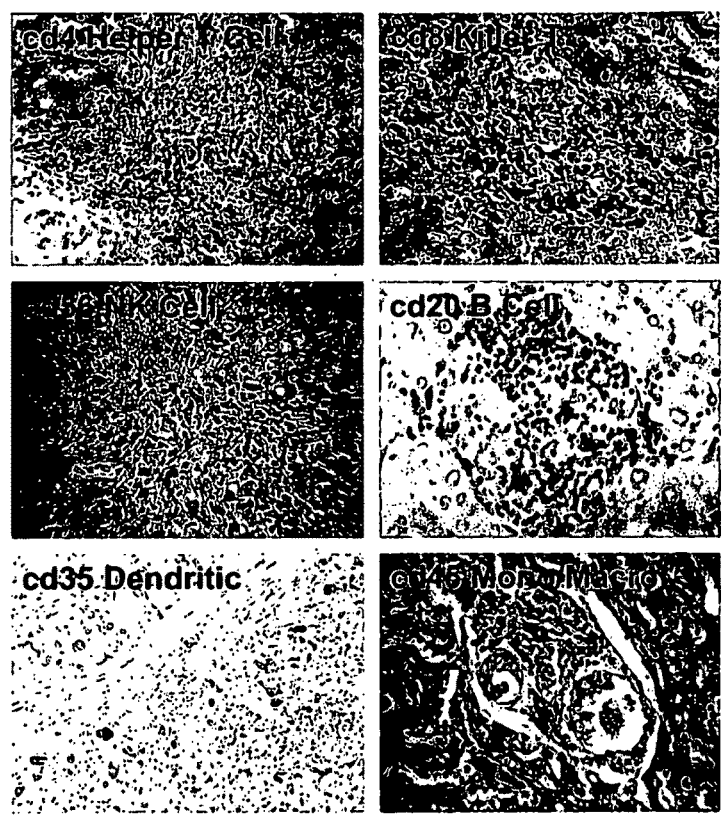

FIG. 26 depicts immunohistochemical characterization of tumor infiltrating lymphocytes (TILs) in metastatic tumor nodules excised from a Rexin-G™-treated patient with pancreatic cancer (Patient A3). Representative tissue sections of residual tumor nodules within the biopsied liver show significant TIL infiltration with a functional complement of immunoreactive T and B cells. Clockwise from upper left: Helper T cells (cd4+), Killer T cells (cd8+), B cells (cd20+), Monocyte/Macrophages (cd45+), Dendritic cells (cd35+), and Natural Killer cells (cd56+). Note, the presence (i.e., migration) of a cadre of TILs that function in the context of cell-mediated and humoral immunity, suggests the potential for cancer immunization in an immune competent host.

Figure 27:
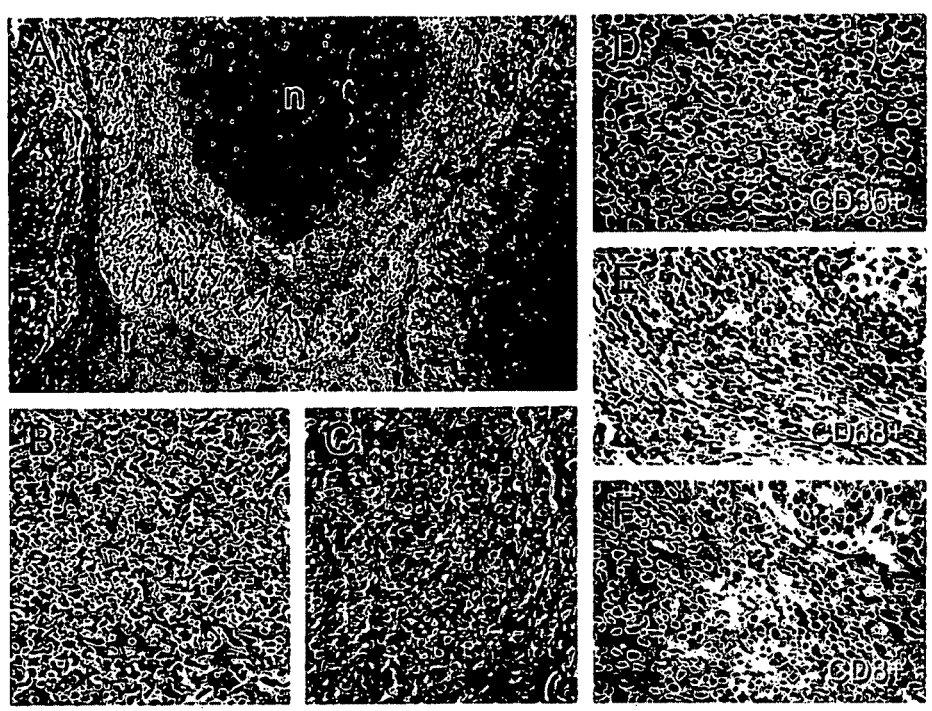

FIG. 27 depicts intravenous Rexin-G™ induced necrosis, apoptosis and fibrosis in a cancerous lymph node of a patient with malignant melanoma (Patient B4). A) H&E stained tissue sections of inguinal lymph node revealing extensive necrosis (n), apoptosis (indicated by arrows) and fibrosis (f) of cancer cells with a rim of viable tumor cells in the periphery (t); (B) Higher magnification (100×) of sections of A showing numerous cells undergoing apoptosis indicated by small cells with pyknotic or fragmented nuclei; (C) Higher magnification (100×) of A revealing golden-yellow hemosiderin-laden macrophages; (D) Representative tissue sections of inguinal lymph node showing significant infiltration with immunoreactive CD35+ dendritic cells, (E) CD68+ macrophages and (F) CD8+ killer T cells.

Figure 28:
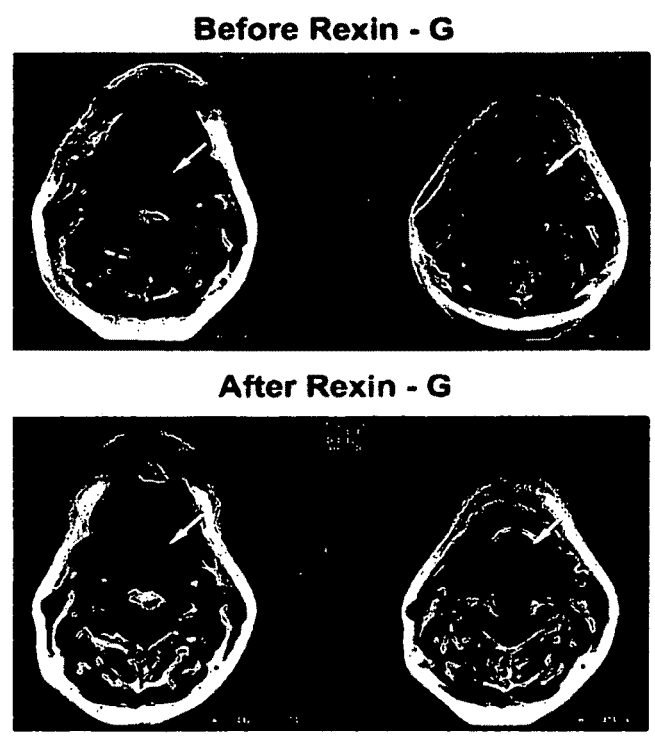

FIG. 28 depicts evidence of tumor regression in a patient with squamous cell carcinoma of the larynx (Patient B6). MRI images of the neck region obtained before (upper panel) and after (lower panel) Rexin-G™ treatment. Measurement of the diameters of serial sections of the upper airway shows a dramatic (~300%) increase in the upper airway diameters after repeated infusions of Rexin-G™ when compared to sections obtained prior to treatment (indicated by white arrows). The increased patency of the airway corresponded to regression of the surrounding tumor mass, and a return of vocal capabilities.

Figure 29:
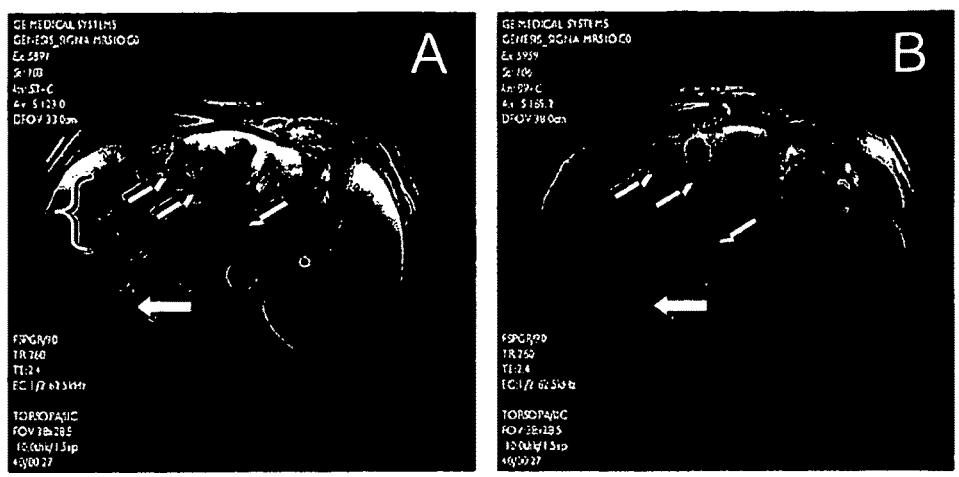

FIG. 29 depicts the effects of Rexin G™ infusions on the number and quality of hepatic metastatic lesions observed in a pancreatic cancer patient exhibiting a massive tumor burden (Patient C1). Abdominal MRI obtained (A) before treatment and (B) after treatment with calculated (Calculus of Parity) dose-dense infusions of Rexin-G™. Note the complete eradication of numerous small dense tumor nodules in the upper left quadrant of the image (bracketed), as well as cystic conversion of established liver nodules (black arrows). Subsequent aspiration of the enlarged liver cyst (white arrow) followed by cytological analysis confirmed the complete absence of cancer cells in the aspirates following the treatment.

FIG. 30 depicts sequential CT-PET images of a chemotherapy refractory osteosarcoma patient. Antitumor activity of Rexin-G is evidenced by the reduced $^{18}$FDG uptake in lesions 1 month post-treatment and increased calcification lesion 2 months post-treatment.

Figure 31:
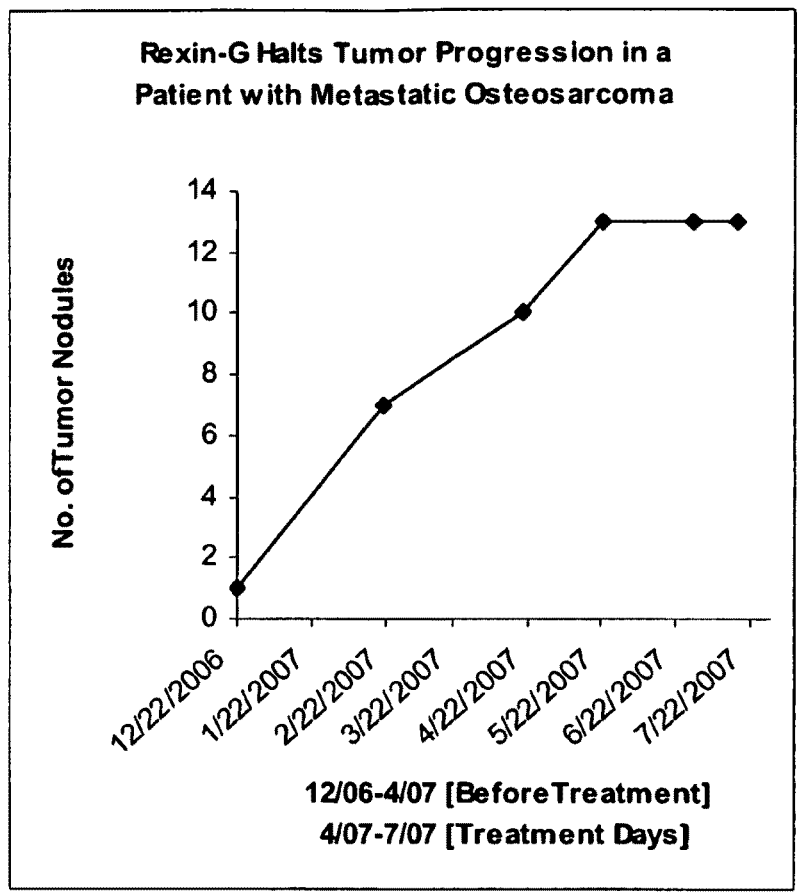

FIG. 31 depicts the decrease in the rate of tumor progression in a patient with chemotherapy refractory metastatic osteosarcoma following Rexin-G treatment as evidenced by no new lesions after the second treatment cycle.

Figure 32:
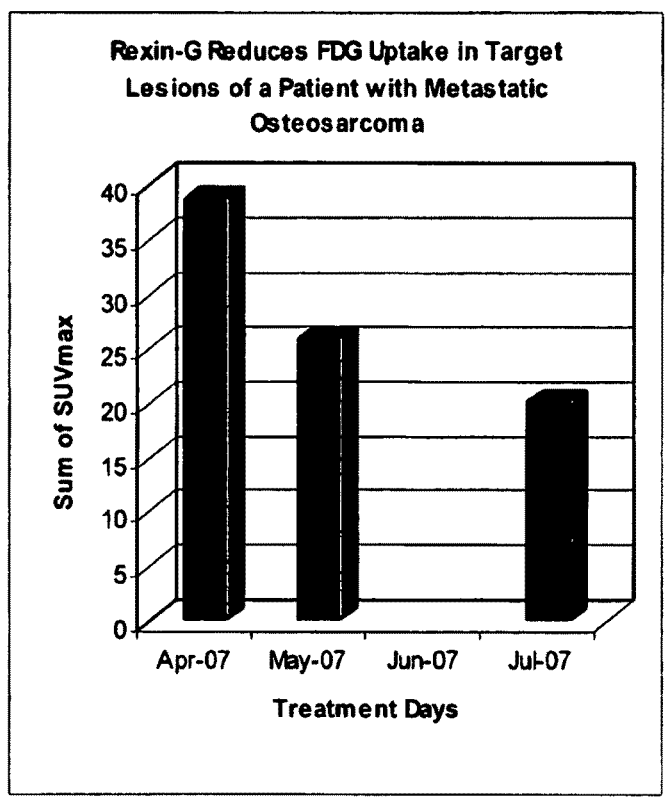

FIG. 32 depicts the progressive reduction in SUVmax of 18FDG uptake in target lesion of a patient with chemotherapy refractory metastatic osteosarcoma following Rexin-G treatment.

Figure 33:
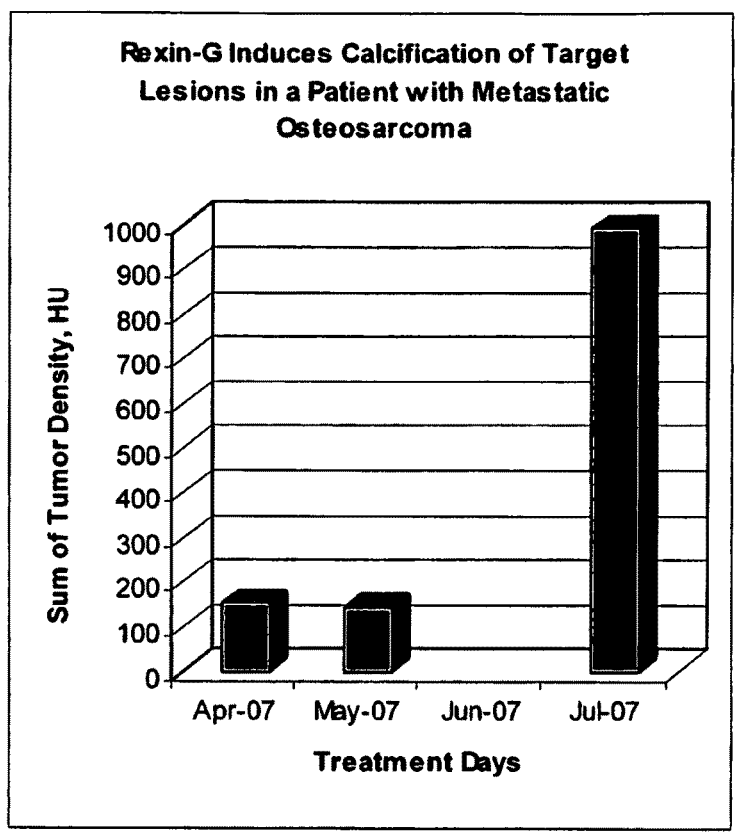

FIG. 33 depicts the increase in calcification in the cancerous lesions of a patient with chemotherapy refractory metastatic osteosarcoma following Rexin-G treatment as evidenced by increase in Hounsfield Units.

Figure 34:
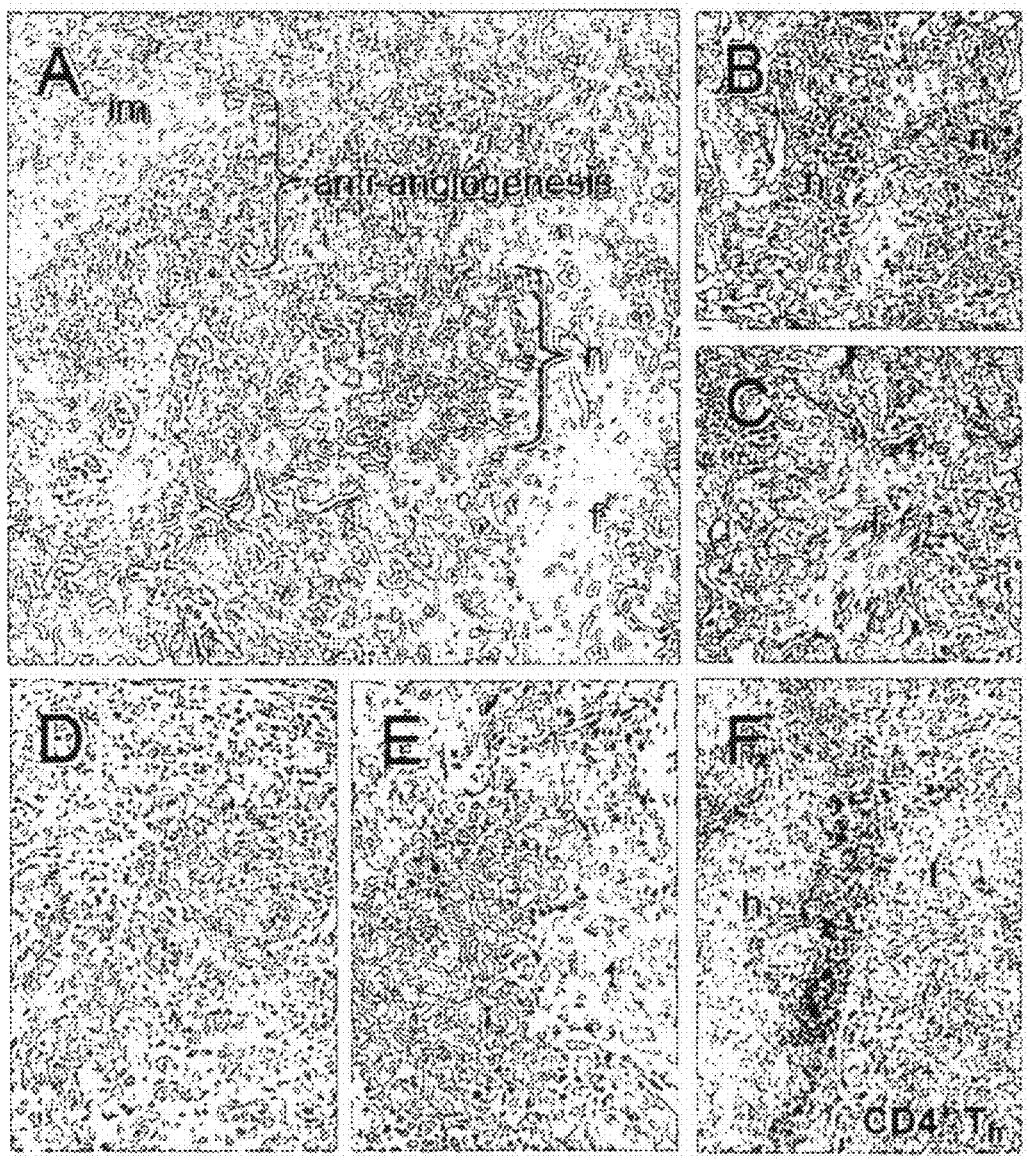

FIG. 34 depicts extensive necrosis and localized GM-CSF production within the primary pancreatic tumor of a patient with intractable Stage IV pancreatic cancer. (A) H&E stained tissue sections of primary pancreatic tumor demonstrate extensive (~95%) necrosis (n) of cancer cells, with some reactive fibrosis (f), with a degenerative (deg) rim of viable tumor cells and organoid structures seen in at the periphery. (B&C) Higher magnification of the fibrotic, necrotic, and degenerative areas of the section seen in (A). (D) Immunostaining for the GM-CSF transgene identifies small clusters of immunoreactive GM-CSF secreting tumor cells (arrows) remaining within this inoperable primary tumor. (E) Higher magnification of D showing immunoreactive GM-CSF protein within viable residual tumor cells (indicated by darker staining material); (F) Close examination of areas with significant immune infiltrate, are indicative of GM-CSF positivity in necrotic tumor cells (indicated by arrows) and in fragments of tumor cell debris accompanied by mononuclear cell infiltration (im).

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The targeted delivery system targets retroviral vectors or any other viral or non-viral vector, protein or drug selectively to areas of pathology (i.e., pathotropic targeting), enabling preferential gene delivery to vascular (Hall et al., Hum Gene Ther, 8:2183-92, 1997; Hall et al., Hum Gene Ther, 11:983-93, 2000) or cancerous lesions (Gordon et al., Hum Gene Ther 12:193-204, 2001; Gordon et al., Curiel D T, Douglas J T, eds. *Vector Targeting Strategies for Therapeutic Gene Delivery*, New York, N.Y.: Wiley-Liss, Inc. 293-320, 2002), areas of active angiogenesis, and areas of tissue injury or inflammation with high efficiency in vivo.

Definitions

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "nucleic acid" refers to a polynucleotide containing at least two covalently linked nucleotide or nucleotide analog subunits. A nucleic acid can be a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) Nucl. Acids Res. 22:5220-5234; Jellinek et al. (1995) Biochemistry 34:11363-11372; Pagratis et al. (1997) Nature Biotechnol. 15:68-73). The nucleic acid can be single-stranded, double-stranded, or a mixture thereof. For purposes herein, unless specified otherwise, the nucleic acid is double-stranded, or it is apparent from the context.

As used herein, DNA is meant to include all types and sizes of DNA molecules including cDNA, plasmids and DNA including modified nucleotides and nucleotide analogs.

As used herein, nucleotides include nucleoside mono-, di-, and triphosphates. Nucleotides also include modified nucleotides, such as, but are not limited to, phosphorothioate nucleotides and deazapurine nucleotides and other nucleotide analogs.

As used herein, the term "subject" refers to animals, plants, insects, and birds into which the large DNA molecules can be introduced. Included are higher organisms, such as mammals and birds, including humans, primates, rodents, cattle, pigs, rabbits, goats, sheep, mice, rats, guinea pigs, cats, dogs, horses, chicken and others.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

As used herein, "targeted delivery vector" or "targeted delivery vehicle" refers to both viral and non-viral particles that harbor and transport exogenous nucleic acid molecules to a target cell or tissue. Viral vehicles include, but are not limited to, retroviruses, adenoviruses and adeno-associated viruses. Non-viral vehicles include, but are not limited to, microparticles, nanoparticles, virosomes and liposomes. "Targeted," as used herein, refers to the use of ligands that are associated with the delivery vehicle and target the vehicle to a cell or tissue. Ligands include, but are not limited to, antibodies, receptors and collagen binding domains.

As used herein, "delivery," which is used interchangeably with "transduction," refers to the process by which exogenous nucleic acid molecules are transferred into a cell such that they are located inside the cell. Delivery of nucleic acids is a distinct process from expression of nucleic acids.

As used herein, a "multiple cloning site (MCS)" is a nucleic acid region in a plasmid that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector.

As used herein, "origin of replication" (often termed "ori"), is a specific nucleic acid sequence at which replication is initiated. Alternatively an autonomously replicating sequence (ARS) can be employed if the host cell is yeast.

As used herein, "selectable or screenable markers" confer an identifiable change to a cell permitting easy identification of cells containing an expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

As used herein, "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

As used herein, "applying to a subject" is a procedure by which target cells present in the subject are eventually contacted with energy such as ultrasound or electrical energy. Application is by any process by which energy can be applied.

The term "host cell" denotes, for example, microorganisms, yeast cells, insect cells, and mammalian cells, that can be, or have been, used as recipients for multiple constructs for producing a targeted delivery vector. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, "genetic therapy" involves the transfer of heterologous DNA to the certain cells, target cells, of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

Plasmids

Plasmids disclosed herein are used to transfect and produce targeted delivery vectors for use in therapeutic and diagnostic procedures. In general, such plasmids provide nucleic acid sequences that encode components, viral or non-viral, of targeted vectors disclosed herein. Such plasmids include nucleic acid sequences that encode, for example the 4070A amphotropic envelope protein modified to contain a collagen binding domain. Additional plasmids can include a nucleic acid sequence operably linked to a promoter. The sequence generally encodes a viral gag-pol polypeptide. The plasmid further includes a nucleic acid sequence operably linked to a promoter, and the sequence encodes a polypeptide that confers drug resistance on the producer cell. An origin of replication is also included. Additional plasmids can include a heterologous nucleic acid sequence encoding a diagnostic or therapeutic polypeptide, 5' and 3' long terminal repeat sequences; a Ψ retroviral packaging sequence, a CMV promoter upstream of the 5' LTR, a nucleic acid sequence operably linked to a promoter, and an SV40 origin of replication.

The heterologous nucleic acid sequence generally encodes a diagnostic or therapeutic polypeptide. In specific embodiments, the therapeutic polypeptide or protein is a "suicide protein" that causes cell death by itself or in the presence of other compounds. A representative example of such a suicide protein is thymidine kinase of the herpes simplex virus. Additional examples include thymidine kinase of varicella zoster virus, the bacterial gene cytosine deaminase (which converts 5-fluorocytosine to the highly toxic compound 5-fluorouracil), p450 oxidoreductase, carboxypeptidase G2, beta-glucuronidase, penicillin-V-amidase, penicillin-G-amidase, beta-lactamase, nitroreductase, carboxypeptidase A, linamarase (also referred to as .beta.-glucosidase), the *E. coli* gpt gene, and the *E. coli* Deo gene, although others are known in the art. In some embodiments, the suicide protein converts a prodrug into a toxic compound. As used herein, "prodrug" means any compound useful in the methods of the present invention that can be converted to a toxic product, i.e. toxic to tumor cells. The prodrug is converted to a toxic product by the suicide protein. Representative examples of such prodrugs include: ganciclovir, acyclovir, and FIAU (1-(2-deoxy-2-fluoro-.beta.-D-arabinofuranosyl)-5-iod-ouracil) for thymidine kinase; ifosfamide for oxidoreductase; 6-methoxypurine arabinoside for VZV-TK; 5-fluorocytosine for cytosine deaminase; doxorubicin for beta-glucuronidase; CB1954 and nitrofurazone for nitroreductase; and N-(Cyanoacetyl)-L-phenylalanine or N-(3-chloropropionyl)-L-phenylalanine for carboxypeptidase A. The prodrug may be administered readily by a person having ordinary skill in this art. A person with ordinary skill would readily be able to determine the most appropriate dose and route for the administration of the prodrug.

In some embodiments, a therapeutic protein or polypeptide, is a cancer suppressor, for example p53 or Rb, or a nucleic acid encoding such a protein or polypeptide. Of course, those of skill know of a wide variety of such cancer suppressors and how to obtain them and/or the nucleic acids encoding them.

Other examples of therapeutic proteins or polypeptides include pro-apoptotic therapeutic proteins and polypeptides, for example, p15, p16, or p21.sup.WAF-1.

Cytokines, and nucleic acid encoding them may also be used as therapeutic proteins and polypeptides. Examples include: GM-CSF (granulocyte macrophage colony stimulating factor); TNF-alpha (Tumor necrosis factor alpha); Interferons including, but not limited to, IFN-alpha and IFN-gamma; and Interleukins including, but not limited to, Interleukin-1 (IL1), Interleukin-Beta (IL-beta), Interleukin-2 (IL2), Interleukin-4 (IL4), Interleukin-5 (IL5), Interleukin-6 (IL6), Interleukin-8 (IL8), Interleukin-10 (IL10), Interleukin-12 (IL12), Interleukin-13 (IL13), Interleukin-14 (IL14), Interleukin-15 (IL15), Interleukin-16 (IL16), Interleukin-18 (IL18), Interleukin-23 (IL23), Interleukin-24 (IL24), although other embodiments are known in the art.

Additional examples of cytocidal genes includes, but is not limited to, mutated cyclin G1 genes. By way of example, the cytocidal gene may be a dominant negative mutation of the cyclin G1 protein (e.g., WO/01/64870).

Previously, retroviral vector (RV) constructs were generally produced by the cloning and fusion of two separate retroviral (RV) plasmids: one containing the retroviral LTRs, packaging sequences, and the respective gene(s) of interest; and another retroviral vector containing a strong promoter (e.g., CMV) as well as a host of extraneous functional sequences. The pC-REX II (e-REX) vector disclosed herein refers to an improved plasmid containing an insertion of a unique set of cloning sites in the primary plasmid to facilitate directional cloning of the experimental gene(s). The strong promoter (ex, CMV) is employed in the plasmid backbone to increase the amount of RNA message generated within the recipient producer cells but is not itself packaged into the retroviral particle, as it lies outside of the gene-flanking retroviral LTR's.

Therefore, an improved plasmid was designed which included the strong CMV promoter (obtained by PCR) into a strategic site within the G1xSvNa vector, which was previously approved for human use by the FDA, thus eliminating the plasmid size and sequence concerns of previously reported vectors. This streamlined construct was designated pC-REX. PC-REX was further modified to incorporate a series of unique cloning sites (see MCS in pC-REX II, FIG. 14), enabling directional cloning and/or the insertion of multiple genes as well as auxiliary functional domains. Thus, the new plasmids are designated pC-REX and pC-REX II (EPEIUS-REX or eREX). The pC-REX plasmid design (see FIG. 11A) outperformed that of pHIT-112/pREX in direct side-by-side comparisons. The new plasmid design was further modified to include the coding sequence of various therapeutically effective polypeptides. In one example, the dominant negative Cyclin G1 (dnG1) (see FIG. 11B) was included as the therapeutic gene. The tripartite viral particle (env, gag-pol, and dnG1 gene vector construct) has been referred to collectively as REXIN-G™ in published reports of the clinical trials. Thus, REXIN-G represents the targeted delivery vector dnG1/C-REX that is packaged, encapsidated, and enveloped in a targeted, injectable viral particle.

The incidence of replication-competent retrovirus in a transient plasmid co-transfection system such as the system used in Rexin-G production is unlikely, because the murine-based retroviral envelope construct, the packaging construct gag pol, and the retroviral vector are expressed in separate plasmids driven by their own promoters. Additionally, human producer cells are used to generate virions. Human cells do not have endogenous murine sequences that would be capable of recombining with a murine-based retroviral vector used in Rexin-G Recent improvements were made to the production of REXIN-G in order to further reduce the potential for generation of replication-competent retrovirus. The plasmid dnG1/C-REX contains residual gag-pol sequences that potentially overlap with 5' DNA sequences contained in the respective gag-pol construct. Therefore, 487 base pairs were removed from the parent dnG1/C-REX plasmid followed by an insertion of 97 base pair splice acceptor site to yield pdnG1/UBER-REX (FIG. 21A).

A targeting ligand is included in a plasmid disclosed herein. Generally, it is inserted between two consecutively numbered amino acid residues of the native (i.e., unmodified) receptor binding region of the retroviral envelope encoded by a nucleic acid sequence of a plasmid, such as in the modified amphotropic CAE envelope polypeptide, wherein the targeting polypeptide is inserted between amino acid residues 6 and 7. The polypeptide is a portion of a protein known as gp70, which is included in the amphotropic envelope of Moloney Murine Leukemia Virus. In general, the targeting polypeptide includes a binding region which binds to an extracellular matrix component, including, but not limited to, collagen (including collagen Type I and collagen Type IV), laminin, fibronectin, elastin, glycosaminoglycans, proteoglycans, and sequences which bind to fibronectin, such as arginine-glycine-aspartic acid, or RGD, sequences. Binding regions which may be included in the targeting polypeptide include, but are not limited to, polypeptide domains which are functional domains within von Willebrand Factor or derivatives thereof, wherein such polypeptide domains bind to collagen. In one embodiment, the binding region is a polypeptide having the following structural formula: Trp-Arg-Glu-Pro-Ser-Phe-Met-Ala-Leu-Ser (SEQ ID NO: 4).

Methods for Producing Targeted Vectors

This disclosure relates to the production of viral and non-viral vector particles, including retroviral vector particles, adenoviral vector particles, adeno-associated virus vector particles, Herpes Virus vector particles, pseudotyped viruses, and non-viral vectors having a modified, or targeted viral surface protein, such as, for example, a targeted viral envelope polypeptide, wherein such modified viral surface protein, such as a modified viral envelope polypeptide, includes a targeting polypeptide including a binding region which binds to an extracellular matrix component such as collagen. The targeting polypeptide may be placed between two consecutive amino acid residues of the viral surface protein, or may replace amino acid residues which have been removed from the viral surface protein.

One of the most frequently used delivery systems for achieving gene therapy involves viral vectors, most commonly adenoviral and retroviral vectors. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

For gene delivery purposes, a viral particle can be developed from a virus that is native to a target cell or from a virus that is non-native to a target cell. In general, it is desirable to use a non-native virus vector rather than a native virus vector. While native virus vectors may possess a natural affinity for target cells, such viruses pose a greater hazard since they possess a greater potential for propagation in target cells. In this regard, animal virus vectors, wherein they are not naturally designed for propagation in human cells, can be useful for gene delivery to human cells. In order to obtain sufficient yields of such animal virus vectors for use in gene delivery, however, it is necessary to carry out production in a native animal packaging cell. Virus vectors produced in this way, however, normally lack any components either as part of the envelope or as part of the capsid that can provide tropism for human cells. For example, current practices for the production of non-human virus vectors, such as ecotropic mouse (murine) retroviruses like MMLV, are produced in a mouse packaging cell line. Another component required for human cell tropism must be provided.

In general, the propagation of a viral vector (without a helper virus) proceeds in a packaging cell in which a nucleic acid sequence for packaging components were stably integrated into the cellular genome and nucleic acid coding for viral nucleic acid is introduced in such a cell line. Packaging lines currently available yield producer clones of sufficient titer to transduce human cells for gene therapy applications and have led to the initiation of human clinical trials. However, there are two areas in which these lines are deficient.

First, design of the appropriate retroviral vectors for particular applications requires the construction and testing of several vector configurations. For example, Belmont et al., Molec. and Cell. Biol. 8(12):5116-5125 (1988), constructed stable producer lines from 16 retroviral vectors in order to identify the vector capable of producing both the highest titer producer and giving optimal expression. Some of the configurations examined included: (1) LTR driven expression vs. an internal promoter; (2) selection of an internal promoter derived from a viral or a cellular gene; and (3) whether a selectable marker was incorporated in the construct. A packaging system that would enable rapid, high-titer virus production without the need to generate stable producer lines would be highly advantageous in that it would save approximately two months required for the identification of high titer producer clones derived from several constructs.

Second, compared to NIH 3T3 cells, the infection efficiency of primary cultures of mammalian somatic cells with a high titer amphotropic retrovirus producer varies considerably. The transduction efficiency of mouse myoblasts (Dhawan et al., Science 254:1509-1512 (1991) or rat capillary endothelial cells (Yao et. al., Proc. Natl. Acad. Sci. USA 88:8101-8105 (1991)) was shown to be approximately equal to that of NIH 3T3 cells, whereas the transduction efficiency of canine hepatocytes (Armentano et. al., Proc. Natl. Acad. Sci. USA 87:6141-6145 (1990)) was only 25% of that found in NIH 3T3 cells. Primary human tumor-infiltrating lymphocytes ("TILs"), human CD4+ and CD8+ T cells isolated from peripheral blood lymphocytes, and primate long-term reconstituting hematopoietic stem cells, represent an extreme example of low transduction efficiency compared to NIH 3T3 cells. Purified human CD4+ and CD8+ T Cells have been reported on one occasion to be infected to levels of 6%-9% with supernatants from stable producer clones (Morecki et al., Cancer Immunol. Immunother. 32:342-352 (1991)). If the retrovirus vector contains the neoR gene, populations that are highly enriched for transduced cells can be obtained by selection in G418. However, selectable marker expression has been shown to have deleterious effects on long-term gene expression in vivo in hematopoietic stem cells (Apperly et. al. Blood 78:310-317 (1991)).

To overcome these limitations, methods and compositions for novel transient transfection packaging systems are provided. Improvements in the retroviral vector design enables the following: (1) the replacement of cumbersome plasmid cloning and fusion procedures which represent the prior art, (2) the provision of a single straightforward plasmid construct which avoids undue fusions and mutations in the parent constructs, which would compromise the reagent in terms of gaining regulatory (i.e. FDA) approval, (3) the elimination of redundant, inoperative, and/or undesirable sequences in the resultant retroviral vector (4) greater flexibility in the selection and directional cloning of therapeutic gene constructs into the retroviral vector, (5) facilitation of the molecular cloning of various auxiliary domains within the retroviral vector, (6) the introduction of strategic modifications which demonstrably increase the performance of the parent plasmid in the context of vector producer cells, and thus, increasing the resulting potency of the retroviral vector product (7) significant reduction in the over-all size of the retroviral vector construct to the extent that plasmid production is increased from a "low copy, low yield" reagent in biologic fermentations to one of intermediate yield. Taken together, these modifications retain the virtues (in terms of vector safety, gene incorporation and gene expression) of retroviral vectors currently in use, while providing significant improvements in the construction, validation, manufacture, and performance of prospective retroviral vectors for human gene therapy. This represents the second component of TDS includes a high performance retroviral expression vector, designated the C-REX vector.

Transient transfection has numerous advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392-8396).

A high efficiency manufacturing process for large scale production of retroviral vector stock bearing cytocidal gene constructs with high bulk titer and biologic activity is provided. The manufacturing process describes the use of transiently transfected 293T producer cells; an engineered method of producer cell scale up; and a transient transfection procedure that generates retroviral vectors that retains cytocidal gene expression with high fidelity.

In another embodiment, a fully validated 293T (human embryonic kidney cells transformed with SV40 large T) master cell bank for clinical retroviral vector production is provided. Although 293T cells have generated small amounts of moderate to high titer vector stocks for laboratory use, these producer cells have not been shown previously to be useful for large scale production of clinical vector stocks. The U.S. FDA severely regulates and restricts the use of vectors that could transfer intact oncogenes in the clinical product. The manufacturing process incorporates a method of DNA degradation in the final steps of vector harvest and collection that does not result in any loss of vector potency. In another embodiment, a method for concentrating retroviral vector stocks for consistent generation of clinical vector products approaching 109 cfu/ml is provided. The final formulation of the clinical product consisting of a chemically defined serum-free solution for harvest, collection and storage of high titer clinical vector stocks.

In another embodiment, a method of collection of the clinical vector using a closed loop manifold system for maintenance of sterility, sampling of quality control specimens and facilitation of final fill, is provided. The closed-loop manifold assembly (see FIGS. 19A and 19B) is designed to meet the specifications required for collection of clinical product, i.e., maintenance of sterility during sampling, harvest, concentration and final fill, and is not available as a product for sale. The closed loop manifold assembly for harvest, concentration and storage of viral particles disclosed herein comprises a flexboy bag and manifold system made of Stedim 71 film; a 3 layer coextruded film consisting of a fluid contact layer of Ethyl Vinyl Acetate (EVA), a gas barrier of Ethyl Vinyl Alcohol (EVOH) and an outer layer of EVA. The total film thickness is 300 mm. EVA is an inert non-PVC-based film, which does not require the addition of plasticizers, thereby keeping extractables to a minimum. Stem has conducted extensive biocompatibility trials and has established a Drug Master File with the FDA for this product. The film and port tubes meet USP Class VI requirements. All bag customization takes place in Stedim's class 10,000-controlled manufacturing environment. The film, tubing and all components used are gamma compatible to 45 kGy. Gamma irradiation is performed at a minimum exposure of 25 kGy to a maximum of 45 kGy. Product certificates of conformance are provided from both Stedim and their contract sterilizers.

The clinical vector was stored in volumes of 150 ml in 500 ml cryobags at −80° C. The fully validated product exhibits a viral titer of 3×107 colony forming units (Units) per milliliter, a biologic potency of 65-70% growth inhibitory activity in human breast, colon and pancreatic cancer cells, a uniform particle size of ~100 nm with no viral aggregation, less than 550 bp residual DNA indicating absence of intact oncogenes, no detectable E1A or SV40 large T antigen, and no detectable replication competent retrovirus (RCR) in 5 passages on mus Dunni and human 293 cells. The product is sterile with an endotoxin level of <0.3 EU/ml, and the end of production cells are free of mycoplasma and other adventitious viruses.

Rexin-G produced using the new pB-RVE and pdnG1/UBER-REX plasmids was stored in volumes of 20-40 ml in 150 ml plastic cryobag at −70±10° C. The titers of the clinical lots ranged from 0.5 to 5.0×10e9 Units (U)/ml, and each lot was validated to be free of replication competent retrovirus (RCR), and of requisite purity, biological potency, sterility, and general safety for systemic use in humans.

The viral envelope includes a targeting ligand which include, but are not limited to, the arginine-glycine-aspartic acid, or RGD, sequence, which binds fibronectin, and a polypeptide having the sequence Gly-Gly-Trp-Ser-His-Trp (SEQ ID NO: 5), which also binds to fibronectin. In addition to the binding region, the targeting polypeptide may further include linker sequences of one or more amino acid residues, placed at the N-terminal and/or C-terminal of the binding region, whereby such linkers increase rotational flexibility and/or minimize steric hindrance of the modified envelope polypeptide. The polynucleotides may be constructed by genetic engineering techniques known to those skilled in the art.

Thus, a targeted delivery vector made in accordance with this invention contains associated therewith a ligand that facilitates the vector accumulation at a target site, i.e. a target-specific ligand. The ligand is a chemical moiety, such as a molecule, a functional group, or fragment thereof, which is specifically reactive with the target of choice while being less reactive with other targets thus giving the targeted delivery vector an advantage of transferring nucleic acids encoding therapeutic or diagnostic polypeptides, selectively into the cells in proximity to the target of choice. By being "reactive" it is meant having binding affinity to a cell or tissue, or being capable of internalizing into a cell wherein binding affinity is detectable by any means known in the art, for example, by any standard in vitro assay such as ELISA, flow cytometry, immunocytochemistry, surface plasmon resonance, etc. Usually a ligand binds to a particular molecular moiety—an epitope, such as a molecule, a functional group, or a molecular complex associated with a cell or tissue, forming a binding pair of two members. It is recognized that in a binding pair, any member may be a ligand, while the other being an epitope. Such binding pairs are known in the art. Exemplary binding pairs are antibody-antigen, hormone-receptor, enzyme-substrate, nutrient (e.g. vitamin)-transport protein, growth factor-growth factor receptor, carbohydrate-lectin, and two polynucleotides having complementary sequences. Fragments of the ligands are to be considered a ligand and may be used for the present invention so long as the fragment retains the ability to bind to the appropriate cell surface epitope. Preferably, the ligands are proteins and peptides comprising antigen-binding sequences of an immunoglobulin. More preferably, the ligands are antigen-binding antibody fragments lacking Fc sequences. Such preferred ligands are Fab fragments of an immunoglobulin, F(ab)2 fragments of immunoglobulin, Fv antibody fragments, or single-chain Fv antibody fragments. These fragments can be enzymatically derived or produced recombinantly. In their functional aspect, the ligands are preferably internalizable ligands, i.e. the ligands that are internalized by the cell of choice for example, by the process of endocytosis. Likewise, ligands with substitutions or other alterations, but which retain the epitope binding ability, may be used. The ligands are advantageously selected to recognize pathological cells, for example, malignant cells or infectious agents. Ligands that bind to exposed collagen, for example, can target the vector to an area of a subject that comprises malignant tissue. In general, cells that have metastasized to another area of a body do so by invading and disrupting healthy tissue. This invasion results in exposed collagen which can be targeted by the vectors provided herein.

An additional group of ligands that can be used to target a vector are those that form a binding pair with the tyrosine kinase growth factor receptors which are overexpressed on the cell surfaces in many tumors. Exemplary tyrosine kinase growth factors are VEGF receptor, FGF receptor, PDGF receptor, IGF receptor, EGF receptor, TGF-alpha receptor, TGF-beta receptor, HB-EGF receptor, ErbB2 receptor, ErbB3 receptor, and ErbB4 receptor. EGF receptor vIII and ErbB2 (HEr2) receptors are especially preferred in the context of cancer treatment using INSERTS as these receptors are more specific to malignant cells, while scarce on normal ones. Alternatively, the ligands are selected to recognize the cells in need of genetic correction, or genetic alteration by introduction of a beneficial gene, such as: liver cells, epithelial cells, endocrine cells in genetically deficient organisms, in vitro embryonic cells, germ cells, stem cells, reproductive cells, hybrid cells, plant cells, or any cells used in an industrial process.

The ligand may be expressed on the surface of a viral particle or attached to a non-viral particle by any suitable method available in the art. The attachment may be covalent or non-covalent, such as by adsorption or complex formation. The attachment preferably involves a lipophilic molecular moiety capable of conjugating to the ligand by forming a covalent or non-covalent bond, and referred to as an "anchor". An anchor has affinity to lipophilic environments such as lipid micelles, bilayers, and other condensed phases, and thereby attaches the ligand to a lipid-nucleic acid microparticle. Methods of the ligand attachment via a lipophilic anchor are known in the art. (see, for example, F. Schuber, "Chemistry of ligand-coupling to liposomes", in: Liposomes as Tools for Basic Research and Industry, ed. by J. R. Philippot and F. Schuber, CRC Press, Boca Raton, 1995, p. 21-37).

It is recognized that the targeted delivery vectors disclosed herein include viral and non-viral particles. Non-viral particles include encapsulated nucleoproteins, including wholly or partially assembled viral particles, in lipid bilayers. Methods for encapsulating viruses into lipid bilayers are known in the art. They include passive entrapment into lipid bilayer-enclosed vesicles (liposomes), and incubation of virions with liposomes (U.S. Pat. No. 5,962,429; Fasbender, et al., J. Biol. Chem. 272:6479-6489; Hodgson and Solaiman, Nature Biotechnology 14:339-342 (1996)). Without being limited by a theory, we assume that acidic proteins exposed on the surface of a virion provide an interface for complexation with the cationic lipid/cationic polymer component of the targeted delivery vector and serve as a "scaffold" for the bilayer formation by the neutral lipid component. Exemplary types of viruses are adenoviruses, retroviruses, herpesviruses, lentiviruses, and bacteriophages.

Non-viral delivery systems, such as microparticles or nanoparticles including, for example, cationic liposomes and polycations, provide alternative methods for delivery systems and are encompassed by the present disclosure.

Examples of non-viral delivery systems include, for example, Wheeler et al., U.S. Pat. Nos. 5,976,567 and 5,981, 501. These patents disclose preparation of serum-stable plasmid-lipid particles by contacting an aqueous solution of a plasmid with an organic solution containing cationic and non-cationic lipids. Thierry et al., U.S. Pat. No. 6,096,335 disclose preparing of a complex comprising a globally anionic biologically active substance, a cationic constituent, and an anionic constituent. Allen and Stuart, PCT/US98/ 12937 (WO 98/58630) disclose forming polynucleotide-cationic lipid particles in a lipid solvent suitable for solubilization of the cationic lipid, adding neutral vesicle-forming lipid to the solvent containing the particles, and evaporating the lipid solvent to form liposomes having the polynucleotide entrapped within. Allen and Stuart, U.S. Pat. No. 6,120,798, disclose forming polynucleotide-lipid microparticles by dissolving a polynucleotide in a first, e.g. aqueous, solvent, dissolving a lipid in a second, e.g. organic, solvent immiscible with said first solvent, adding a third solvent to effect formation of a single phase, and further adding an amount of the first and second solvents to effect formation of two liquid phases. Bally et al. U.S. Pat. No. 5,705,385, and Zhang et al. U.S. Pat. No. 6,110,745 disclose a method for preparing a lipid-nucleic acid particle by contacting a nucleic acid with a solution containing a non-cationic lipid and a cationic lipid to form a lipid-nucleic acid mixture. Maurer et al., PCT/CA00/00843 (WO 01/06574) disclose a method for preparing fully lipid-encapsulated therapeutic agent particles of a charged therapeutic agent including combining preformed lipid vesicles, a charged therapeutic agent, and a destabilizing agent to form a mixture thereof in a destabilizing solvent that destabilizes, but does not disrupt, the vesicles, and subsequently removing the destabilizing agent.

A Particle-Forming Component ("PFC") typically comprises a lipid, such as a cationic lipid, optionally in combination with a PFC other than a cationic lipid. A cationic lipid is a lipid whose molecule is capable of electrolytic dissociation producing net positive ionic charge in the range of pH from about 3 to about 10, preferably in the physiological pH range from about 4 to about 9. Such cationic lipids encompass, for example, cationic detergents such as cationic amphiphiles having a single hydrocarbon chain. Patent and scientific literature describes numerous cationic lipids having nucleic acid transfection-enhancing properties. These transfection-enhancing cationic lipids include, for example: 1,2-dioleyloxy-3-(N,N,N-trimethylammonio)propane chloride-, DOTMA (U.S. Pat. No. 4,897,355); DOSPA (see Hawley-Nelson, et al., Focus 15 (3):73 (1993)); N,N-distearyl-N,N-dimethyl-ammonium bromide, or DDAB (U.S. Pat. No. 5,279,833); 1,2-dioleoyloxy-3-(N,N,N-trimethylammonio) propane chloride-DOTAP (Stamatatos, et al., Biochemistry 27: 3917-3925 (1988)); glycerol based lipids (see Leventis, et al., Biochem. Biophys. Acta 1023:124 (1990); arginyl-PE (U.S. Pat. No. 5,980,935); lysinyl-PE (Puyal, et al. J. Biochem. 228:697 (1995)), lipopolyamines (U.S. Pat. No. 5,171, 678) and cholesterol based lipids (WO 93/05162, U.S. Pat. No. 5,283,185); CHIM (1-(3-cholesteryl)-oxycarbonyl-aminomethylimidazole); and the like. Cationic lipids for transfection are reviewed, for example, in: Behr, Bioconjugate Chemistry, 5:382-389 (1994). Preferable cationic lipids are DDAB, CHIM, or combinations thereof. Examples of cationic lipids that are cationic detergents include (C12-C18)-alkyl- and (C12-C18)-alkenyl-trimethylammonium salts, N-(C12-C18)-alkyl- and N-(C12-C18)-alkenyl-pyridinium salts, and the like.

The size of a targeted delivery vector formed in accordance with this invention is within the range of about 40 to about 1500 nm, preferably in the range of about 50-500 nm, and most preferably, in the range of about 20-150 nm. This size selection advantageously aids the targeted delivery vector, when it is administered to the body, to penetrate from the blood vessels into the diseased tissues such as malignant tumors, and transfer a therapeutic nucleic acid therein. It is also a characteristic and advantageous property of the targeted delivery vector that its size, as measured for example, by dynamic light scattering method, does not substantially increase in the presence of extracellular biological fluids such as in vitro cell culture media or blood plasma.

Alternatively, as described in Culver et al (1992) Science 256, 1550-1552, cells which produce retroviruses can be injected into a tumor. The retrovirus-producing cells so introduced are engineered to actively produce a targeted delivery vector, such as a viral vector particle, so that continuous productions of the vector occurred within the tumor mass in situ. Thus, proliferating tumor cells can be successfully transduced in vivo if mixed with retroviral vector-producing cells.

Methods of Treatment

The targeted vectors of the present invention can also be used as a part of a gene therapy protocol to deliver nucleic acids encoding a therapeutic agent, such a mutant cyclin-G polypeptide. Thus, another aspect of the invention features expression vectors for in vivo or in vitro transfection of a therapeutic agent to areas of a subject comprising cell types associated with metastasized neoplastic disorders. The targeted vectors provided herein are intended for use as vectors for gene therapy. The mutant cyclin-G polypeptide and nucleic acid molecules can be used to replace the corresponding gene in other targeted vectors. Alternatively, a targeted vector disclosed herein (e.g., one comprising a collagen binding domain) can contain nucleic acid encoding any therapeutically agent (e.g., thymidine kinase). Of interest are those therapeutic agents useful for treating neoplastic disorders.

The present studies provide data generated from in vivo human clinical trials. Nevertheless, additional toxicity and therapeutic efficacy of a targeted vectors disclosed herein can be determined by standard pharmaceutical procedures in cell cultures or experimental animals, e.g., for determining the $LDS_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Doses that exhibit large therapeutic indices are preferred. In the present invention, doses that would normally exhibit toxic side effects may be used because the delivery system is designed to target the site of treatment in order to minimize damage to untreated cells and reduce side effects.

The data obtained from human clinical trials (see below) prove that the targeted vector of the invention functions in vivo to inhibit the progression of a neoplastic disorder. The data in Table 1 provides a treatment regimen for administration of such a vector to a patient. In addition, data obtained from cell culture assays and animal studies using alternative forms of the targeted vector (e.g., alternative targeting mechanism or alternative therapeutic agent) can be used in formulating a range of dosage for use in humans. The dosage lies preferably within a range of circulating concentrations that include the ED50 with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the $IC_{50}$ (ie., the concentration of the test compound which achieves a half-maximal infection or a half-maximal inhibition) as determined in cell culture. Such information can be used to more accurately determine useful doses in humans. Levels in plasma may be measured, for example, by high performance liquid chromatography.

Pharmaceutical compositions containing a targeted delivery vector can be formulated in any conventional manner by mixing an a selected amount of the vector with one or more physiologically acceptable carriers or excipients. For example, the targeted delivery vector may be suspended in a carrier such as PBS (phosphate buffered saline). The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

The targeted delivery vector and physiologically acceptable salts and solvates may be formulated for administration by inhalation or insufflation (either through the mouth or the nose) or for oral, buccal, parenteral or rectal administration. For administration by inhalation, the targeted delivery vector can be delivered in the form of an aerosol spray presentation from pressurized packs or a nebulizer, with the use of a suitable propellant, e.g. dichlorodifluoromethane, trichlorofluoromethane, dichlorotetra-fluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a therapeutic compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

The targeted delivery vector may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder lyophilized form for constitution with a suitable vehicle, e.g., sterile pyrogen-free water, before use.

In addition to the formulations described previously, the targeted delivery vector may also be formulated as a depot preparation. Such long acting formulations may be administered by implantation (for example, subcutaneously or intramuscularly) or by intramuscular injection. Thus, for example, the therapeutic compounds may be formulated with suitable polymeric or hydrophobic materials (for example as an emulsion in an acceptable oil) or ion exchange resins, or as sparingly soluble derivatives, for example, as a sparingly soluble salt.

The active agents may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%-10% isotonic solutions, pH about 5-7, with appropriate salts. The compounds may be formulated as aerosols for topical application, such as by inhalation.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension.

The compositions may, if desired, be presented in a pack or dispenser device which may contain one or more unit dosage forms containing the active ingredient. The pack may for example, comprise metal or plastic foil, such as a blister pack. The pack or dispenser device may be accompanied by instructions for administration.

The active agents may be packaged as articles of manufacture containing packaging material, an agent provided herein, and a label that indicates the disorder for which the agent is provided.

The targeted retroviral particle comprising the cytokine gene may be administered alone or in conjunction with other therapeutic treatments or active agents. For example, the targeted retroviral particle comprising a cytokine gene may be administered with the targeted retroviral particle comprising a cytocidal gene. The quantity of the targeted retroviral particle comprising a cytocidal gene to be administered is based on the titer of the virus particles as described herein above. By way of example, if the targeted retroviral particle comprising a cytokine gene is administered in conjunction with a targeted retroviral particle comprising a cytocidal gene the titer of the retroviral particle for each vector may be lower than if each vector is used alone. The targeted retroviral particle comprising the cytokine gene may be administered concurrently or separately from the targeted retroviral particle comprising the cytocidal gene.

The methods of the subject invention also relate to methods of treating cancer by administering a targeted retroviral particle (e.g., the targeted retroviral vector expressing a cytokine either alone or in conjunction with the targeted retroviral vector expressing a cytocidal gene) with one or more other active agents. Examples of other active agents that may be used include, but are not limited to, chemotherapeutic agents, anti-inflammatory agents, protease inhibitors, such as HIV protease inhibitors, nucleoside analogs, such as AZT. The one or more active agents may be administered concurrently or separately (e.g., before administration of the targeted retroviral particle or after administration of the targeted retroviral particle) with the one or more active agents. One of skill in the art will appreciate that the targeted retroviral particle may be administered either by the same route as the one or more agents (e.g., the targeted retroviral vector and the agent are both administered intravenously) or by different routes (e.g., the targeted retroviral vector is administered intravenously and the one or more agents are administered orally).

An effective amount or therapeutically effective of the targeted retroviral particles to be administered to a subject in need of treatment may be determined in a variety of ways. By way of example, the amount may be based on viral titer or efficacy in an animal model. Alternatively the dosing regimes used in clinical trials may be used as general guidelines. The daily dose may be administered in a single dose or in portions at various hours of the day. Initially, a higher dosage may be required and may be reduced over time when the optimal initial response is obtained. By way of example, treatment may be continuous for days, weeks, or years, or may be at intervals with intervening rest periods. The dosage may be modified in accordance with other treatments the individual may be receiving. However, the method of treatment is in no way limited to a particular concentration or range of the targeted retroviral particle and may be varied for each individual being treated and for each derivative used.

One of skill in the art will appreciate that individualization of dosage may be required to achieve the maximum effect for a given individual. It is further understood by one skilled in the art that the dosage administered to a individual being treated may vary depending on the individuals age, severity or stage of the disease and response to the course of treatment. One skilled in the art will know the clinical parameters to evaluate to determine proper dosage for the individual being treated by the methods described herein. Clinical parameters that may be assessed for determining dosage include, but are not limited to, tumor size, alteration in the level of tumor markers used in clinical testing for particular malignancies. Based on such parameters the treating physician will determine the therapeutically effective amount to be used for a given individual. Such therapies may be administered as often as necessary and for the period of time judged necessary by the treating physician.

In the present studies, exemplary protocols were designed for cancer patients. An intra-patient dose escalation regimen by intravenous infusion of Rexin-G was given daily for 8-10 days. Completion of this regimen was followed by a one-week rest period for assessment of toxicity; after which, the maximum tolerated dose of Rexin-G was administered IV for another 8-10 days. If the patient did not develop a grade 3 or 4 adverse event related to Rexin-G during the treatment periods, the dose of Rexin-G was escalated as follows:

TABLE 1

Treatment Regimen

| Treatment Day | Dose Level | Vector Dose/Day |
|---|---|---|
| Day 1-6 (Dose Escalation Regimen) | I | $4.5 \times 10^9$ Units |
| Day 7-8 | II | $9.0 \times 10^9$ Units |
| Day 9-10 | III | $1.4 \times 10^{10}$ Units |
| Day 18-27 (High Dose Regimen) | III | $1.4 \times 10^{10}$ Units |

Based on the observed safety in the first two patients, a third patient with Stage IVB pancreatic cancer with numerous liver metastases was given a frontline treatment with intravenous Rexin-G for six days, followed by 8 weekly doses of gemcitabine at 1000 mg/m² in a second clinical protocol approved by the Philippine BFAD.

The use of the improved pB-RVE and pdnG1/UBER-REX plasmids has allowed the production of a very high-potency preparation (1-5×10e9 U/ml) of Rexin-G™. This overcomes the problems of large infusion volume and resultant dosing limitations of the previous product and allows the development of strategic dose-dense regimens defined as the Calculus of Parity. In cancer therapy, a critical factor influencing the efficacy of an investigational agent is the extent of the tumor burden. Oftentimes, the margin of safety of a test drug is too narrow because dose-limiting toxicity is reached prior to gaining tumor control. Thus, the development of a cancer drug that can actually address the tumor burden without eliciting dose-limiting side effects or organ damage represents a significant milestone and advancement in cancer treatment. Another important problem is the natural kinetics of cancer growth, which requires an appropriate kinetic solution. Historic models of tumor growth are now considered overly simplistic (Heitjan. (1991) Stat. Med. 10:1075-1088, Norton. (2005) Oncologist 10:370-381), yet these simplistic models greatly influenced the development of standards of cancer treatment that are still enforced today; that is, to use drugs in combination, and to use them in equally spaced cycles of equal intensity. While the prediction that tumor shrinkage is correlated with improved prognosis is certainly true, the prediction that giving conventional drugs long enough would lead to tumor eradication, has turned out to be false (Norton. (2006) Oncol. 4:36-37) Appreciation of a more complex kinetics, as described by Benjamin Gompertz and formalized as the Norton-Simon model, takes into account the dynamics of metastasis and the quantitative relationship between tumor burden and metastatic potential in its predictions. Thus, the concept of dose-dense chemotherapies emerged, which emphasized the optimal doses of drugs that cause regression of the tumor over shorter time intervals and favored sequential rather than combinatorial approaches ((Norton. (2006) Oncol. 4:36-37; Fornier and Norton. (2005) Breast Cancer Res. 7: 64-69). Subsequently, a number of clinical trials provided supportive evidence that giving drugs more densely made a significant difference in terms of optimizing cancer cell kill.

The introduction of pathotropic nanoparticles for targeted gene delivery enables a new and quantitative approach to treating metastatic cancer in a unique and strategic manner. The Calculus of Parity described herein represents an emergent paradigm that seeks to meet and to match a given tumor burden in a highly compressed period of time; in other words, a Dose-Dense Induction Regimen based quantitatively on best estimates of total tumor burden. The Calculus of Parity assumes from the outset, (i) that the therapeutic agent (in this case Rexin-G™) is adequately targeted such that physiological barriers including dilution, turbulence, flow, diffusion barriers, filtration, inactivation, and clearance are sufficiently counteracted such that a physiological performance coefficient ($\phi$) or physiological multiplicity of infection (P-MOI) can be calculated, (ii) that the agent is effective at levels that do not confer restrictive dose-limiting toxicities, and (iii) that the agent is available in sufficiently high concentrations to allow for intravenous administration of the personalized doses without inducing volume overload. The physiological performance coefficient for cytocidal cyclin G1 constructs varies from 4 to 250, and depends in part on the titer of the drug (Gordon et al. (2000) Cancer Res. 60:3343-3347). To calculate the optimal dosage of Rexin-G™ to be given each day, the following factors were taken into consideration: (1) the total tumor burden based on radiologic imaging studies, (2) the physiological performance coefficient ($\phi$) of the system, which specifies the multiplicity of inducible gene transfer units needed per target cancer cell, and (3) the precise potency of the drug defined in terms of vector titer, which is expressed in colony forming units (U) per ml. One gene transfer unit is the equivalent of one colony forming unit. The Calculus of Parity predicts that tumor control can be achieved if the dose of the targeted vector administered is equivalent to the emergent tumor burden; yet the total dosage should be administered in as short a period of time as considered safely possible, in order to prevent catch-up tumor growth while allowing time for the reticuloendothelial system to eliminate the resulting tumor debris (Gordon et al. (2000) Cancer Res. 60:3343-3347).

The Calculus of Parity Equation:

$$\text{Dose of Gene Therapy Drug Needed for Initial Tumor Control} = \frac{\text{Tumor Burden} \times pMOI}{\text{Potency of Drug}}$$

The Calculus of Parity as Applied to Rexin-G Treatment

Where Tumor Burden is derived from the equation [the sum of the longest diameters (cm) of target lesions]×[1×10e9 cancer cells/cm]

$$\text{Number of Rexin-G bags needed} = \frac{\text{Volume of Rexin-G dose}}{\text{Volume per cryobag}}$$

With Rexin-G supplied as 40 ml alliquots the needed number of bags is $$\frac{1400 \text{ ml}}{40 \text{ ml}} = 35 \text{ cryobags}$$

Three dosing schedules for different tumor burden were derived using the Calculus of Parity (see above).

| Estimated Tumor Burden by Calculus of Parity | Initial/Induction (4 weeks) | Maintenance (6 months) |
|---|---|---|
| Small Tumor Burden (<5 × 10e9 cancer cells) | 4.0 × 10e10 Units per day, Mon-Fri with rest on week-ends × 4 weeks; 2 week rest period followed by tumor response evaluation by CT, MRI or PET scan | Repeat 2- to 4-week cycle Re-calculate parity to determine the cumulative dose to be given |
| Moderate Tumor Burden (5-10 × 10e9 cancer cells) | 8.0 × 10e10 Units per day, Mon-Fri with rest period on week-ends × 4 weeks; 2 week rest period followed by tumor response evaluation by CT, MRI or PET scan | Repeat 2- to 4-week cycle Re-calculate parity to determine the cumulative dose to be given |
| Large Tumor Burden (>10 × 10e9 cancer cells) | 1.2 × 10e11 Units per day, Mon-Fri with rest period on week-ends × 4 weeks; or 2.0 × 10e11 Units per day M-W-F for 4 weeks; 2 week rest period followed by tumor response evaluation by CT, MRI or PET scan | Repeat 2- to 4-week cycle Re-calculate parity to determine the cumulative dose to be given |

Where $\phi$ or pMOI is an empiric number estimated from preclinical and clinical studies For Rexin-G pMOI is 100

Where Potency is the number of colony forming units (U) per ml of drug solution.

For Rexin-G produced using the new constructs, pB-RVE and pdnG1/EREX, Potency ranges from 5×10e8 to 5×10e9 Units/ml Example: Rexin-G Dose Calculation for a Patient with Metastatic Pancreatic Cancer Where patient has a locally advanced tumor of dimensions of 2 cm×2 cm and 4 liver lesions, three of which measure 1 cm×1 cm, and the fourth measures 2 cm×2 cm Tumor Burden (pancreas, liver)=(4 cm+(2 cm+2 cm+2 cm+4 cm))×1×10e9 cells/cm=14×10e9 cancer cells Where the specific lot of Rexin-G has Potency of 1×10e9 U/ml $$\text{Rexin-G Dose (ml)} = \frac{14 \times 10e9 \text{ cells} \times 100 \text{ U/cell}}{1 \times 10e9 \text{ U/ml}} = \frac{14 \times 10e11 \text{ U} = 1400 \text{ ml}}{1 \times 10e9 \text{ U/ml}}$$

Example: Calculation of the Number of Rexin-G Cryobags to Administer

To determine the number of Rexin-G cryobags needed for infusion, the total volume of the Rexin-G dose is divided by the standard volume of Rexin-G contained in a cryobag from the lot used. Rexin-G is supplied in cryobags in either 20 ml or 40 ml aliquots.

Our preliminary clinical experience with this calculus (see Study C) is limited to three patients, each with relatively large tumor burdens; however, the dramatic responses observed in two patients who failed standard chemotherapy and in one patient who refused standard chemotherapy (100% response rate) underscores both the potential utility and the urgent need for further studies of the quantitative approach.

The advent of targeted therapies, including targeted gene therapy, is changing the way tumor responses to a cancer drug are being evaluated. The guiding principle in cancer therapy has been that the therapeutic benefit gained from a prospective chemotherapeutic agent must outweigh the risk of serious or fatal systemic toxicity induced by the drug candidate. To this end, the Response Evaluation Criteria in Solid Tumors (RECIST) was developed by the National Cancer Institute (NCI), Bethesda Md., USA, and has been employed by most, if not all, academic institutions as the universal standard for tumor response evaluations (Therasse et al., (2000) J. Nat'l. Cancer Inst. 92:205-216). Specifically, an objective tumor response (OTR) has, until recently, been considered the golden standard of success in evaluating cancer therapy for solid tumors. An OTR consists of at least a 30% reduction in the size of target lesions and/or complete disappearance of metastatic foci or non-target lesions. However, many biologic response modifiers of cancer are, in fact, not associated with tumor shrinkage, but have been shown to prolong progression-free survival (PFS), and overall survival (OS) (Abeloff, (2006) Oncol. News Int'l. 15:2-16). Hence, the response to effective biologic agents is often physiologic and RECIST may no longer be the appropriate standard for evaluation of tumor response to biologic therapies. Thus, alternative surrogate endpoints such as measurements of tumor density (an index of necrosis), blood flow and glucose utilization in tumors, and other refinements of imaging methods used to evaluate the mechanisms of tumor response are called for.

Understanding the disease process, as well as the intended mechanisms of action of the proposed intervention, is, therefore, critical in predicting the effect of the treatment on a given clinical endpoint. In the case of tumor responses to Rexin-G™, wherein the primary mechanism of action is the induction of apoptosis in proliferative tumor cells and attendant angiogenic vasculature, necrosis and cystic changes within the tumor often occur. This is due to the targeted disruption of a tumor's blood supply which starves the tumor, resulting in subsequent necrosis within the tumor. In tumors of Rexin-G™-treated patients, wherein apoptosis is a predominant feature, the tumors simply shrink and disappear in follow-up imaging studies. However, in tumors wherein necrosis is a prominent feature, the size of the tumors may actually become larger after Rexin-G™ treatment, due to the inflammatory reaction evoked by the necrotic tumor and cystic conversion of the tumor. In this case, an increase in the size of tumor nodules on CT scan, PET scan or MRI does not necessarily indicate disease progression. Therefore, additional concomitant evaluations that reflect the histological quality of the treated tumors are needed to more accurately determine the extent of necrosis or cystic changes induced by Rexin-G treatment. For CT scans tumor density measurement in Hounsfield Units (HU) is an accurate and reproducible index of the extent of tumor necrosis. A progressive reduction in the density of target lesions (decrease in HU) indicates a positive treatment effect. For PET scans a progressive reduction in standard uptake value (SUV) in target lesions indicates decreased tumor activity and positive treatment effect. For biopsied tumor the presence of apoptosis, necrosis, reactive fibrosis and tumor infiltrating lymphocytes (TILs) indicate a positive treatment effect.

In the case of osteosarcoma, a favorable tumor response is indicated by tumor necrosis and increased calcification in lesions as evidenced by sequential CT scans and of decred glucose utilization in lesions as evidenced by progressive reduction in SUV of $^{18}$FDG on sequential PET scans. An observed calcification increase in a lesion of at least 10%, 25%, 50%, 100%, 200%, 300%, 400%, 500%, 600%, 700%, 800%, 900%, or 1000% is evidence of a positive tumorcydal response that can be used to assess treatment outcome and to plan further treatment courses. A reduction of $^{18}$FDG utilization by a lesion of at least 10%, 20%, 30%, 40%, 50%, 60%, 70%, 80%, 90%, or 95% is evidence of a positive tumorcydal response that can also be used to assess treatment outcome and to plan further treatment courses.

Progress in identifying dose limiting toxicities (DLT) and maximum tolerated dose (MTD) has been accelerated thorough clinical trials with an adaptive therapy design, whereby patients may be retreated with the same treatment cycle if clinical efficacy is observed and all treatment related toxicities resolve to ≤Grade 1. Alternatively, a patient may advance to the next higher dose level if no objective treatment response was noted, but all treatment related toxicities resolve to ≤Grade 1. Both mechanisms increase the chance of gaining tumor control without compromising patient safety and reduce the time and expense involved with patient recruitment.

To further promote tumor eradication and enhance cancer survival, an auxiliary gene transfer strategy specifically designed to localize at or near the site of disease with a tumor targeted cytocidal gene expression vector was developed. The localization at or near the site of disease with a tumor targeted expression vector bearing a cytokine gene can induce localized, but not systemic exposure to the expressed cytokine. Such localized cytokine induced immune responses will assist in acute tumor destruction and will also provide in situ cancer vaccination resulting in improved immune surveillance and reduced incidence of cancer recurrence. Such a tumor vaccination protocol may be helpful in targeting dormant shed and metastatic cancer cells, and also residual viable cancer cells in the primary tumor and tumor draining lymph nodes.

One cytokine gene under development for targeted delivery is granulocyte macrophage colony stimulating factor (GM-CSF) that when packaged in same pathotropic nanoparticle as Rexin-G, is called Reximmune-C. Other cytokines that can be used include TNF-alpha (Tumor necrosis factor alpha), Interferons including, but not limited to, IFN-alpha and IFN-gamma; and Interleukins including, but not limited to, Interleukin-1 (IL1), Interleukin-Beta (IL-beta), Interleukin-2 (IL2), Interleukin-4 (IL4), Interleukin-5 (IL5), Interleukin-6 (IL6), Interleukin-8 (IL8), Interleukin-10 (IL10), Interleukin-12 (IL12), Interleukin-13 (IL13), Interleukin-14 (IL14), Interleukin-15 (IL15), Interleukin-16 (IL16), Interleukin-18 (IL18), Interleukin-23 (IL23), Interleukin-24 (IL24). Additionally, more than one cytokine gene can be delivered by the tumor targeted expression vector. For example, GM-CSF can be co-expressed with IL1.

Tumor targeted expression vectors bearing cytokine genes can be administered before, concurrently or after the administration of cytocidal pathotropic nanoparticles. It might be most favorable to withhold Reximmune-C administration until the patient has experienced significant tumor reduction (and life extension) with Rexin-G administered as a single agent or in combination therapy, and to rely on Reximmune-C largely to forestall recurrences. On the other hand, the synergy of Rexin-G and Reximmune-C may needed to address the tumor burden directly. In such cases, the histological evaluations of the desired endpoints at each point in time should be addressed with an increased sophistication of histological and radiographic evaluation criteria.

Cytocidal and cytokine gene expressing pathotropic nanoparticles can be administered multiple times in various orders. For example, cytocidal gene expressing pathotropic nanoparticles can be administered first followed by cytokine gene expressing pathotropic nanoparticles that are then followed by administration with cytocidal gene expressing pathotropic nanoparticles. Such combinations can be done as alternating individual administrations, alternating treatment cycles or combinations of thereof. The administration of Rexin-G first followed by Reximmune-C, followed by Rexin-G is known as the Tri-Rex protocol. In a breast cancer patient with widespread metastasis to lymph nodes, liver, lung and bone, the Tri-Rex protocol completely eradicated all cancer cells in a tumor biopsy. The cumulative doses were 6×10e11 cfu for the first Rexin-G treatment cycle, 1×10e10 cfu for the Reximmune-C treatment cycle and 4×10e11 cfu for the second Rexin-G treatment cycle. This treatment protocol resulted in a fully necrotic tumor nodule with extensive areas of necrosis and significant infiltrations of host mononuclear cells with little if any flagrant tumor cells remaining. The immune cell infiltrate revealed an extensive complement of CD35+ dendritic cells, CD8+ killer T cells, and CD138+ plasma B cells providing evidence of active in situ immunization.

Flexible treatment plans using combined treatment schedules of cytocidal and cytokine gene expressing pathotropic nanoparticles can be designed to take into account observed clinical, radiologic, histopathological, immunohisochemistry, and clinical chemistry results. For example, if one does not see an objective, meaningful tumor response using one, several or all of these different measurement criteria, another treatment cycle using a higher cytocidal gene expressing pathotropic nanoparticles cumulative dose, but the same cumulative dose cytokine gene expressing pathotropic nanoparticles can be initiated if the physician believes that a higher cumulative dose of the cytocidal gene expressing pathotropic nanoparticles is needed to adequately expose tumor antigens to activated immune cells.

Histopathological indications to measure the efficacy of an individual administration, multiple administrations, or a treatment cycle a cytocidal gene expressing pathotropic nanoparticles with or without the administration of cytokine gene expressing pathotropic nanoparticles include focal areas of overt anti-angiogenesis associated with degerating tumor cells, large areas of necrosis and reactive fibrosis, and positive TUNEL staining for apoptotic structures. Immunohistochemical indications of efficacy include the appearance of tumor infiltrating lymphocytes such as $CD4^+$ ($T_h$), $CD8^+$ ($T_c$), $CD68^+$ (macrophage), $CD138^+$ (plasma B cell), $CD35^+$ (dendritic), $CD20^+$ (B cell), and $CD45^+$ (monocyte-macrophage) cells. The identification of cells positive for cytokine transgene expression such as for GM-CSF, is also a sign of efficacy.

Clinical chemistry results include observed reductions in soluble, secreted, or shed tumor markers/antigens such as a reduction in the serum level of prostate specific antigen (PSA) or HER2/neu shed antigen.

Samples sources for histopathological and immunohistochemical evaluation include tumor, lymph node and organ biopsies or needle biopsies and resected tumors, lymph nodes or organs.

Greater control of cytokine expression can be achieved through the incorporation of a suicide gene into the construct so that a clinical off switch would be available through the use of an oral pro-drug such as ganciclovir or the like, that would immediately ablate the entire population of cytokine transgene secreting tumor cells. A second generation version of Reximmune-C, called Reximmune-C-TNT that includes the herpes simplex virus (HSV) thymidine kinase gene was recently created to meet this goal. Pretreatment with a therapeutic viral particle like Rexin-G can also be used to reduce tumor volume and viablility prior to surgery. This would be particularly beneficial in converting previously unresectable tumors into ones that can be surgically removed and also reducing the incidence of shed, viable cancer cells into the surgical margins.

In patients with a familia history of cancer or with known genetic abnormalities/mutations such as a mutant BRAC1 gene that increases the risk for developing cancer, prophylactic treatment with the Rexin-G, Reximmune-C, or a combination of the two can be used to prevent the occurrence of overt disease. This can happen by destroying microscopic clusters of cancer cells that have started the recruitment of the neovasculature they needed to continue to grow in size, or by educating the immune system by attracting lymphocytes to microscopic clusters of cancer cells, or by a combination of the two.

The administration of retroviral vectors may elicite the production of vector neutralizing antibodies in the recipient, thereby hampering further treatment. (Halbert et al. (2006) Hum. Gene Ther. 17 (4):440-447) It is known, however, in the art, that the induction of neutralizing antibody production can be blocked by the immunosuppressive treatment given around the time of vector administration. Such immunosuppressive treatments include drugs (cyclophosphamide, FK506), cytokines (interferon-gamma, interleukin-12) and monoclonal antibodies (anti-CD4, anti-pgp39, CTLA4-Ig) (Potter and Chang, (1999) Ann. N.Y. Acad. Sci. 875:159-174) Furthermore, neutralizing antibodies may be removed by extracorporeal immunoadsorption (Nilsson et al. (1990) Clin. Exp. Immunol. 82 (3)440-444). Neutralizing antibodies can also be depleted in vivo by the administration of larger doses of vector. The Rexin-G vector has low immunogenicity and to date, vector neutralizing antibodies have not been detected in the serum of patients over a 6 month follow-up period.

Kits

Also provided are kits or drug delivery systems comprising the compositions for use in the methods described herein. All the essential materials and reagents required for administration of the targeted retroviral particle may be assembled in a kit (e.g., packaging cell construct or cell line, cytokine expression vector). The components of the kit may be provided in a variety of formulations as described above. The one or more targeted retroviral particle may be formulated with one or more agents (e.g., a chemotherapeutic agent) into a single pharmaceutically acceptable composition or separate pharmaceutically acceptable compositions.

The components of these kits or drug delivery systems may also be provided in dried or lyophilized forms. When reagents or components are provided as a dried form, reconstitution generally is by the addition of a suitable solvent, which may also be provided in another container means. The kits of the invention may also comprise instructions regarding the dosage and or administration information for the targeted retroviral particle. The kits or drug delivery systems of the present invention also will typically include a means for containing the vials in close confinement for commercial sale such as, e.g., injection or blow-molded plastic containers into which the desired vials are retained. Irrespective of the number or type of containers, the kits may also comprise, or be packaged with, an instrument for assisting with the injection/administration or placement of the ultimate complex composition within the body of a subject. Such an instrument may be an applicator, inhalant, syringe, pipette, forceps, measured spoon, eye dropper or any such medically approved delivery vehicle.

In another embodiment, a method for conducting a gene therapy business is provided. The method includes generating targeted delivery vectors and establishing a bank of vectors by harvesting and suspending the vector particles in a solution of suitable medium and storing the suspension. The method further includes providing the particles, and instructions for use of the particles, to a physician or health care provider for administration to a subject (patient) in need thereof. Such instructions for use of the vector can include the exemplary treatment regimen provided in Table 1. The method optionally includes billing the patient or the patient's insurance provider.

In yet another embodiment, a method for conducting a gene therapy business, including providing kits disclosed herein to a physician or health care provider, is provided The following examples are included for illustrative purposes only and are not intended to limit the scope of the invention. The specific methods exemplified can be practiced with other species. The examples are intended to exemplify generic processes.

EXAMPLES

Pancreatic cancer is the fourth leading cause of cancer death in the United States, and is the deadliest of all cancers. Complete surgical resection of the pancreatic tumor offers the only effective treatment for this disease. Unfortunately, such "curative" operations are only possible in 10 to 15% of patients with pancreatic cancer, typically those individuals in whom jaundice is the presenting symptom. The median survival time for patients with non-resectable pancreatic cancer is 3-6 months. Hence, the management of advanced pancreatic cancer is generally directed at palliation of symptoms. External beam radiation does not appear to prolong survival, although sufficient reduction in tumor size may lead to alleviation of pain. The addition of chemotherapy with fluorouracil (5-FU) to external beam radiation has increased the survival time for these patients (18). Recently, gemcitabine, a deoxycytidine analogue, has been shown to improve the quality of life of patients with advanced pancreatic cancer, although the duration of survival is extended by only 8-10 weeks.

Surgical resection is also the primary treatment modality for patients with colorectal cancer, which is the second leading cause of cancer death in the United States. Additional chemotherapy and radiation treatments have helped to reduce the recurrence of colorectal cancer in patients with early-stage disease (7). However, the effect of these treatments on locally advanced tumors has been less satisfactory (8). Currently, the 5-year survival rate for colorectal cancer patients treated with surgical resection is approximately 90% for stage I, 70% for stage II, 50% for stage III, and less than 5% for stage IV. While chemotherapy for colon cancer remains a useful palliative option, which may, at times, even extend to down-staging, the majority of patients with colon cancer exhaust the benefits from standard treatment within 18 months. Moreover, there appears to be a consensus among leading clinical oncologists that targeted "biologic therapies" hold the greatest promise in terms of future clinical development for both pancreatic and colon cancer.

Example 1

Constructs

The plasmid pBvl/CAEP contains coding sequences of the 4070A amphotropic envelope protein (GenBank accession number: M33469), that have been modified to incorporate an integral gain of collagen-binding function (Hall et al., Human Gene Therapy, 8:2183-2192, 1997). The parent expression plasmid, pCAE (Morgan et al., Journal of Virology, 67:4712-4721, 1967) was provided by the USC Gene Therapy Laboratories. This pCAE plasmid was modified by insertion of a Pst I site (gct gca gga, encoding the amino acids AAG) near the N-terminus of the mature protein between the coding sequences of amino acids 6 and 7 (pCAEP). A synthetic oligonucleotide duplex (gga cat gta gga tgg aga gaa cca tca ttc atg gct ctg tca gct gca (SEQ ID NO: 6), encoding the amino acids GHVGWREPSFMALSAA (SEQ ID NO: 9), a minimal collagen-binding decapeptide (in bold) derived from the D2 domain of bovine von Willebrand Factor (Hall et al., Human Gene Therapy, 11:983-993, 2000) and flanked by strategic linkers (underlined), was cloned into this unique Pst I site to produce pBvl/CAEP.

The expression of the chimeric envelope protein in 293T producer cells is driven by the strong CMV i.e. promoter. The chimeric envelope is processed correctly and incorporated stably into retroviral particles, which exhibit the gain-of-function phenotype without appreciable loss of infectious titer. Correct orientation of the collagen-binding domain was confirmed by DNA sequence analysis, and plasmid quality control was confirmed by restriction digestion Pst I, which linearizes the plasmid and releases the collagen-binding domain.

Further improvements to the original plasmid pBv1/CAEP were made to reduce the potential to generate replication-competent retrovirus (RCR) during Rexin-G™ production. The vector pBvl/CAEP contains 38 base pairs of untranslated sequences upstream of the Moloney Envelope ATG start codon. This vector also contains 76 base pairs of untranslated sequences downstream of the Moloney Envelope stop codon. Both of these untranslated sequences (38+76=114 base pairs) were eliminated by using the polymerase chain reaction technique to amplify only the Moloney Envelope open reading frame sequences from the ATG start codon to the TGA stop codon. The following sets of primers were used:

```
NewEnvF1    5' ATGCGGCCGCCCACC    GCGCGTTCAACGCTCTCAAAACCCCCTCAAGATA
            (SEQ ID NO: 7); and NewEnvR1    5' CCTCTAGATTA    TGGCTCGTACTCTATGGGTTTTAGCTGG
            (SEQ ID NO: 8).
``` pBV1/CAEP was used as the template for the PCR reaction to insure that the unique von Willebrand collagen binding site (GHVGWREPSFMALSAA; SEQ ID NO: 1) would be properly copied into the new open reading frame only Envelope PCR product. The proper 2037 bp pair PCR product was produced and ligated into a pCR2 cloning vector and sequenced to insure 100% sequence conformity to expected sequence. This properly sequenced Moloney Envelope open reading frame only gene was excised from the pCR2 plasmid backbone and subcloned into the ultra high expression plasmid pHCMV form Genelantis (formerly Gene Therapy Systems) to produce the new plasmid, pB-RVE.

This plasmid was tested in a number of different titer assays and found to its strength had increased such that it was now optimal to use 3-5 times less of it by quantity in a transfection in to 293T cells along with pCgpn and pE-REX to achieve similar titers. This implies that the pB-RVE plasmid is 3-5 times stronger than the corresponding pBV1/CAEP plasmid in producing functional envelope protein. However, if the same amount of pB-RVE plasmid is used as the normal amount pBV1/CAEP, far less titer would be produced. This result stresses the importance of conducting a complete set of plasmid ratio studies to obtain the optimal ratio for highest titer. In some circumstances, over expression of any one of the three plasmid component genes can disrupt a delicate balance of viral parts during assembly and processing and can cause inhibitory effects as noted in lower titers. We chose to use 3-5 times less pB-RVE than pBV1/CAEP to achieve a similar high titer and gain the advantage with this plasmid of using that much less of it during GMP retroviral production. This high level expression effect is most like due to the fact that the Envelope gene is expressed from a CMV promoter enhancer in tandem with a CMV Intron. The combination is advertised to be 3-5 times stronger than if just expressed from a CMV promoter as is the case for the pBV1/CAEP plasmid.

The plasmid pCgpn contains the MoMuLV gag-pol coding sequences (GenBank Accession number 331934), initially derived from proviral clone 3PO as pGag-pol-gpt, (Markowitz et al., Journal of Virology, 62:1120-1124, 1988) exhibiting a 134-base-pair deletion of the Ψ packaging signal and a truncation of env coding sequences. The construct was provided as an EcoRI fragment in pCgp in which the 5' EcoRI site corresponds to the XmaIII site upstream of Gag and the 3' EcoRI site was added adjacent to the ScaI site in env. The EcoRI fragment was excised from pCgp and ligated into the pcDNA3.1+ expression vector (Invitrogen) at the unique EcoRI cloning site.

Correct orientation was confirmed by restriction digestion with SalI and the insert was further characterized by digestion with EcoRI and HindIII. Both the 5' and 3' sequences of the gag-pol insert were confirmed by DNA sequence analysis utilizing the T7 promoter binding site primer (S1) and the pcDNA3.1/BGH reverse priming site (AS1), respectively. The resulting plasmid, designated pCgpn, encodes the gag-pol polyprotein driven by the strong CMV promoter and a neomycin resistance gene driven by the SV40 early promoter. The presence of an SV40 ori in this plasmid enables episomal replication in cell lines that express the SV40 large T antigen (i.e., 293T producer cells).

The following describes the construction of the plasmid bearing the pdnG1/C-REX retroviral expression vector which contains the dominant negative cyclin G1 construct (dnG1). The plasmid is enhanced for production of vectors of high infectious titer by transient transfection protocols. The cDNA sequences (472-1098 plus stop codon) encoding aa 41 to 249 of human cyclin G1 (CYCG1, Wu et al., Oncology Reports, 1:705-11, 1994; accession number U47413) were generated from a full length cyclin G1 template by PCR, incorporating Not I/Sal I overhangs. The N-terminal deletion mutant construct was cloned initially into a TA cloning vector (Invitrogen), followed by Not I/Sal I digestion and ligation of the purified insert into a Not I/Sal I digested pG1XSvNa retroviral expression vector (Genetic Therapy, Inc.) to produce the pdnG1SvNa vector complete with 5' and 3' long terminal repeat (LTR) sequences and a Ψ retroviral packaging sequence.

A CMV i.e. promoter-enhancer was prepared by PCR from a CMV-driven pIRES template (Clontech), incorporating Sac II overhangs, and cloned into the unique Sac II site of pdnG1SvNa upstream of the 5' LTR. The neomycin resistance gene, which facilitates determination of vector titer, is driven by the Sv40 e.p. with its nested ori. The inclusion of the strong CMV promoter, in addition to the Sv40 ori, facilitate high titer retroviral vector production in 293T cells expressing the large T antigen (Soneoka et al., Nucleic Acid Research, 23:628-633, 1995). Correct orientation and sequence of the CMV promoter was confirmed by restriction digestion and DNA sequence analysis, as was the dnG1 coding sequences. Plasmid identity and quality control is confirmed by digestion with Sac II (which releases the 750 bp CMV promoter) and Bgl II (which cuts at a unique site within the dnG1 construct).

Multiple GMP retroviral productions using pdnG1/C-REX and pBV1-CAEP have proven to be safe and RCR-free. The $4^{th}$ and $5^{th}$ generation MLV-based retroviral vectors and vector production methodologies; i.e., split genome designs, have yielded consistent production qualities without generating RCR under standard GMP conditions (Sheridan et al., 2000; Merten, 2004). However, we, as well as others have discerned that all available vector constructs contain a significant number of residual gag-pol sequences that potentially overlap with 5' DNA sequences contained in the respective gag-pol plasmid construct (Yu et al., 2000); and that these significant areas of overlap could become problematic when vector production is eventually scaled-up to commercial volumes with larger cell numbers and corresponding plasmid concentrations.

With these considerations in mind, we elected to remove 487 base pairs of residual gag-pol sequences from the parent pdnG1/C-REX vector by restriction digest and PCR cloning (pdnG1/C-ΔREX) followed by the insertion of a synthetic 97 bp envelop splice acceptor site (ESA) (Lazo et al., (1987) J. Virol. 61 (6): 2038-41) which served to offset detriments in terms of packaging (titer) and gene expression (potency). (FIG. 22). These resulting safety modifications of pdnG1/C-REX have resulted in the generation of pdnG1/UBER-REX, which encodes and expresses exactly the same transgenes (dnG1 and neo) without 487 base pairs of GAG, and which now replaces the former plasmid in the production of Rexin-G. A schematic comparison between the C-REX and C-REXII plasmids, and the UBER-REX plasmid is shown in FIG. 23.

The combination of the pB-RVE, pCgpn, pdnG1/UBER plasmids at exact ratios and under highly controlled and optimized manufacturing conditions yield a clinical vector product without RCR and the highest unconcentrated GMP final product retroviral titer ever reported, $>5 \times 10^9$ Cfu/mL.

Example 2

Rexin-G

The final product, Mx-dnG1 (REXIN-G™), is a matrix (collagen)-targeted retroviral vector encoding a N-terminal deletion mutant human cyclin G1 construct under the control of a hybrid LTR/CMV promoter. The vector also contains the neomycin resistance gene which is driven by the SV40 early promoter.

The Mx-dnG1 vector is produced by transient co-transfection with 3 plasmids of 293T (human embryonic kidney 293 cells transformed with SV40 large T antigen) cells obtained from a fully validated master cell bank.

The components of the transfection system includes the pdnG1/C-REX therapeutic plasmid construct which contains the deletion mutant of the human cyclin G1 gene encoding a.a. 41 to 249 driven by the CMV immediate early promoter, packaging sequences, and the bacterial neomycin resistance gene under the control of an internal SV40 early promoter. The truncated cyclin G1 gene was initially cloned into a TA cloning vector (Invitrogen), followed by Not I/Sal I digestion and ligation of the purified insert into a Not I/Sal I digested pG1XSvNa retroviral expression vector (provided by Genetic Therapy, Inc., Gaithersburg, Md.) to produce the pdnG1SvNa vector complete with 5' and 3' LTR sequences and a Ψ sequence. The CMV i.e. promoter-enhancer was prepared by PCR from a CMV-driven pIRES template (Clontech), incorporating Sac II overhangs, and cloned into the unique SacII site of pdnG1SvNa upstream of the 5'LTR.

The use of the plasmid, pdnG1/C-REX, was replaced by pdnG1/UBER-REX, a next generation plasmid that encodes and expresses exactly the same transgenes (dnG1 and neo) without 487 base pairs of GAG found in the original pdnG1/C-REX.

The system further includes the Mx (Bv1/pCAEP) envelope plasmid containing a CMV-driven modified amphotropic 4070A envelope protein wherein a collagen-binding peptide was inserted into an engineered Pst I site between a.a. 6 and 7 of the N terminal region of the 4070A envelope.

The use of the Mx (Bv1/pCAEP) envelope plasmid was replaced by pB-RVE, an improved plasmid that eliminates 114 bp of extraneous retroviral sequences that potentially overlap with native untranslated (UTR) sequences.

The system also includes the pCgpn plasmid which contains the MLV gag-pol elements driven by the CMV immediate early promoter. It is derived from clone 3PO as pGag-pol-gpt. The vector backbone is a pcDNA3.1+ from Invitrogen. Polyadnylation signal and transcription termination sequences from bovine growth hormone enhance RNA stability. An SV40 ori is featured along with the e.p. for episomal replication and vector rescue in cell lines expressing SV40 target T antigen.

The plasmids have been analyzed by restriction endonuclease digestion and the cell line consists of a DMEM base supplemented with 4 grams per liter glucose, 3 grams per liter sodium bicarbonate, and 10% gamma irradiated fetal bovine serum (Biowhittaker). The serum was obtained from USA sources, and has been tested free of bovine viruses in compliance with USDA regulations. The budding of the retroviral particles is enhanced by induction with sodium butyrate. The resulting viral particles are processed solely by passing the supernatant through a 0.45 micron filter or concentrated using a tangential flow/diafiltration method. The viral particles are Type C retrovirus in appearance. Retroviral particles will be harvested and suspended in a solution of 95% DMEM medium and 1.2% human serum albumin. This formulation is stored in aliquots of 150 ml in a 500 ml cryobag and kept frozen at −70 to −86° C. until used.

For Rexin-G™ produced with the improved pB-RVE and pdnG1/UBER-REX plasmids, the production, suspension, and collection of therapeutic nanoparticles are performed in the absence of bovine serum in a final formulation of proprietary medium, which is processed by sequential clarification, filtration and final fill into cryobags using a sterile closed loop system. The resulting C-type retroviral particles, with an average diameter of 100 nanometers, are devoid of all viral genes, and are fully replication defective. The titers of the clinical lots range from 3×10e7 to 5×10e9 colony forming units (U)/ml, and each lot is validated for requisite purity and biological potency.

Preparation of the Mx-dnG1 vector for patient administration consists of thawing the vector in the vector bag in a 37° C. 80% ethanol bath. Each vector bag will be thawed one hour prior to infusion into the patient, treated with Pulmozyme (10 U/ml), and immediately infused within 1-3 hours.

Processed clinical-grade Rexin-G™ produced with the improved pB-RVE and pdnG1/UBER-REX plasmids is sealed in cryobags that are stored in a −70±10° C. freezer prior to shipment. Each lot of validated and released cryobags containing the Rexin-G™ vector is shipped on dry ice to the Clinical Site where the vector is stored in a −70±10° C. freezer until used. Fifteen minutes before intravenous infusion, the vector is rapidly thawed in a 32-37° C. water bath and immediately infused or transported on ice in a dedicated tray or cooler to the patient's room or clinical site for immediate use. Patients receive the infusion of Rexin-G™ via a peripheral vein, a central IV line, or a hepatic artery. Various dosing regimens were used, as described in clinical studies A, B and C (below); however, a maximum volume of 8 ml/kg/dose is given once a day. Each bag of Rexin-G™ is infused over 10-30 minutes at a rate of 4 ml/min.

Example 3

Therapeutic Efficacy of the Mx-dnG1 Vector

The efficacy of Mx-dnG1 in inhibiting cancer cell proliferation in vitro, and in arresting tumor growth in vivo in a nude mouse model of liver metastasis, was tested. A human undifferentiated cancer cell line of pancreatic origin was selected as the prototype of metastatic cancer. Retroviral transduction efficiency in these cancer cells was excellent, ranging from 26% to 85%, depending on the multiplicity of infection (4 and 250 respectively). For selection of a therapeutic gene, cell proliferation studies were conducted in transduced cells using vectors bearing various cyclin G1 constructs. Under standard conditions, the Mx-dnG1 vector consistently exhibited the greatest anti-proliferative effect, concomitant with the appearance of immunoreactive cyclin G1 at the region of 20 kDa, representing the dnG1 protein. Based on these results, the Mx-dnG1 vector was selected for subsequent in vivo efficacy studies.

To assess the performance of Mx-dnG1 in vivo, a nude mouse model of liver metastasis was established by infusion of $7 \times 10^5$ human pancreatic cancer cells into the portal vein via an indwelling catheter that was kept in place for 14 days. Vector infusions were started three days later, consisting of 200 ml/day of either Mx-dnG1 (REXIN-G™; titer: $9.5 \times 10^8$ cfu/ml) or PBS saline control for a total of 9 days. The mice were sacrificed one day after completion of the vector infusions.

Histologic and immunocytochemical evaluation of metastatic tumor foci from mice treated with either PBS or low dose Mx-dnG1 was performed and evaluated with an Optimas imaging system. The human cyclin G1 protein was highly expressed in metastatic tumor foci, as evidenced by enhanced cyclin G1 nuclear immunoreactivity (brown-staining material) in the PBS-treated animals, and in the residual tumor foci of Mx-dnG1 vector-treated animals. Histologic examination of liver sections from control animals revealed substantial tumor foci with attendant areas of angiogenesis and stroma formation; the epithelial components stained positive for cytokeratin and associated tumor stromal/endothelial cells stained positive for vimentin and FLK receptor. In contrast, the mean size of tumor foci in the low dose Mx-dnG1-treated animals was significantly reduced compared to PBS controls (p=0.001), simultaneously revealing a focal increase in the density of apoptotic nuclei compared to the PBS control group. Further, infiltration by PAS+, CD68+ and hemosiderin-laden macrophages was observed in the residual tumor foci of Mx-dnG1-treated animals, suggesting active clearance of degenerating tumor cells and tumor debris by the hepatic reticuloendothelial system. Taken together, these findings demonstrate the anti-tumor efficacy in vivo of a targeted injectable retroviral vector bearing a cytocidal cell cycle control gene, and represent a definitive advance in the development of targeted injectable vectors for metastatic cancer.

In a subcutaneous human pancreatic cancer model in nude mice, we demonstrated that intravenous (IV) infusion of Mx-dnG1 enhanced gene delivery and arrested growth of subcutaneous tumors when compared to the non-targeted CAE-dnG1 vector (p=0.014), a control matrix-targeted vector bearing a marker gene (Mx-nBg; p=0.004) and PBS control (p=0.001). Enhanced vector penetration and transduction of tumor nodules (35.7+S.D. 1.4%) correlated with therapeutic efficacy without associated systemic toxicity. Kaplan-Meier survival studies were also conducted in mice treated with PBS placebo, the non-targeted CAE-dnG1 vector and Mx-dnG1 vector. Using the Tarone logrank test, the over-all p value for comparing all three groups simultaneously was 0.003, with a trend that was significant to a level of 0.004, indicating that the probability of long term control of tumor growth was significantly greater with targeted Mx-dnG1 vector than with the non-targeted CAE-dnG1 vector or PBS placebo. Taken together, the present study demonstrates that Mx-dnG1, deployed by peripheral vein injection (i) accumulated in angiogenic tumor vasculature within one hour, (ii) transduced tumor cells with high level efficiency, and (iii) enhanced therapeutic gene delivery and long term efficacy without eliciting appreciable toxicity.

Example 4

Pharmacology/Toxicology Studies

Matrix-targeted injectable retroviral vectors incorporating peptides that target extracellular matrix components (e.g. collagen) have been demonstrated to enhance therapeutic gene delivery in vivo. Additional data are presented using two mouse models of cancer and two matrix-targeted MLV-based retroviral vectors bearing a cytocidal/cytostatic dominant negative cyclin G1 construct (designated Mx-dnG1 and MxV-dnG1). Both Mx-dnG1 and MxV-dnG1 are amphotropic 4070A MLV-based retroviral vectors displaying a matrix (collagen)-targeting motif for targeting areas of pathology. The only difference between the two vectors is that MxV-dnG1 is pseudotyped with a vesicular stomatitis virus G protein.

In the subcutaneous human cancer xenograft model, $1\times10^7$ human MiaPaca2 pancreatic cancer cells (prototype for metastatic gastrointestinal cancer) were implanted subcutaneously into flank of nude mice. Six days later, 200 μl Mx-dnG1 vector was injected directly into the tail vein daily for one or two 10-day treatment cycles (Total vector dose: $5.6\times10^7$ [n=6] or $1.6\times10^8$ cfu [n=4] respectively). In the nude mouse model of liver metastasis, $7\times10^5$ MiaPaca2 cells were injected through the portal vein via an indwelling catheter which was kept in place for 10-14 days. 200 ml of MxV-dnG1 vector was infused over 10 min daily for 6 or 9 days (Total vector dose: $4.8\times10^6$ [n=3] or $1.1\times10^9$ cfu dose [n=4] respectively) starting three days after infusion of tumor cells. For biodistribution studies, a TaqMan™ based assay was developed to detect the G1XSvNa-based vector containing SV40 and Neomycin (Neo) gene sequences into mouse genomic DNA background (Althea Technologies, San Diego, Calif., USA). The assay detects a 95 nt amplicon (nts. 1779-1874 of the G1XSvNa plasmid vector) in which the fluorescently labeled probe overlaps the 3' portion of the SV40 gene and the 5' portion of the neomycin phosphotransferase resistance (Neor) gene.

There was no vector related mortality or morbidity observed with either the Mx-dnG1 or MxV-dnG1 vector. Low level positive signals were detected in the liver, lung and spleen of both low dose and high dose vector-treated animals. No PCR signal was detected in the testes, brain or heart of vector-treated animals. Histopathologic examination revealed portal vein phlebitis, pyelonephritis with focal myocarditis in two animals with indwelling catheters and no antibiotic prophylaxis. No other pathology was noted in non-target organs of Mx-dnG1- or MxV-dnG1-treated mice. Serum chemistry profiles revealed mild elevations in ALT and AST in the Mx-dnG1-treated animals compared to PBS controls. However, the levels were within normal limits for mice. No vector neutralizing antibodies were detected in the sera of vector-treated animals in a 7-week follow-up period.

The preclinical findings noted above confirm that intravenous infusion of Mx-dnG1 in two nude mouse models of human pancreatic cancer showed no appreciable damage to neighboring normal tissues nor systemic side effects. The method of targeted gene delivery via intravenous infusion offers several clinically relevant advantages. Infusion into the venous system will allow treatment of the tumor as well as occult foci of tumor. It is believed that the higher mitotic rate observed in dividing tumor cells will result in a higher transduction efficiency in tumors, while sparing hepatocytes and other normal tissues. Therefore, we propose a human clinical research protocol using intravenously administered Mx-dnG1 vector for the treatment of locally advanced or metastatic pancreatic cancer and other solid tumors refractory to standard chemotherapy.

Example 5

Clinical Studies

The objectives of the study were (1) to determine the dose-limiting toxicity and maximum tolerated dose (safety) of successive intravenous infusions of Rexin-G, and (2) to assess potential anti-tumor responses. The protocol was designed for end-stage cancer patients with an estimated survival time of at least 3 months. Three patients with Stage IV pancreatic cancer who were considered refractory to standard chemotherapy by their medical oncologists were invited to participate in the compassionate use protocol using Rexin-G as approved by the Philippine Bureau of Food and Drugs. An intrapatient dose escalation regimen by intravenous infusion of Rexin-G was given daily for 8-10 days. Completion of this regimen was followed by a one-week evaluation period for dose limiting toxicity; after which, the maximum tolerated dose of Rexin-G was administered for another 8-10 days. If the patient did not develop a grade 3 or 4 adverse event related to Rexin-G during the observation period, the dose of Rexin-G was escalated as shown in Table 1 (supra).

Tumor response was evaluated by serial determinations of the tumor volume using the formula: width$^2 \times$length$\times 0.52$ as measured by calipers, or by radiologic imaging (MRI or CT scan).

Patient #1, a 47 year-old Filipino female was diagnosed, by histologic examination of biopsied tumor tissue and staging studies, to have localized adenocarcinoma of the pancreatic head. She underwent a Whipples surgical procedure which included complete resection of the primary tumor. This was followed by single agent gemcitabine weekly for 7 doses, but chemotherapy was discontinued due to unacceptable toxicity. Several months later, a follow-up MRI showed recurrence of the primary tumor with metastatic spread to both the supraclavicular and abdominal lymph nodes. In compliance with the clinical protocol, the patient received two 10-day treatment cycles of Rexin-G for a cumulative dose of $2.1\times10e11$ Units over 28 days, with an interim rest period of one week. In the absence of systemic toxicity, the patient received an additional 10-day treatment cycle for a total cumulative dose of $3\times10e11$ Units.

The sizes of two superficial supraclavicular lymph nodes were measured manually using calipers. A progressive decrease in the tumor volumes of the supraclavicular lymph nodes was observed, reaching 33% and 62% reductions in tumor size, respectively, by the end of treatment cycle #2 on Day 28 (Table 2).

TABLE 2

Patient # 1 Caliper Measurements of Supraclavicular Lymph Nodes

| Date | Caliper Measurement cm | Tumor Volume* $cm^3$ | % Reduction in Size from Start of Rexin-G Rx |
|---|---|---|---|
| Day 1 | LN1 1.9 × 2.1 | 3.9 | |
| | LN2 1.5 × 1.8 | 2.1 | |
| Day 26 | LN1 1.8 × 1.8 | 3.0 | 23 |
| | LN2 1.3 × 1.3 | 1.1 | 48 |
| Day 27 | LN1 1.7 × 1.7 | 2.6 | 33 |
| | LN2 1.15 × 1.15 | 0.8 | 62 |

Figure 1C:
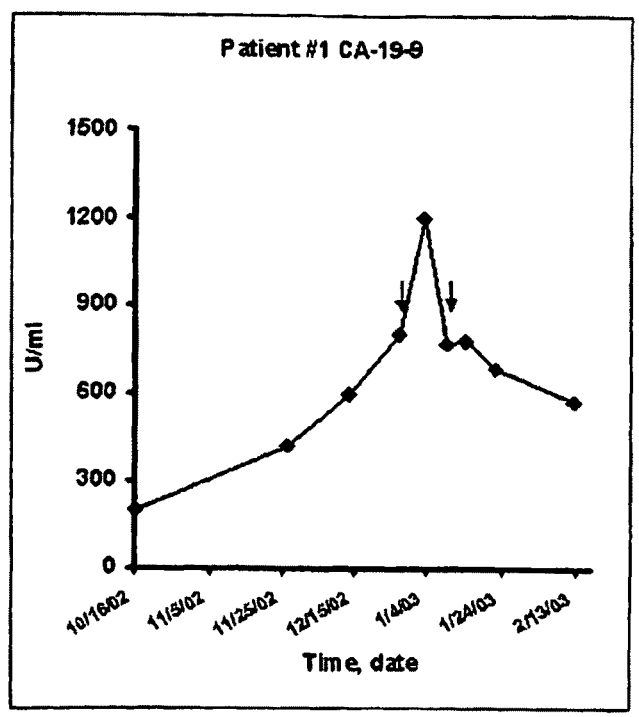
FIG. 1C is a graph showing that Rexin-G induces a reduction in CA19-9 serum level in Patient #1. Serum CA19-9 levels (U/ml), plotted on the vertical axis, are expressed as a function of time (date), plotted on the horizontal axis. The start of each treatment cycle is indicated by arrows.

Follow-up abdominal MRI revealed (i) no new areas of tumor metastasis, (ii) discernable areas of central necrosis, involving 40-50% of the primary tumor, and (iii) a significant decrease in the size of the para-aortic abdominal lymph node (FIG. 1A-B). On Day 54, a follow-up MRI showed no interval change in the size of the primary tumor. Consistent with these findings, a progressive decrease in CA19-9 serum levels (from a peak of 1200 to a low of 584 U/ml) were noted, amounting to a 50% reduction in CA19-9 levels on Day 54 (FIG. 1C). However, a follow-up CT scan on Day 101 showed a significant increase in the size of the primary tumor and the supraclavicular lymph nodes. The patient refused further chemotherapy until Day 175 when the patient agreed to receive weekly gemcitabine, 1000 mg/m2. By RECIST criteria, Patient #1 is alive with progressive disease on Day 189 follow-up, 6.75 months from the start of Rexin-G infusions, 11 months from the time of tumor recurrence, and 20 months from the time of initial diagnosis.

Figure 2C:
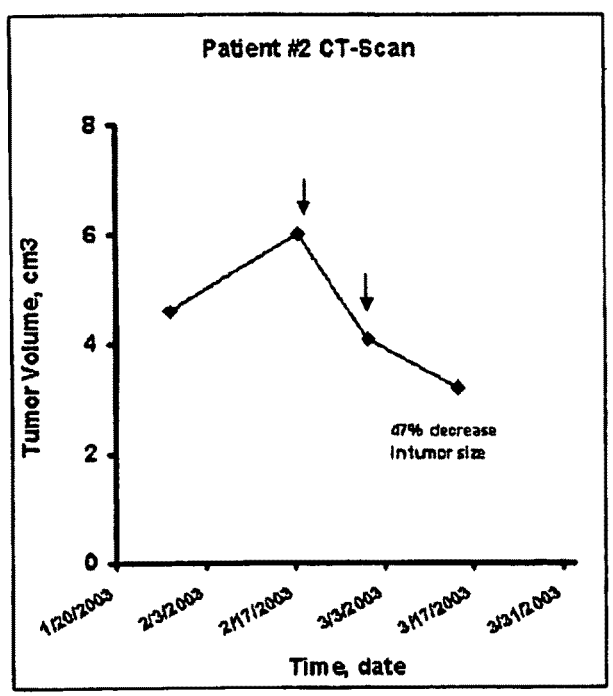
FIG. 2C is a graph showing that Rexin-G arrests primary tumor growth in Patient #2. A progressive decrease in tumor size was noted with successive treatment with Rexin-G. Tumor volume (cm$^3$) derived by using the formula: width$^2$×length×0.52 (O'Reilly et al. Cell 88, 277, 1997), and plotted on the vertical axis, is expressed as a function of time, plotted on the horizontal axis. The start of each treatment cycle is indicated by arrows.

Patient #2, a 56 year-old Filipino female was diagnosed to have Stage IVA locally advanced and non-resectable carcinoma of the pancreatic head, by cytologic examination of biliary brushings. Exploratory laparotomy revealed that the tumor was wrapped around the portal vein and encroached in close proximity to the superior mesenteric artery and vein. She had received external beam radiation therapy with 5-fluorouracil, and further received single agent gemcitabine weekly for 8 doses, followed by monthly maintenance doses. However, a progressive rise in CA19-9 serum levels was noted and a follow-up CT scan revealed that the tumor had increased in size (FIG. 2A). The patient received two treatment cycles of Rexin-G as daily intravenous infusions for a total cumulative dose of $1.8 \times 10^{11}$ Units. Results: Serial abdominal CT scans showed a significant decrease in tumor volume from 6.0 $cm^3$ at the beginning of Rexin-G infusions to 3.2 $cm^3$, at the end of the treatment, amounting to a 47% decrease in tumor size on Day 28 (FIG. 2A-C). Follow-up CT scan on Day 103 showed no interval change in the size of the tumor, after which the patient was maintained on monthly gemcitabine. By RECIST criteria, Patient #2 is alive, asymptomatic with stable disease on Day 154 follow-up, 5.5 months from the start of Rexin-G infusions, and 14 months after initial diagnosis.

Figure 3A:
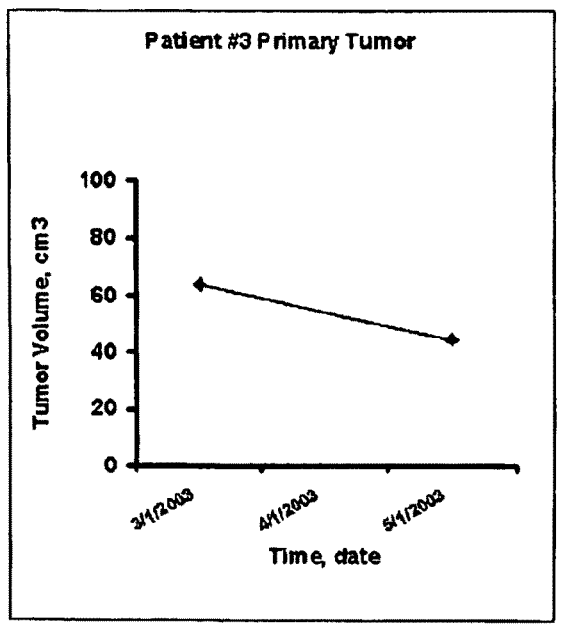
FIG. 3A depicts data indicating Rexin-G plus gemcitabine induces tumor regression in Patient #3 with metastatic pancreatic cancer. Tumor volumes (cm$^3$) of primary tumor is plotted on the Y axis and are expressed as a function of time, date. The start of Rexin-G infusions is indicated by arrows.
Figure 3B:
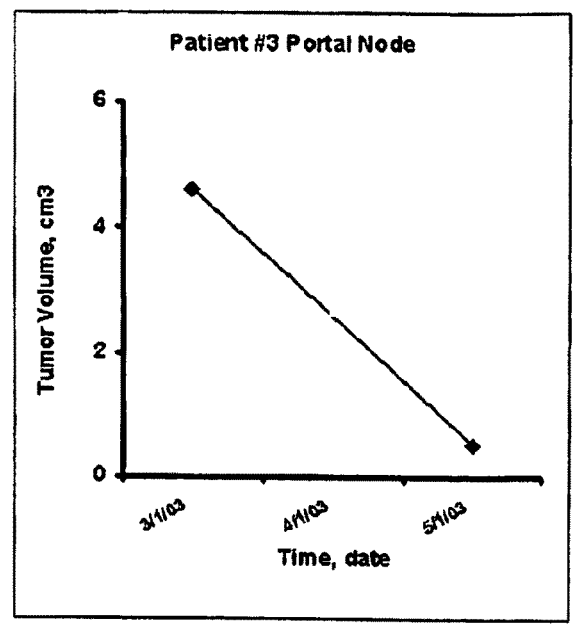
FIG. 3B depicts data indicating Rexin-G plus gemcitabine induces tumor regression in Patient #3 with metastatic pancreatic cancer. Tumor volume of portal node is plotted on the Y axis and are expressed as a function of time, date. The start of Rexin-G infusions is indicated by arrows.
Figure 3C:
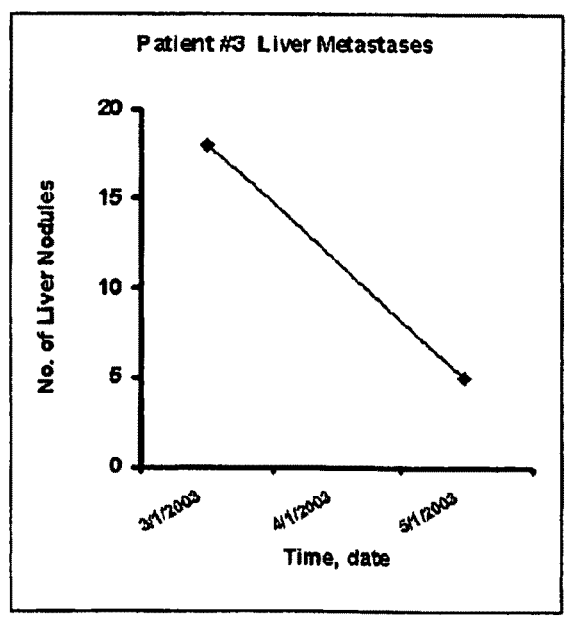
FIG. 3C depicts data indicating Rexin-G plus gemcitabine induces tumor regression in Patient #3 with metastatic pancreatic cancer. The number of liver nodules is plotted on the Y axis, are expressed as a function of time, date. The start of Rexin-G infusions is indicated by arrows.
Figure 4A:
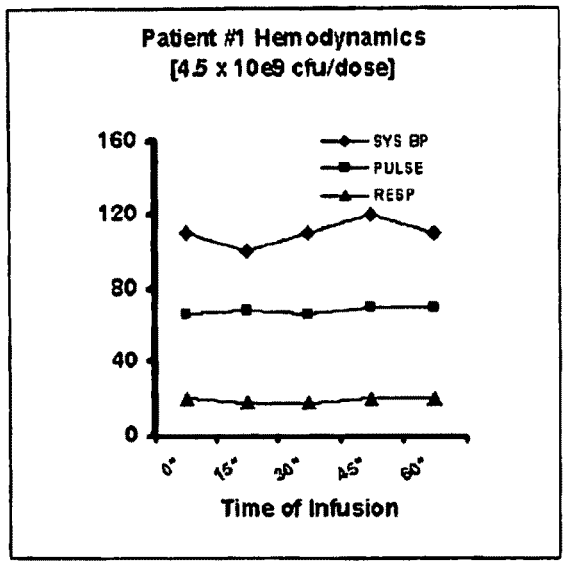
FIG. 4A the systolic blood pressure, expressed as mm Hg, plotted on the vertical axis, while time of REXIN-G infusion is plotted on the horizontal axis, for patient #1.
Figure 4B:
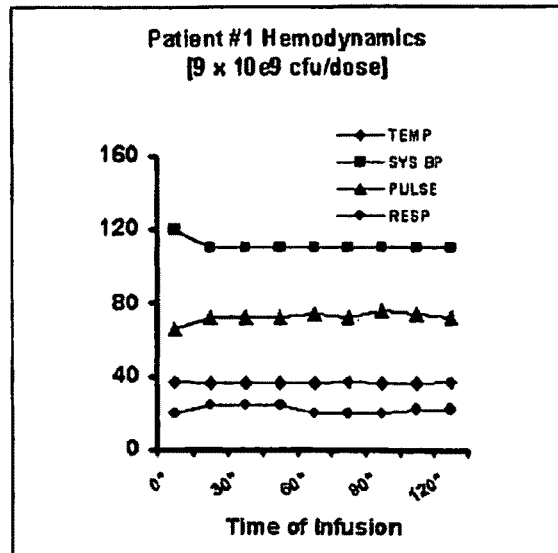
FIG. 4B pulse rate per minute plotted on the vertical axis, while time of REXIN-G infusion is plotted on the horizontal axis, for patient #1.
Figure 4C:
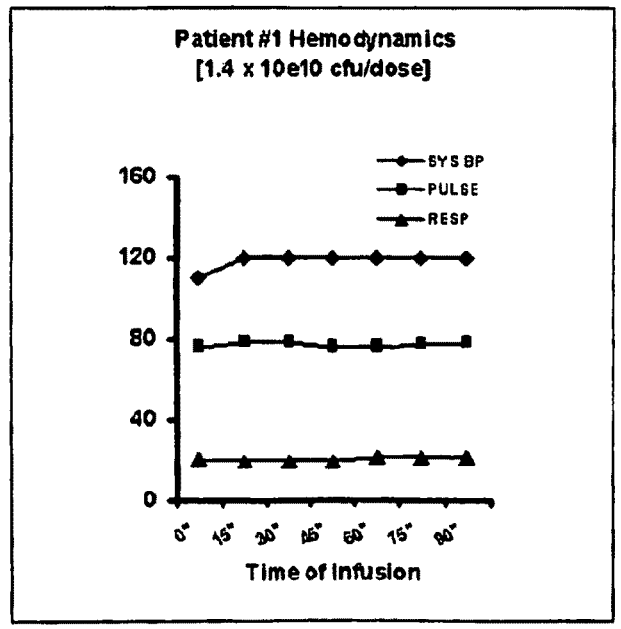
FIG. 4C respiratory rate per minute are plotted on the vertical axis, while time of REXIN-G infusion is plotted on the horizontal axis, for patient #1.
Figure 5A:
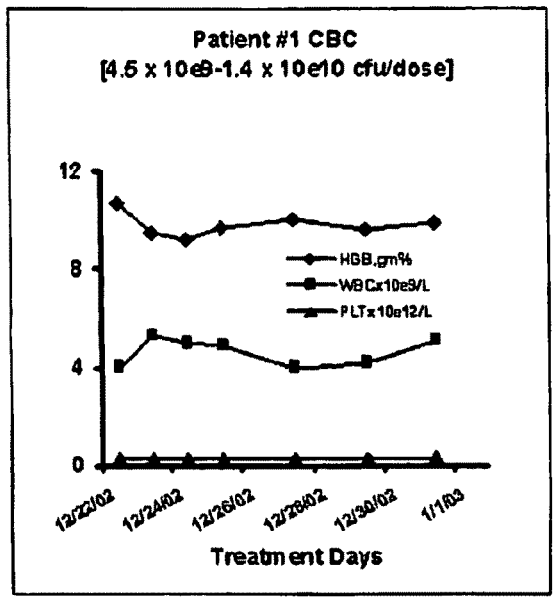
FIG. 5A depicts data indicating the hemoglobin (gms %), white blood count and platelet count for patient #1 plotted on the Y axis and expressed as a function of treatment days, plotted on the X axis.
Figure 5B:
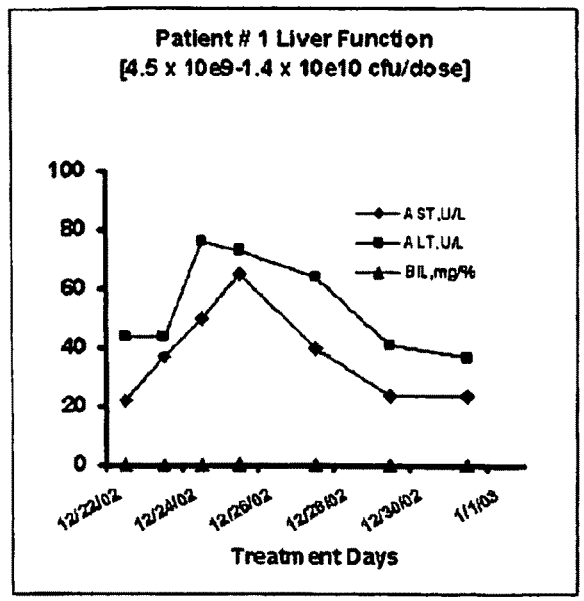
FIG. 5B depicts data indicating that Rexin-G has no adverse effects on for patient #1 liver function. AST (U/L) ALT (U/L), and bilirubin (mg %), plotted on the Y axis, are expressed as a function of treatment days, plotted on the X axis.
Figure 5C:
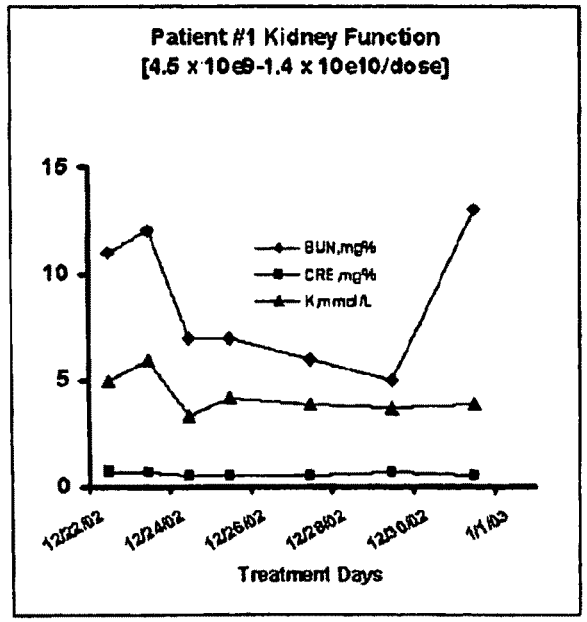
FIG. 5C depicts patient #1 Blood urea nitrogen (mg %), creatinine (mg %) and potassium (mmol/L) levels, plotted on the Y axis, expressed as a function of treatment days, plotted on the X axis. Dose Level I ($4.5 \times 10^9$ cfu/dose) was given for 6 consecutive days, rest period for two days, followed by Dose Level II ($9 \times 10^9$ cfu/dose) for 2 days, and then Dose Level III ($1.4 \times 10^{10}$ cfu/dose) for 2 days.
Figure 6A:
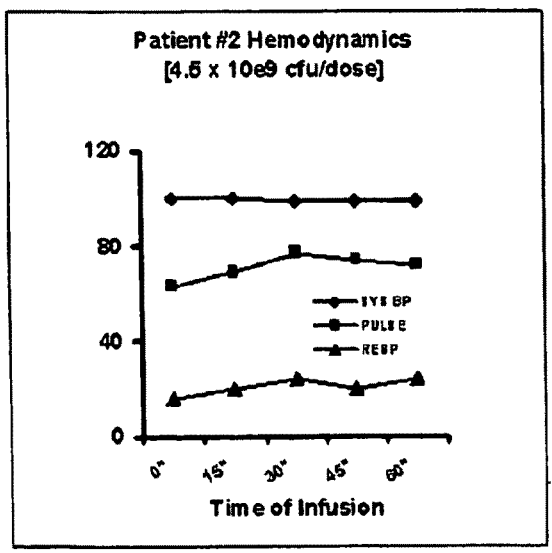
FIG. 6 provides data indicating that dose escalation of Rexin-G has no adverse effects on Patient #2's hemodynamic functions. For each dose level, the systolic blood pressure (mm Hg), pulse rate/min, and respiratory rate/per minute are plotted on the vertical axis as a function of time of infusion, plotted on the horizontal axis.
Figure 6B:
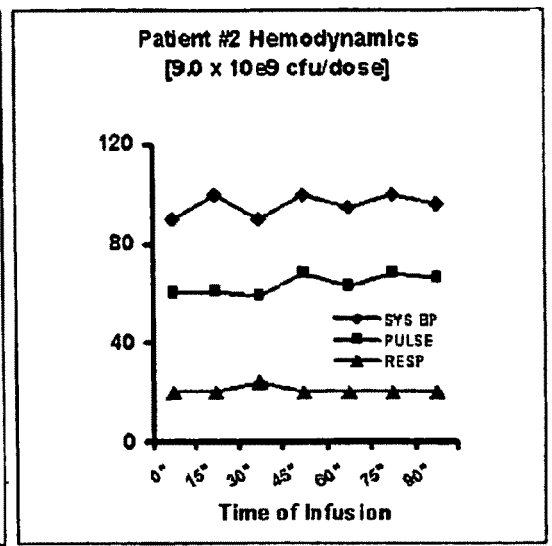
Figure 6C:
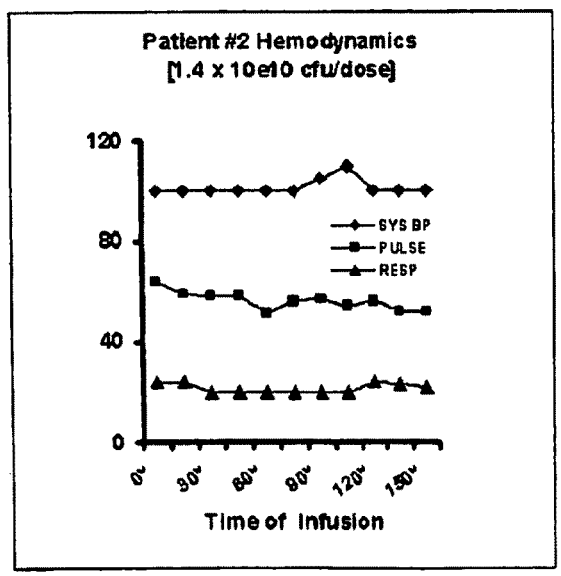
Figure 7A:
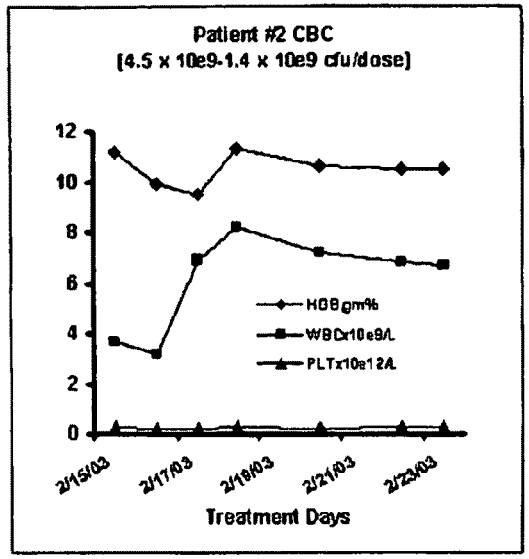
FIG. 7A depicts hemoglobin (gms %), white blood count and platelet count for patient #2 plotted on the Y axis and expressed as a function of treatment days, plotted on the X axis.
Figure 7B:
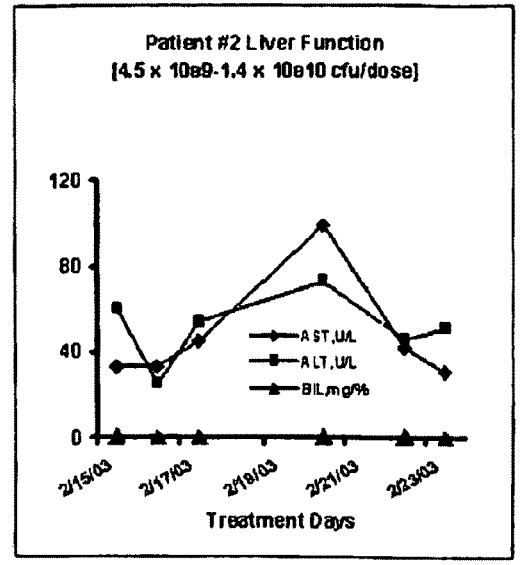
FIG. 7B depicts data indicating that Rexin-G has no adverse effects on for patient #2 liver function. AST (U/L) ALT (U/L), and bilirubin (mg %), plotted on the Y axis, are expressed as a function of treatment days, plotted on the X axis.
Figure 7C:
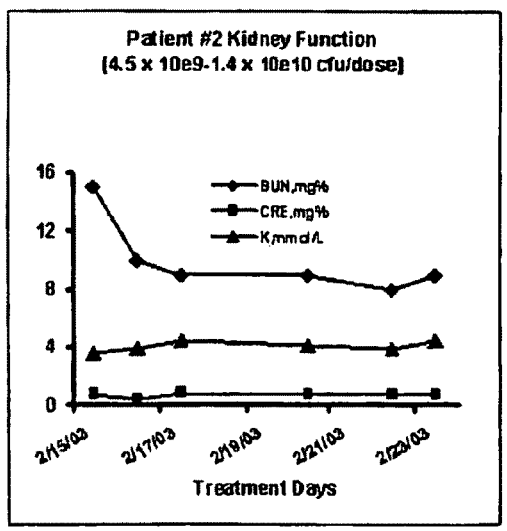
FIG. 7C depicts blood urea nitrogen (mg %), creatinine (mg %) and potassium (mmol/L) levels for patient #2, plotted on the Y axis expressed as a function of treatment days, plotted on the X axis. Dose Level I ($4.5 \times 10^9$ cfu/dose) was given for 5 consecutive days, followed by Dose Level II ($9 \times 10^9$ cfu/dose) for 3 days, and then Dose Level III ($1.4 \times 10^9$ cfu/dose) for 2 days.
Figure 8A:
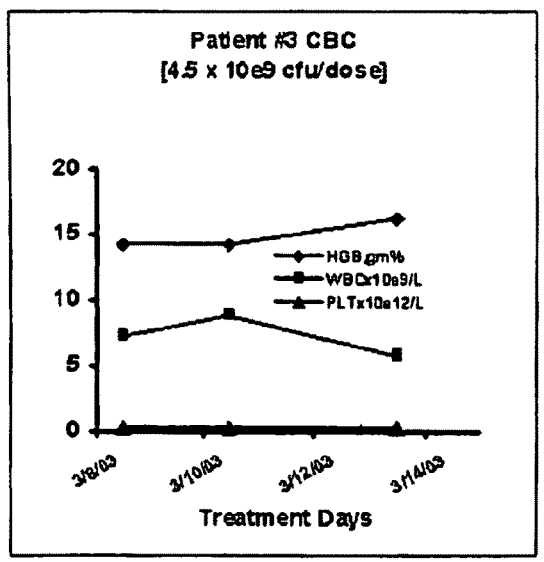
FIG. 8A depicts hemoglobin (gms %), white blood count and platelet count for patient #3 plotted on the Y axis and expressed as a function of treatment days, plotted on the X axis.
Figure 8B:
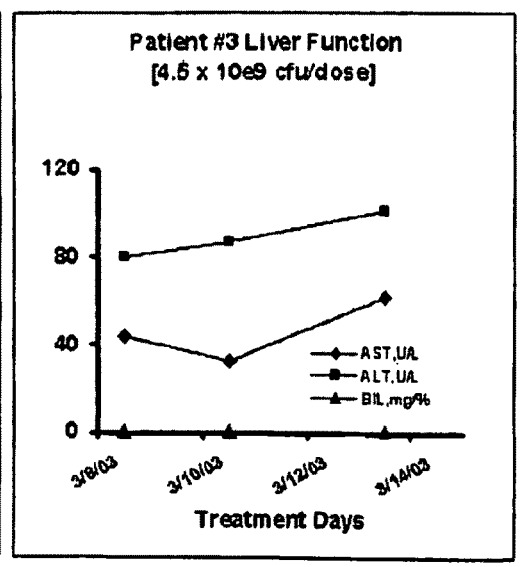
FIG. 8B depicts data indicating that Rexin-G has no adverse effects on for patient #3 liver function. AST (U/L) ALT (U/L), and bilirubin (mg %), plotted on the Y axis, are expressed as a function of treatment days, plotted on the X axis.
Figure 8C:
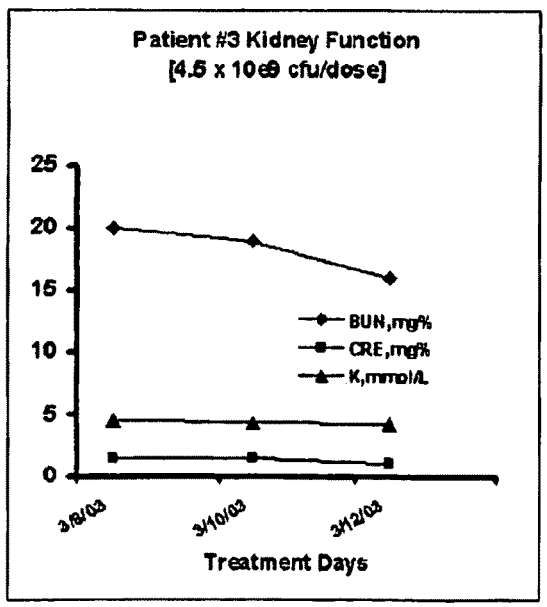
FIG. 8C depicts data indicating that Rexin-G has no adverse effects on for patient #3 kidney function. Blood urea nitrogen (mg %), creatinine (mg %) and potassium (mmol/L) levels, plotted on the Y axis, are expressed as a function of treatment days, plotted on the X axis. Dose Level I ($4.5 \times 10^9$ cfu/dose) was given for 6 consecutive days.
Figure 9:
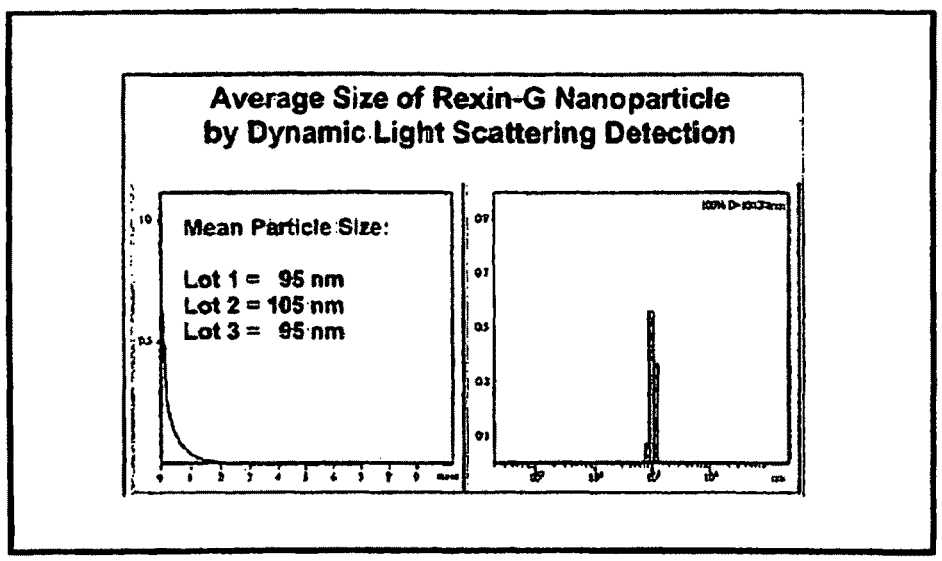
FIG. 9 depicts size measurements of Rexin-G nanoparticles. Using a Precision Detector Instrument (Franklin, Mass. 02038 U.S.A.), the vector samples were analyzed using Dynamic Light Scattering (DLS) in Batch Mode for determining molecular size as the hydrodynamic radius (rh). Precision Deconvolve software was used to mathematically determine the various size populations from the DLS data. The average particle size of 3 Rexin-G clinical lots are 95, 105 and 95 nm respectively with no detectable viral aggregation.
Figure 10:
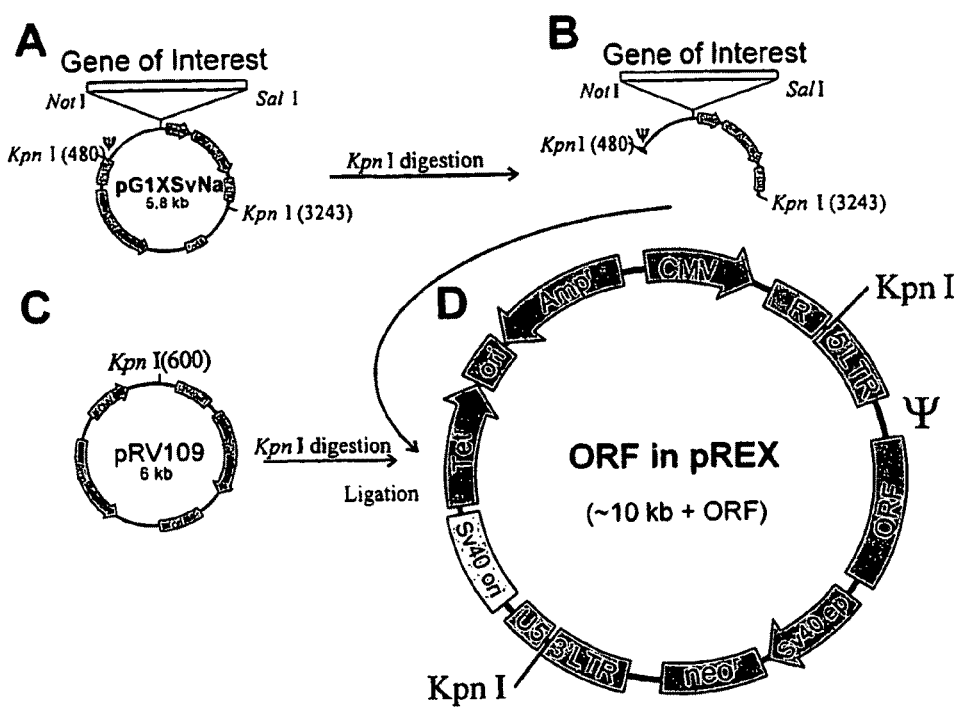
FIG. 10 depicts the High Infectious Titer (HIT) version of the GTI expression vector G1nXSvNa. The pRV109 plasmid provides the strong CMV promoter. The resulting pREX expression vector has an SV40 ori for episomal replication and plasmid rescue in producer cell lines expressing the SV40 large T antigen (293T), an ampicillin resistance gene for selection and maintenance in *E. coli*, and a neomycin resistance gene driven by the SV40 e.p. to determine vector titer. The gene of interest is initially cloned as a PCR product with Not I and Sal I overhangs. The amplified fragments are verified by DNA sequence analysis and inserted into the retroviral expression vector pREX by cloning the respective fragment into pG1XsvNa (Gene Therapy Inc.), then excising the Kpn I fragment of this plasmid followed by ligation with a linearized (Kpn I-digested) pRV109 plasmid to yield the respective HIT/pREX vector.

Patient #3, a 47 year old Chinese diabetic male was diagnosed to have Stage IVB adenocarcinoma of the body and tail of the pancreas, with numerous metastases to the liver and portal lymph node, confirmed by CT guided liver biopsy. Based on the rapid fatal outcome of Stage IVB adenocarcinoma of the pancreas, the patient was invited to participate in a second clinical protocol using Rexin-G frontline followed by gemcitabine weekly. A priming dose of Rexin-G was administered to sensitize the tumor to chemotherapy with gemcitabine for better cytocidal efficacy. The patient received daily IV infusions of Rexin-G at a dose of $4.5 \times 10^9$ Units/dose for 6 days for a total cumulative dose of $2.7 \times 10^{10}$ Units, followed by 8 weekly doses of gemcitabine (1000 mg/m$^2$). On Day 62, follow-up abdominal CT scan showed that the primary tumor had decreased in size from 7.0×4.2 cm (Tumor Volume: 64.2 cm$^3$) baseline measurement to 6.0×3.8 cm (Tumor Volume: 45 cm$^3$) (FIG. 3A). Further, there was a dramatic reduction in the number of liver nodules from 18 nodules (baseline) to 5 nodules (FIG. 3C) with regression of the largest liver nodule from baseline 2.2×2 cm (Tumor Volume: 4.6 cm$^3$) to 1×1 cm (Tumor Volume: 0.52 cm$^3$) on Day 62 (FIG. 3B). By the RECIST criteria, Patient #3 is alive with stable disease on Day 133 follow-up, 4.7 months from the start of Rexin-G infusions and 5 months from the time of diagnosis.

Table 3 illustrates the comparative evaluation of over-all tumor responses in the three patients. Using the RECIST criteria, Rexin-G induced tumor growth stabilization in all three patients.

TABLE 3

Evaluation of Over-all Tumor Responses by RECIST

| Patient No. | 1 | 2 | 3 |
|---|---|---|---|
| Stage of Disease | Recurrent IVB | IVA | IVB |
| Previous Rx | Whipples Procedure Ext. Beam Radiation Gemcitabine | Ext. Beam Radiation 5 Fluorouracil Gemcitabine | None |
| Karnofsky score before Treatment | 0 | 0 | 0 |
| Treatment's & Dose | Rexin-G IV (3.0 × 10e11 U) | Rexin-G IV (1.8 × 10e11 U) | Rexin-G IV (2.7 × 10e11 U) Gemcitabine IV [1000 mg/m$^2$ × 8] |
| Response | Tumor growth stabilization | Tumor growth stabilization | Tumor growth stabilization |
| Duration of Response | 3.4 months | >5.5 months | >4.7 months |
| Survival Status | Alive, with progressive disease, 20 months from diagnosis | Alive, with stable disease, 14 months from diagnosis | Alive, with stable disease, 5 months from diagnosis |

In this study, two methods were used to evaluate tumor responses to intravenous infusions of Rexin-G. Using the NCI-RECIST criteria that measures the sum of the longest diameters of target lesions that are greater than 2 cm, and the disappearance vs persistence of all non-target lesions as points of comparison, 3 of 3 (100%) patients treated with Rexin-G had tumor growth stabilization for longer than 100 days (3 months) (Table 3). Evaluation of response by tumor volume measurement (formula: width²×length×0.52) (16), revealed that Rexin-G induced tumor regression in 3 of 3 (100%) patients, i.e., a 33-62% regression of metastatic lymphadenopathy in Patient #1 (Table 2), a 47% regression of the primary tumor in Patient #2 (FIG. 2C), and a 30% regression of the primary tumor, eradication of 72% (13/18) of metastatic liver foci, and an 89% regression of a metastatic portal node in Patient #3 as documented by imaging studies (MRI or CT scan) and caliper measurements (FIG. 3). Further, evaluation of safety showed that no dose-limiting toxicity occurred up to a cumulative vector dose of 3×10¹¹ Units, indicating that more vector may be given to achieve greater therapeutic efficacy. The Rexin-G vector infusions were not associated with nausea or vomiting, diarrhea, neuropathy, hair loss, hemodynamic instability, bone marrow suppression, liver or kidney damage.

Example 6

Clinical Trial A, Phase I/II Rexin-G™ in Locally Advanced or Metastatic Pancreatic Cancer Clinical Study A includes Phase I/II or single-use protocols investigating intravenous infusions of Rexin-G™ for locally advanced or metastatic pancreatic cancer following approval by the Philippine Bureau of Food and Drugs (BFAD) or by the United States Food Drug Administration (FDA), and the Institutional Review Board or Hospital Ethics Committee (Gordon et al. (2004) Int'l. J. Oncol. 24: 177-185). The objectives of the study were (1) to determine the safety/toxicity of daily intravenous infusions of Rexin-G™, and (2) to assess potential anti-tumor responses to intravenous infusions of Rexin-G™. The protocol was designed for patients with an estimated survival time of at least 3 months. After informed consent was obtained, six patients with locally advanced unresectable or metastatic pancreatic cancer were treated with repeated infusions of Rexin-G™. Five of the six patients had failed standard chemotherapy; these patients completed the intra-patient dose escalation protocol in Manila, Philippines and/or in Brooklyn, N.Y., USA, as follows: Days 1-2: 3.8×10e9 Units; Days 34: 7.5×10e9 Units; Days 5-6:1.1× 10e10 Units; Days 7-10: 1.5×10e10 Units; Rest one week; Days 18-27: 1.5×10e10 Units. Two patients received 1 additional cycle, and one patient received 7 additional cycles. The sixth patient who presented with unresectable stage IV pancreatic cancer, received combination therapy as a first-line treatment, consisting of six days of IV Rexin-G™ (3.8×10e9 Units/day) followed by gemcitabine (1000 mg/m2) weekly for 8 weeks. For Clinical Study A, the Rexin-G™ preparation had a potency of 3×10e7 Units/ml.

Adverse events were graded according to the NIH Common Toxicity Criteria (CTCAE Version 2 or 3) (Common Toxicity Criteria Version 2.0. Cancer Therapy Evaluation Program. DCTD, NCI, NIH, DHHS, March, 1998.). To evaluate the clinical efficacy of Rexin-G™, we took into consideration the general cytocidal and anti-angiogenic activities of the agent (Gordon et al. (2000) Cancer Res. 60:3343-3347, Gordon et al. (2001) Hum. Gene Ther. 12: 193-204), as well as the dynamic sequestration of the pathotropic nanoparticles into metastatic lesions (Gordon et al. (2001) Hum. Gene Ther. 12: 193-204) that would affect the biodistribution or bioavailability of the targeted nanoparticles during the course of the treatment. Since the vector will accumulate more readily in certain cancerous lesions—depending on the degree of tumor invasiveness and angiogenesis—it is not expected to be distributed evenly to the rest of the tumor nodules, particularly in patients with large tumor burdens. This would predictably induce a mixed tumor response wherein some tumors may decrease in size while other tumor nodules may become bigger and/or new lesions may appear. Thereafter, with the normalization or decline of the overall tumor burden, the pathotropic surveillance function would distribute the circulating nanoparticles somewhat more uniformly. Additionally, the treated lesions may initially become larger in size due to the inflammatory reactions or cystic changes induced by the necrotic tumor. Therefore, two additional measures were used in the evaluation of objective tumor responses to Rexin-G™ treatment, aside from the standard Response Evaluation Criteria in Solid Tumors (RECIST; Therasse et al. (2000) J. Nat'l. Cancer Inst. 92:205-216): that is, (1) O'Reilly's formula for estimation of tumor volume: L×W²×0.52 (27 O'Reilly et al. (1997) Cell 88:277-285), and (2) the induction of necrosis or cystic changes in tumors during the treatment period. Thus, a decrease in the tumor volume of a target lesion of 30% or greater, or the induction of necrosis or cystic changes within the tumor were considered partial responses (PR) or positive effects of treatment. The one-sided exact test was used to determine the significance of differences between the PRs of patients treated with Rexin-G™ and historical controls with an expected 5% PR.

This initial Phase I/II study examines the safety and potential efficacy of an intra-patient dose escalation protocol. As shown in Table 4, partial responses (PR) of varying degrees were noted in 5 out of 6 patients treated with Rexin-G™ while stable disease was observed in the remaining patient. Three of 6 (50%) patients had a 30% or greater decrease in tumor size by RECIST or by tumor volume measurement, and 2 of 6 (33%) patients had necrosis of either the primary tumor or metastatic nodules by biopsy and/or by follow-up MRI/CAT scan. Further analysis of one particular patient (A3), in whom 6 of 8 liver tumor nodules disappeared by CT scan, was facilitated by means of a liver biopsy, which revealed an increased incidence of apoptosis, necrosis, and fibrosis within the tumor nodules similar to that observed in preclinical studies (18, 19), along with the observation of numerous tumor infiltrating lymphocytes in the residual liver tumors of the biopsied liver (FIGS. 20-22). The presence of immunoreactive T and B lymphocytes infiltrating the residual liver tumors (FIG. 22) indicates that Rexin-G™ does not suppress local immune responses. Progression-free survival was greater than 3 months in 4 of 6 (67%) patients. Median survival after Rexin-G™ treatment in chemotherapy-resistant patients was 10 months, and median survival after diagnosis was 25 months. In contrast, the reported median survival of patients with pancreatic cancer who received either gemcitabine or 5-FU (standard treatments) as a first-line drug was 5.65 and 4.41 months after diagnosis, respectively (Burris et al. (1997) J. Clin. Oncol. 15:2403-2413). Using the one-sided exact test, the significance level of partial responses in Rexin-G™-treated patients was <0.025 when compared to the PR rates of historical controls. These initial findings, albeit documented in a relatively small number of patients, are sufficient to indicate that Rexin-G™ is clinically effective, even in modest doses, is clearly superior to no medical treatment, and may be superior to gemcitabine when used as a single agent for the treatment of patients with advanced or metastatic pancreatic cancer.

TABLE 4

Objective Tumor Response, Progression-free Survival, and Overall Survival of Participants in Clinical Study A

| Patient's Initials Age | Objective Tumor Response | Progression Free Survival | Status/Survival After Rexin-G Treatment | Overall Survival from Dx |
|---|---|---|---|---|
| A1 46 years | Partial Response: Necrosis of primary tumor with 24% decrease in tumor size; 33-62% decrease in size supraclavicular lymph nodes Symptomatic relief of pain | 3.5 months | Expired 10 months | 23 months |
| A2 55 years | Partial Response (RECIST): 47% decrease in primary tumor volume, followed by complete disappearance of the tumor Symptomatic relief of pain | 9 months | Expired 13 months | 25 months |
| A3 45 years | Partial Response (RECIST): 47% decrease in primary tumor volume; disappearance of 6 of 8 liver nodules; apoptosis and necrosis of liver nodules in biopsied liver Symptomatic relief of pain | 4 months | Expired 9 months | 19 months |
| A4 64 years | Partial Response/Stable Ds: disappearance of 5 of 11 liver nodules; stable primary | 2 months | Expired 8 months | 48 months |
| A5 53 years | Stable Disease: no change in primary tumor; one of 3 liver nodules disappeared | 2 months | Expired 10 months | 30 months |
| A6 46 years | Partial Response (RECIST): 30% decrease in primary tumor volume; disappearance of 13 of 18 liver nodules | 5 months | Expired 7 months | 7 months |

All 6 patients tolerated the Rexin-G™ infusions well with no associated nausea or vomiting, diarrhea, mucositis, hair loss, or neuropathy. Three of six (50%) patients had symptomatic relief of pain. There was no significant alteration in hemodynamic function, bone marrow suppression, liver, kidney or any organ dysfunction that was related to the investigational agent. The only adverse events that were attributed as definitely related to the investigational agent were generalized rash and urticaria in 2 of 6 patients (Grade 1-2), and those attributed as possibly related were chills and fever in 2 of 6 patients (Grade 1). The limited number of treatment-emergent adverse events observed in this study suggests that Rexin-G™ administered intravenously at these escalating doses is a relatively safe therapy.

Example 7

Clinical Study B, Phase I/II Rexin-G™ in Various Advanced or Metastatic Solid Tumors Clinical Study B represents an expansion of Clinical Study A. Based on the encouraging results of the initial clinical experiences with Rexin-G™, the Phase I/II study was expanded to further determine the safety and potential efficacy of a higher dose of Rexin-G™, to extend the clinical indication to all advanced or metastatic solid tumors that are refractory to standard chemotherapy, and to adjust the treatment schedule and protocol to enable outpatient treatment. The objectives of this study were (1) to determine the safety/toxicity of daily intravenous infusions of Rexin-G™, and (2) to assess potential anti-tumor responses to intravenous infusions of Rexin-G™ at a higher dose level. The protocol was designed for patients with an estimated survival time of at least 3 months. After informed consent was obtained, ten patients with metastatic cancer originating from either the ectoderm (melanoma, 1; squamous cell CA of larynx, 1), the mesoderm (leiomyosarcoma, 1) or the endoderm (pancreas, 2; breast, 2; uterus, 1; colon, 2), and one newly diagnosed previously untreated patient with metastatic pancreatic cancer who had refused chemotherapy (Total number of patients=11), received intravenous Rexin-G™ as a single agent at a dose of $3.0 \times 10e10$ Units per day for a total of 20 days, according to the following treatment schedule: Days 1-5, 8-12, 15-19, and 22-26; monday to friday with week-end rest period. An improved GMP manufacturing and bioprocessing protocol enabled the production of Rexin-G™ at substantially higher titers, such that the preparations used for Clinical Study B exhibited a vector potency of $7 \times 10e8$ Units/ml.

Adverse events were graded according to the NIH Common Toxicity Criteria (CTCAE Version 2 or 3) (Common Toxicity Criteria Version 2.0. Cancer Therapy Evaluation Program. DCTD, NCI, NIH, DHHS, March, 1998.). To evaluate the clinical efficacy of Rexin-G™, we took into consideration the general cytocidal and anti-angiogenic activities of the agent (Gordon et al. (2000) Cancer Res. 60:3343-3347, Gordon et al. (2001) Hum. Gene Ther. 12: 193-204), as well as the dynamic sequestration of the pathotropic nanoparticles into metastatic lesions (Gordon et al. (2001) Hum. Gene Ther. 12: 193-204) that would affect the biodistribution or bioavailability of the targeted nanoparticles during the course of the treatment. Since the vector will accumulate more readily in certain cancerous lesions—depending on the degree of tumor invasiveness and angiogenesis—it is not expected to be distributed evenly to the rest of the tumor nodules, particularly in patients with large tumor burdens. This would predictably induce a mixed tumor response wherein some tumors may decrease in size while other tumor nodules may become bigger and/or new lesions may appear. Thereafter, with the normalization or decline of the overall tumor burden, the pathotropic surveillance function would distribute the circulating nanoparticles somewhat more uniformly. Additionally, the treated lesions may initially become larger in size due to the inflammatory reactions or cystic changes induced by the necrotic tumor. Therefore, two additional measures were used in the evaluation of objective tumor responses to Rexin-G™ treatment, aside from the standard Response Evaluation Criteria in Solid Tumors (RECIST; Therasse et al. (2000) J. Nat'l. Cancer Inst. 92:205-216): that is, (1) O'Reilly's formula for estimation of tumor volume: $L \times W^2 \times 0.52$ (27 O'Reilly et al. (1997) Cell 88:277-285), and (2) the induction of necrosis or cystic changes in tumors during the treatment period. Thus, a decrease in the tumor volume of a target lesion of 30% or greater, or the induction of necrosis or cystic changes within the tumor were considered partial responses (PR) or positive effects of treatment.

This study extends the initial Phase I/II pancreatic cancer protocols with dose intensification and expanded clinical application to all solid tumors. As shown in Table 5, partial responses of varying degrees of either the primary tumor or the metastatic nodules were noted in 7 of 11 (64%) patients. Five of 11 (45%) patients developed necrosis and apoptosis of the primary tumors and/or metastatic nodules by either biopsy or CT scan, and 5 of 11 (45%) patients had greater than 30% reduction in the size of the primary tumor or metastatic nodules by RECIST or tumor volume measurement. Two of 11 patients had stable disease, one patient with massive tumor burden had a mixed tumor response and one patient with a large tumor burden (~50 liver nodules) had progressive disease.

node(s) to which cancer is likely to spread from a primary tumor—are of considerable importance to our understanding of the pathogenesis, diagnosis, and prospective treatment of metastatic disease, the conspicuous penetrance of Rexin-G™ into both regional and distant lymph nodes is both striking and auspicious (Tables 4 and 5). The clinical significance of the finding that the pathotropic nanoparticles in Rexin-G™ retain their bioactivity as they circulate throughout the body, not only accumulating in primary and metastatic lesions but also draining into lymph nodes with therapeutic impact, cannot be overstated. As shown in FIG. 23, a surgical biopsy of a cancerous lymph node from the inguinal region of a patient with malignant melanoma showed substantial necrosis (23-A), large areas of overt apoptosis, (23-B), and zones wherein hemosiderin-laden macrophages (23-C) are evacuating tumor debris. Moreover, immunohistochemical staining revealed significant mononuclear infiltrations with CD35+ dendritic cells (23-D), CD68+ macrophages (23-E), CD8+ killer T cells (23-F), and CD4+ helper T cells (not shown). The realization that the gene delivery function (i.e., cytocidal activity) of pathotropic nanoparticles remains active as it penetrates metastatic disease within sentinel lymph nodes, and does not disrupt but appears to work in concert with the immune system, reaffirms the potentiality of future cancer vaccinations in situ, using this targeted gene delivery system bearing a cytokine gene.

In another patient with squamous cell CA of larynx, a dramatic re-opening of the upper airway was documented by neck MRI (FIG. 24), which correlated with the patient's re-gaining of her voice. Progression-free survival ranged

TABLE 5

Objective Tumor Response, Progression-free Survival, and Overall Survival of Participants in Clinical Study B

| Patient's Initials, Age, Dx and Date of Dx | Over-all Tumor Response [Symptomatic Relief, Caliper, CT scan and MRI] | Progression Free Survival | Status/Survival After Rexin-G Treatment | Overall Survival from Diagnosis |
|---|---|---|---|---|
| B1 53 years Breast Cancer | Partial Response (RECIST): Apoptosis and necrosis of tumor nodule by biopsy; 50% decrease in supraclavicular node by PET/CT scan; | 3 months | Alive >13 months | >6.6 years |
| B2 58 years Uterine Cancer | Partial Response: Necrosis of supraclavicular lymph nodes by CT scan; 33% decrease in cervical lymph node by calipers Symptomatic relief from nerve pain | 3 months | Expired 4 months | 2 years 4 months |
| B3 52 years Breast Cancer | Stable Disease: no interval change in pulmonary nodules Symptomatic relief from coughing and bone pain | 2 months | Alive >7 months | >3 years 5 months |
| B4 41 years Melanoma | Partial Response: Necrosis and apoptosis of biopsied tumor nodules; 50% decrease in tumor volume by CT scan | 3 months | Alive >6 months | >15 months |
| B5 53 years Pancreatic Cancer | Progressive Disease Symptomatic relief from pain | N.A. | Alive >6 months | >11 months |
| B6 48 years Squamous Cell CA, larynx | Partial Response (RECIST): 300% increase in upper airway diameter; stable lung nodules Regained voice | 3 months | Alive >6 months | >24 months |

Progressive reduction of cancerous lymph nodes with repeated infusions of Rexin-G™ was consistently observed in patients with pancreatic cancer, and again in patients with uterine cancer, colon cancer, breast cancer and malignant melanoma, which is remarkable and meaningful in terms of understanding the pertinent pharmacodynamics. While it is well known that sentinel lymph node(s)—the first lymph from one to greater than 5 months. Median survival time was greater than 6 months from the start of Rexin-G™ treatment, and greater than 24 months from diagnosis. Eight of 11 (72%) patients lived/are alive greater than 6 to 13 months after treatment with Rexin-G™. Taken together, Rexin-G™ appears to have single agent activity in a broad spectrum of resistant tumor types. Further, it was noted that sustained therapeutic benefit was observed in the majority of the patients despite the brevity of the treatment.

All eleven patients tolerated the vector infusions well with no associated nausea or vomiting, diarrhea, mucositis, hair loss or neuropathy. Eight of 11 (73%) had symptomatic relief of pain, bloating, throbbing, hoarseness, and fatigue. There was no significant alteration in hemodynamic function, bone marrow suppression, liver, kidney or any organ dysfunction that was related to the investigational agent. The absence of treatment-related adverse events further suggests that, even in increased vector doses, Rexin-G™ is a relatively safe therapy. At this point, the absence of dose limiting toxicity, combined with compelling indications of single agent efficacy in a variety of different tumor types and the recent availability of higher potency formulations of Rexin-G™ encouraged the advancement and regulatory approval of clinical trials designed to focus on increased clinical efficacy and the optimization of treatment protocols.

Example 8

Clinical Study C, Expanded Access of Rexin-G™ in Metastatic Pancreatic and Colon Cancer and "The Calculus of Parity"

Clinical Study C involves a small group of patients who participated in an Expanded Access Program for Rexin-G™ for all solid tumors, a provisional program which was recently approved by the Philippine BFAD. The innovative protocol was designed to address (i.e., to reduce or eradicate) a given patient's total tumor burden as quickly, yet, as safely possible in order to prevent or forestall "catch up" tumor growth, and thereby minimize this confounding parameter. The estimated total dosage to be utilized was determined by an empiric calculation, referred to herein as "The Calculus of Parity" (referring to as a method of equality, as in amount, or functional equivalence). The basic formula takes into consideration the overall tumor burden, estimated from imaging studies (1 cm=approximately 1×10e9 cancer cells), an empiric performance coefficient (φ) or Physiological Multiplicity of Infection (P-MOI, in the terms of virology) for the targeted vector system (the P-MOI for a non-targeted vector system is essentially infinite), and the potency of the clinical-grade formulation (in Units/ml). Tumor burden was measured as the sum of the longest diameters of the tumor nodules, in centimeters, multiplied by 1×10e9 and expressed as the total number of cancer cells. An "operationally defined" performance coefficient (φ) or Physiological MOI (P-MOI) of 100 for Rexin-G™ was based on quantitative demonstrations of enhanced transduction efficiency of the targeted gene delivery system documented in a wide variety of preclinical studies, and upon the dose-dependent performance of Rexin-G™ observed in the crucible of the initial clinical trials. Importantly, the generation of a high-potency Rexin-G™ product (~1.0×10e9 Units/ml) enabled the administration of calculated optimal doses of Rexin-G™ to be delivered intravenously without the risk of volume overload. Pioneering Studies: After completion of the first 20 days of Rexin-G™ infusions, two patients with metastatic pancreatic cancer and one patient with metastatic colon cancer opted (with additional informed consent) to continue to receive intravenous Rexin-G™ infusions up to a total dose of ~2.5×10e12 Units over 6 weeks (1 patient) and 16 weeks (2 patients), respectively. This provided a Calculus of Parity which roughly paralleled the patients' estimated tumor burden based on CT scan or MRI.

Adverse events were graded according to the NIH Common Toxicity Criteria (CTCAE Version 2 or 3) (Common Toxicity Criteria Version 2.0. Cancer Therapy Evaluation Program. DCTD, NCI, NIH, DHHS, March, 1998.). To evaluate the clinical efficacy of Rexin-G™, we took into consideration the general cytocidal and anti-angiogenic activities of the agent (Gordon et al. (2000) Cancer Res. 60:3343-3347, Gordon et al. (2001) Hum. Gene Ther. 12: 193-204), as well as the dynamic sequestration of the pathotropic nanoparticles into metastatic lesions (Gordon et al. (2001) Hum. Gene Ther. 12: 193-204) that would affect the biodistribution or bioavailability of the targeted nanoparticles during the course of the treatment. Since the vector will accumulate more readily in certain cancerous lesions—depending on the degree of tumor invasiveness and angiogenesis—it is not expected to be distributed evenly to the rest of the tumor nodules, particularly in patients with large tumor burdens. This would predictably induce a mixed tumor response wherein some tumors may decrease in size while other tumor nodules may become bigger and/or new lesions may appear. Thereafter, with the normalization or decline of the overall tumor burden, the pathotropic surveillance function would distribute the circulating nanoparticles somewhat more uniformly. Additionally, the treated lesions may initially become larger in size due to the inflammatory reactions or cystic changes induced by the necrotic tumor. Therefore, two additional measures were used in the evaluation of objective tumor responses to Rexin-G™ treatment, aside from the standard Response Evaluation Criteria in Solid Tumors (RECIST; Therasse et al. (2000) J. Nat'l. Cancer Inst. 92:205-216): that is, (1) O'Reilly's formula for estimation of tumor volume: $L \times W^2 \times 0.52$ (27 O'Reilly et al. (1997) Cell 88:277-285), and (2) the induction of necrosis or cystic changes in tumors during the treatment period. Thus, a decrease in the tumor volume of a target lesion of 30% or greater, or the induction of necrosis or cystic changes within the tumor were considered partial responses (PR) or positive effects of treatment.

This study represents the initial report of clinical experience in an Expanded Access Program for Rexin-G™ for treating all solid tumors, introducing an innovative personalized dose-dense regimen referred to as the Calculus of Parity. In this preliminary yet important interim analysis, dramatic responses were noted in all three patients, each with an extensive tumor burden. In one patient (C1), the Calculus of Parity (or functional equivalence) approximated a cumulative dosage that led to liquefaction necrosis and cystic conversion of the unresectable pancreatic tumor and either cystic conversion or disappearance of all metastatic liver nodules on follow-up MRI (FIG. 25). Aspiration of one cystic tumor nodule was negative for malignant cells. In the second patient (C2), suffering from Stage IV colon cancer, a cumulative dosage approaching the predetermined Calculus of Parity was effective in reducing the bulk of the metastatic disease: 84% necrosis observed in the liver tumor nodules was documented by image analysis. In the third patient (C3), a significant decrease in the primary pancreatic tumor and in the number (from 28 to 12 lung nodules) and the size of pulmonary nodules were noted by CT scan. Progression-free survival and overall survival was greater than 6 months after Rexin-G™ treatment in two patients. These findings provide preliminary evidence to support the hypothesis that the Calculus of Parity may be used to determine the total cumulative dose of Rexin-G™ that would be needed to address a given patient's tumor burden, and thereby comprise an optimal induction regimen.

All three patients tolerated the vector infusions well with no associated nausea or vomiting, diarrhea, mucositis, hair loss or neuropathy. There were no acute alterations in hemodynamic function, bone marrow suppression, liver, kidney or any organ dysfunction that was related to the investigational agent. Two patients did develop anemia requiring red cell transfusion (grade 3), which was attributed as possibly related to subsequent bleeding into the necrotic tumors. One patient developed sporadic episodes of thrombocytopenia (grade 1-2) which was attributed as possibly related to the investigational agent. One patient died of acute fulminant staph epidermidis septicemia three months after Rexin-G™ treatment, which was NOT attributed to the investigational agent. The results of this patient's autopsy showed almost complete necrosis of the residual pancreatic tumor, and 75-95% necrosis of the metastatic tumors remaining in the liver and abdominal mesentery, with normal histology recorded in the bone marrow, heart, and brain. The lack of systemic toxicity associated with Rexin-G™ administration underscores the potential advantages of Rexin-G™ over standard chemotherapy in terms of efficacy in managing metastatic cancer, as well as other quality-of-life measures. In each case, the extent of the overall tumor destruction was impressive. The demonstration that a dose-dense regimen of Rexin-G™, specifically tailored to overcome a patient's tumor burden, is capable of achieving these levels of efficacy underscores the need to further refine the Calculus of Parity, to define the optimal rate(s) of tumor eradication, and to discern the optimal supportive care for a patient undergoing post-tumoricidal wound healing.

Example 9

Clinical Study D, Phase I Clinical Trial of Rexin-G for Locally Advanced or Metastatic Pancreatic Cancer Refractory to Standard Chemotherapy In Clinical study D, 12 patients with locally advanced or metastatic pancreatic cancer were treated with intervenous administration of Rexin-G in order to confirm the initial clinical results seen in the 6 patients of Clinical Study A, above. These initial patients received repeated Rexin-G infusions up to a cumulative dose of 10e12 cfu without exhibiting bone marrow suppression or organ damage.

The study was designed to evaluate the maximum tolerated dose (MTD) based on observed dose-limiting toxicity (DLT) according to a dose escalation scheme where the MTD is defined as the highest safely tolerated dose with at most 1 out of 6 patients experience a DLT with the next higher dose level having at least 2 out of 6 patients with a DLT. Hematologic adverse events were defined as any Grade≥3 at least possibly related to Rexin-G as per NCI Common Terminology Criteria for Adverse Events v 3.0. Except grade 3 ANC lasting <72 hours. Non-hematologic adverse events were defined as any Grade≥3 at least possibly related to Rexin-G as per NCI Common Terminology Criteria for Adverse Events v 3.0. Grade≥3 nausea, vomiting, or diarrhea, was considered dose-limiting only if patient has had maximal supportive care. Alopecia was not considered dose limiting.

Patients received Rexin-G at three different dose levels. Dose level 1 had 3 patients that received treatment on days 1-7 and 15-21 at 7.5×10e9 cfu. Dose level 2 had 6 patients that received treatment on days 1-7 and 15-21 at 1.1×10e10. Dose level 3 had 3 patients that received treatment on days 1-5, 8-12, 15-19, and 22-26 at 3.0×10e10 cfu. All patients received a maximum volume per dose of 8 ml per per kilogram of body weight.

In dose level 1, all 3 patients finished their treatment course and received 100% of the dose. No patient experienced a DLT during treatment or during their 1-week of observation. In dose level 2, four patients received the full dose of Rexin-G. Of the two patients that did not receive the full dose, one patient had the dose adjusted due to a grade 3 elevations in AST and ALT felt to be possibly related to treatment. The patient, however, was also taking 1000 mg of acetaminophen daily. These elevations were reduced to grade I within 72 hours after discontinuing both Rexin-G and acetaminophen, allowing the completion of Rexin-G treatment. The other patient had treatment held one day due to the occurrence of a grade 2 alkaline phosphatase adverse event. In dose level 3, no toxicity summary report is available yet, however, no patient experienced a SAE or DLT.

Secondary to confirming the safety of Rexin-G at the tested dose levels, the pharmacokinetics of the viral particles following intravenous infusions and their potential for evoking immune responses, undergoing recombination events (replication competent retroviral generation), and vector integration in non-target organs was studied. For the pharmacokinetics of the viral particles, blood samples were obtained from all 12 patients at the times 0, 5, 30, 60, 120 min and 24 hours post-vector infusion on Day 1. Rexin-G vector concentration (viral titer) was determined and quantified based on expression of the neomycin resistance (neor) gene product.

Briefly, 1.5×104 HT1080 (human fibrosarcoma cells) cells were plated in each of 12-well plates one day prior to transduction. Culture medium was incubated with 0.5 ml of serial dilutions of viral supernatant with 8 µg/ml polybrene for 3½ hrs at 32° C. 5% C02 with gentle rocking. One half ml of fresh media was added to the cultures, which were then maintained overnight at 37° C., 5% C02. For expression of the neor gene product, G418 resistant colonies were selected by treatment with G418 drug (500 µg/ml) beginning 24 hrs after transduction. The number of G418 resistant colonies stained with methylene blue were quantified by limiting dilution after incubation in G418 drug for 13 days. Viral titer was expressed as number of colony forming units per milliliter serum (cfu/ml).

The results demonstrated that neor selectable Rexin-G vector was very low ($<1\times10^2$ cfu/ml) but detectable in blood samples obtained 5 minutes after Rexin-G infusion in 3 of 3 patients at Dose Level 1, in 2 of 6 patients at Dose Level 2 and in 2 of 3 patients at Dose Level 3. Vector was diminished at 30 minutes with 2 of 3 patients having detectable vector at Dose Level 1, 0 of 6 patients at Dose Level 2 and in 0 of 6 patients at Dose Level 3. No vector was recovered at time points beyond 30 minutes. While minimal vector recovery could be due to many factors, this finding most likely indicates vector biodistribution into the tumors, which is known to occur within minutes of infusion. This is consistent with the results of preclinical studies wherein significant amounts of immunoreactive Rexin-G were found to accumulate in cancer xenografts within minutes following intravenous infusion (Gordon et al., 2001). This rapid partitioning of circulating vector into tumors is attributed to the pathotropic (disease-seeking) vector's designated affinity and adherence (as in platelet adhesion) to microscopic arrays of collagenous proteins characteristically exposed in areas of active angiogenesis and/or tumor invasion. Therefore, the short biologic half-life of Rexin-G in the circulation of treated patients may be attributable to rapid biodistribution into primary and metastatic lesions. Regardless of the mechanisms involved, little, if any, circulating Rexin-G remains in systemic circulation beyond 30 minutes after its infusion.

Testing for presence of anti-vector antibodies was performed on serum samples obtained from all 12 patients pre-infusion and 4 weeks (Dose Level 1, 2) and 6 weeks (Dose Level 3) after treatment. The presence of anti-vector antibodies was tested using a vector neutralization assay combined with Western slot blot analysis. No vector neutralizing antibodies and antibodies against the gp70 env protein were not detected in the sera of patients treated with Rexin-G at Dose level I-III. These data confirm the results of preclinical studies in mice wherein no vector neutralizing antibodies were detected following repeated infusions of Rexin-G. These findings affirm the low immunogenicity of Rexin-G, which enables repeated intravenous administration without losing potential clinical efficacy.

The presence of RCR was performed on DNA extracted from peripheral blood lymphocytes obtained from 7 patients at Time 0 (before vector infusion) and either four weeks (Dose level 2) or 6 weeks (Dose level 3) after the start of vector infusions. The assay was designed to detect through PCR the presence a small portion of the 2001 bp Moloney Murine Leukemia Virus Envelope (MoMLV Env) gene (164 bp fragment from 411-574 bp) present in the Rexin-G retroviral vector. All post-infusion samples tested were found to be negative for RCR.

Testing for presence of vector DNA integration was performed on DNA extracted from peripheral blood lymphocytes from 9 patients obtained pre-infusion, 1 week, and 4 weeks (Dose Level 1, 2); day 5 and 6 weeks (Dose Level 3) after treatment. Testing for vector DNA integration in peripheral blood lymphocytes was performed by centrifuging patient blood samples to separate white blood cells from RBC's and serum. Isolated white blood cell DNA underwent Real Time PCR using Neo primers to amplify a small portion of the 795 bp Neomycin Phosphotransferase (NPT) gene (75 bp fragment from 382-456 bp) present in the dnG1-Erex retroviral vector.

Vector DNA sequences were not detected in peripheral blood lymphocyte DNA confirming preclinical data where no vector DNA was detected in non-target organs, aside from liver and spleen (organs of viral clearance) of Rexin-G-treated mice, rats, and rabbits.

Anti-tumor activity following intravenously administered Rexin-G was evaluated by RECIST. All 3 patients receiving dose level 1 progressed around day 28. Five of the six patients enrolled at dose level 2 progressed approximately within a month from beginning treatment. The other patient was considered to have stable disease per RECIST, but did suffer from symptomatic deterioration. All 3 patients receiving dose level 3 progressed at Day 42 evaluation.

Tumor density, as measured in Hounsfield Units was used to evaluate biologic activity of Rexin-G. For each of the 3 patients at dose level 1 and the 6 patients at dose level 2, data on tumor density in Hounsfield units at baseline and at day 28 are available for multiple lesions (5 lesions in seven patients, 3 lesions in one patient, and 2 lesions in one patient). Those data have been summarized in two ways.

Table 6 shows, for each patient, the proportion of lesions for which there was any decrease in tumor density, as well as the proportions of lesions for which there were decreases of at least 10%, 15%, and 20%. There is a clear tendency for lesions to decrease in density; all 9 patients had a net decrease in Hounsfield units in the lesions measured, which is significantly more than would be expected by chance alone (two-sided p-value=0.004). However, there is no strong indication of a difference by dose level; for example, in a comparison of dose levels with respect to the proportion of lesions showing a decrease of at least 20%, the two-sided p-value was 0.43 (Wilcoxon rank-sum test with continuity correction).

TABLE 6

Proportion of Lesions in Each Patient Meeting with Decreases in Tumor Density

| Dose Level | Patient | Any Decrease | ≥10% Decrease | ≥15% Decrease | ≥20% Decrease |
|---|---|---|---|---|---|
| 1 | 1 | 3/5 (60%) | 3/5 (60%) | 2/5 (40%) | 1/5 (20%) |
| 1 | 2 | 4/5 (80%) | 2/5 (40%) | 2/5 (40%) | 2/5 (40%) |
| 1 | 3 | 5/5 (100%) | 4/5 (80%) | 3/5 (60%) | 2/5 (40%) |
| 2 | 4 | 1/2 (50%) | 1/2 (50%) | 1/2 (50%) | 1/2 (50%) |
| 2 | 5 | 3/5 (60%) | 3/5 (60%) | 3/5 (60%) | 1/5 (20%) |
| 2 | 6 | 2/3 (67%) | 2/3 (67%) | 0/3 (0%) | 0/3 (0%) |
| 2 | 7 | 5/5 (100%) | 5/5 (100%) | 5/5 (100%) | 5/5 (100%) |
| 2 | 8 | 4/5 (80%) | 4/5 (80%) | 4/5 (80%) | 4/5 (80%) |
| 2 | 9 | 4/5 (80%) | 4/5 (80%) | 4/5 (80%) | 3/5 (60%) |

Table 7 summarizes, by dose level, the proportion of patients meeting various criteria for tumor density reduction; for example, any decrease in density in at least 50% of lesions. Again, there is no clear evidence of a difference by dose level.

TABLE 7

Proportion of patients with effective treatment, by several criteria

| Criterion | Dose Level 1 | Dose Level 2 | All Patients |
|---|---|---|---|
| Any decrease in ≥50% of lesions | 3/3 (100%) | 6/6 (100%) | 9/9 (100%) |
| Any decrease in ≥60% of lesions | 3/3 (100%) | 5/6 (83%) | 8/9 (89%) |
| Any decrease in ≥75% of lesions | 2/3 (67%) | 3/6 (50%) | 5/9 (56%) |
| Any decrease in ≥80% of lesions | 2/3 (67%) | 3/6 (80%) | 5/9 (56%) |
| Decrease in 100% of lesions | 1/3 (33%) | 1/6 (17%) | 2/9 (22%) |
| ≥20% decrease in ≥1/3 of lesions | 2/3 (67%) | 4/6 (67%) | 6/9 (67%) |
| ≥20% decrease in ≥2/3 of lesions | 0/3 (0%) | 2/6 (33%) | 2/9 (22%) |

These data demonstrate significant decrease in tumor density of target lesions after Rexin-G treatment compared to baseline measurements indicating a reduction in the number of cancer cells and/or necrosis or cystic transformation within the tumor nodules, which meets the CHOI criteria of partial response (PR), thereby confirming the biologic activity of Rexin-G.

Patients in Dose Level 1 all had progressive disease leading to death with a median survival of 3½ months. In Dose Level 2 all patients had progressive disease leading to death with a median survival of 2½ months. In Dose Level 3 one patient died of progressive disease after surviving 4 months post-treatment with the two other patients still alive as of the last follow-up.

This study confirms the results achieved in initial clinical study A demonstrating the safety of Rexin-G at Dose Levels 1, 2, and 3. Further, the pharmacokinetics of the viral particles following intravenous infusions indicate rapid tumor targeting with little viral particles detectable in the blood 5 minutes post-administration. No induced immune responses to the viral particles were noted in a 6 week followup period indicating the low immunogenicity of the vector which will allow for repeat treatment cycles. No recombination events were found demonstrating the ability of a 3-plasmid transfection system to dramatically reduce the risk of such events. Also no vector integration in non-target organs was found. All 9 patients from Dose Levels 1 and 2 demonstrated decreased tumor density indicating biologic activity of Rexin-G, but no difference in tumor response between the two dose levels was noted.

Example 10

Case Study of Single Agent Rexin-G Efficacy in Metastatic Osteosarcoma

A 17 year old male diagnosed with osteosarcoma of the right tibia in December, 2003 underwent preoperative chemotherapy with cisplatin, adriamycin and high dose methotrexate followed by a limb salvage procedure. Histopathologic examination of the tumor showed only 50% necrosis in response to preoperative chemotherapy. Post-operatively, he received cisplatin and adriamycin×2, and adriamycin and ifosfamide×2, bringing the cumulative dose of adriamycin to 400 mg/m2. Chemotherapy was completed on February 2005. In March, 2006, follow-up CT scan showed two left sided pulmonary metastasis which was removed by VATS thorascopic surgery. A CT scan and PET scan showed persistent disease in the surgical area. From June to November, 2006, he received high dose methotrexate and ifosfamide, and then, underwent a thoracotomy in November, 2006. Repeat CT scan in December, 2006 showed progressive lung metastasis demonstrating failure of standard chemotherapy. Salvage therapy with taxotere, gemzar and adriamycin began in January, 2007, but sequential imaging demonstrated that his lung tumors grew in size and number from a single lung nodule measuring 1 cm to over 10 lung nodules, with the largest lesion measuring 4.2 cm by April, 2007.

After formal informed consent was obtained, the patient was enrolled in a Single Use Protocol of Rexin-G. Prior to the start of Rexin-G treatment, the cumulative vector dose was determined using the Calculus of Parity previously described by Gordon et al. (2006), by multiplying the estimated tumor burden (defined as the sum of the longest diameters of all lesions by 1×10e9 cancer cells) by an empiric targeting or physiologic coefficient of 100 (physiologic Multiplicity Of Infection, pMOI). The cumulative vector dose was determined to be 1.8×10e12 cfu Rexin-G vector and it was predicted that the patient would need 18-20 infusions of Rexin-G (at 1×10e11 cfu per dose) to halt disease progression and induce an objective tumor response.

A first treatment cycle of Rexin-G as 1×10e11 cfu administered intravenously twice a week for 4 weeks, followed by a 2 week rest period resulted in a cumulative dose of 8×10e11 cfu. Sequential PET-CT scans were taken before and after successive treatment cycles. (FIG. 30). A PET-CT scan obtained one week after completion of the first cycle showed a 28% increase in the sum size of the target lesions, a 6% decrease in the sum tumor density of target lesions, and a 33% reduction in the sum SUV max of 4 target lesions with 3 new small lung lesions noted. With few alternative therapeutic options and no observed toxicity to Rexin-G infusions, FDA approval was received for an additional treatment cycle of Rexin-G as 1×10e11 cfu administered intervenously twice a week for 4 weeks, bringing the cumulative dose to 1.6×10e12 cfu that approximated the predicted total dose of Rexin-G based on initial tumor burden. Remarkably, a PET-CT scan obtained 2 weeks after completion of the 2nd cycle showed no new lesions, a 539% increase in the sum tumor density indicating calcification of target lesions, and a 48% reduction in the sum SUV max of the 4 target lesions. (FIGS. 31-33) This was considered by the principal investigator as a positive partial response to the treatment, even though the sum tumor diameter increased.

Based on the positive tumor responses, a Phase II clinical trial for recurrent or metastatic chemotherapy refractive osteosarcoma was initiated. Since PET imaging is the most informative imaging modality for determining tumor response, and because RECIST criteria does not accurately reflect tumor response due to on-going reparative calcification of tumor nodules an exemption from the use of the standard RECIST criteria and its replacement with the International PET criteria is being sought from the FDA for monitoring and reporting tumor responses.

Example 11

Advanced Phase I/II Clinical Trials Using Adaptive Trial Design

Three advanced Phase I/II clinical trials with Adaptive trial design are on-going simultaneously in the United States for patients with recurrent or metastatic sarcoma, breast cancer or pancreatic cancer. The objectives of the studies are three-fold. 1) To determine the dose-limiting toxicity and maximum tolerated dose of Rexin-G administered as intravenous (IV) infusions. 2) To evaluate the potential of intravenous Rexin-G for evoking an immune response, recombination events and unwanted vector integration in non-target organs. 3) To identify an anti-tumor response to intravenously administered Rexin-G.

Each study will enroll a total of 15-24 patients. Table 8 shows the five planned dose levels with treatment already underway at Dose Level 0.

TABLE 8

Planned Dose Levels of Rexin-G

| Treatment Cycle* (4 weeks) | Dose Level | Vector Dose/Day | Max. Volume/Dose |
|---|---|---|---|
| Two times a week Starting Dose: | 0 | 1.0 × 10e11 cfu | 200 ml |
| Three times a week | I | 1.0 × 10e11 cfu | 200 ml |
| Three times a week | II | 2.0 × 10e11 cfu | 200 ml |
| Three time a week | III | 3.0 × 10e11 cfu | 200 ml |
| Three times a week | IV | 4.0 × 10e11 cfu | 200 ml |

*Each treatment cycle will be six weeks (four weeks of treatment and two weeks of rest). Patients who have resolution of toxicity to ≤ grade I may have repeat cycles.

Three patients on the sarcoma protocol have been treated at Dose Level 0 (1×10e11 cfu two times a week) and observed for 42 days without DLT. The Adaptive trial design allows patients to be retreated with the same treatment cycle if clinical efficacy is observed and all treatment related toxicities resolve to ≤Grade 1. Alternatively, patients may advance to the next higher Dose Level if there is resolution of toxicity to <grade 1. The Dose Level 0 sarcoma patients are currently being enrolled at Dose Level 1. This should increase the chances of gaining control of tumor growth and inducing an objective tumor response without compromising safety.

The Adaptive trial design also allows the principal investigator to recommend surgical debulking or surgical resection of residual tumor after the first treatment cycle has been completed. Treatment cycles may be resumed if residual tumor is detected in the histopath specimen or by PET-CT scan and the patient has Grade 1 or less toxicity.

For all three clinical trials, three patients will be enrolled at Dose Level I. If 1 of 3 patients at Dose Level I develops a grade 3 or 4 adverse event (CTCAE Version 3.0) which appears to be related or possibly related to Rexin-G, then 3 additional patients will be enrolled at the same dose level. If at least 2 of the first 3, or 3 of 6 patients at Dose Level I develop a grade 3 to 4 adverse event which appears to be related or possibly related to Rexin-G, accrual into the study will be held until the data are discussed with the Food and Drug Administration (FDA) and a decision is made whether to continue or terminate study enrollment. These dose limiting toxicity rules apply to all dose levels.

Dose escalation to the next dose level will not occur until 3 patients have been treated at the previous dose level and observed for forty-two days (6 weeks). There will be no intra-cohort dose escalation. At any dose level, up to six patients may be enrolled if there is evidence of biological activity in the first three patients. Dose escalation may stop if there is impressive evidence of biological activity. An amendment would be submitted to allow further expansion of dose level based on impressive biological activity.

Primary endpoints for the studies are clinical toxicity as evidenced by DLT and MTD defined by patient performance status, toxicity assessment score, hematologic, and metabolic profiles. Secondary endpoints are the potential of Rexin-G to evoke an immune response, recombination event, or unwanted vector integration in non-target organs.

Objective tumor response to Rexin-G are measured by RECIST, CHOI and PET Criteria. To date, 10 patients have been treated at the first dose level of 1×10e11 cfu twice a week for 4 weeks (sarcoma, n=6; breast cancer, n=1; and pancreatic cancer, n=3). Four-week evaluation of tumor responses are available for 4 patients and are listed in Table 9.

TABLE 9

Tumor Response in 4 Patients Treated with Dose Level 1 of Rexin-G

| Patient # | Disease | Response by RECIST | Response by PET | Response by CHOI |
|---|---|---|---|---|
| 1 | Sarcoma | Stable Disease | Stable Disease | Progressive Disease |
| 2 | Sarcoma | Stable Disease | Stable Disease | Stable Disease |
| 3 | Sarcoma | Progressive Disease | Stable Disease | Stable Disease |
| 4 | Pancreatic cancer | Stable Disease | Stable Disease | Stable Disease |

Table 9 shows that two of three patients in the sarcoma protocol and the one patient in the pancreatic cancer protocol have stable disease by RECIST, and four patients have stable disease by PET after 4 weeks of Rexin-G treatment. All 4 Rexin-G-treated patients had CT scan-documented tumor progression while on standard chemotherapy. These data show that Rexin-G has halted tumor progression in 3 of 4 (75%) patients by RECIST, 3 of 4 (75%) of patients by CHOI criteria, and 4 of 4 (100%) of patients by PET, indicating that PET scan imaging results may be used as early indicators of tumor response to Rexin-G treatment. In compliance with the FDA-approved Phase I/II protocols, 3 additional patients have been enrolled in the sarcoma protocol at the first dose level due to indications of biologic activity of Rexin-G at this dose level. Further, six patients in each of the sarcoma and pancreatic CA protocol will be enrolled at each dose level to evaluate a dose-response and to determine the optimal biologic dose and treatment schedule of Rexin-G for each clinical indication.

Example 12

Summary of Efficacy and Safety Data for 49 Patients Treated with Rexin-G

The accumulated clinical evidence demonstrates that Rexin-G has a unique safety profile compared to conventional chemotherapy. Objective tumor responses are noted (Table 10) without significant occurrence of adverse events or toxicity (Table 11).

TABLE 10

Summary of Administered Rexin-G Dose and Tumor Response

| Cumulative Dose | Partial Response | Stable Disease | Progressive Disease |
|---|---|---|---|
| <1 × $10^{11}$/week (n = 11) | 1/11 (9%) | 1/11 (9%) | 9/11 (82%) |
| 1 × $10^{11}$/week (n = 9) | 5/9 (56%) | 1/9 (11%) | 3/9 (33%) |
| 2 × $10^{11}$/week (n = 11) | 7/11 (64%) | 3/11 (27%) | 1/11 (9%) |
| 4 × $10^{11}$/week (n = 18) | 9/18 (50%) | 6/18 (33%) | 3/18 (16%) |

TABLE 11

Summary of Reported Side Effects

| | |
|---|---|
| Allergy/Immunology | Maculopapular rash, may or may not be itchy, generalized (4%) |
| Hematologic | Mild to moderate anemia requiring red cell transfusion due to bleeding into tumor seen with high dose Rexin-G administration (4%) |
| | Mild sporadic thrombocytopenia (2%) |
| Gastrointestinal | Abdominal pain, mild (2%) |
| | Abdominal distention, mild (2%) |
| | Anorexia, mild (2%) |
| | Constipation (16%), note: routine use of narcotics |
| Constitutional | Mild to moderate fever with or without chills while not being neutropenic (4%) |
| | Mild vague fatigue (24%) |
| Abnormal Chemistry | Mild elevated magnesium level (2%) |
| | Transient elevated AST and ALT lasting ≤72 hours (1%) |

Example 13

Phase II Clinical Study of Rexin-G in Patients with Chemotherapy Refractive Recurrent or Metastatic Osteosarcoma Twenty to thirty patients with chemotherapy refractory recurrent or metastatic osteosarcoma will be stratified into two different Rexin-G dose levels based on estimated tumor burden as calculated using the finding of PET-CT imaging studies. Estimated tumor burden is calculated by multiplying the sum of the longest diameters of target lesions in cm by 10e9 cancer cells. If the tumor burden is less than 10 billion cells, the patient will be assigned to Dose Level 1, if the tumor burden is greater than 10 billion cells, the patient will be assigned to Dose Level 2. Table 12.

TABLE 12

Dose Levels and Treatment Cycle for Rexin-G Treatment of Refractory Recurrent or Metastatic Osteosarcoma

| Treatment Cycle | Dose Level | Vector Dose/Day | Max. Volume/Dose |
|---|---|---|---|
| Two times a week | 1 | 1.0 × 10e11 cfu | 200 ml |
| Three times a week | 2 | 1.0 × 10e11 cfu | 200 ml |

The treatment cycle will be six weeks composed of four weeks of treatment followed by two weeks of rest. Patients who have resolution of toxicity to <grade I may have repeat cycles. PET-CT will be done every 6 weeks for the first four cycles, then every 12 weeks thereafter. After one or more treatment cycles, the principal investigator may recommend surgical debulking or complete surgical removal. If residual disease is present either by histopathological examination or by PET-CT scan, repeat treatment cycles may be given 4 weeks after surgery, if the surgical incision has healed, and if the patient has <grade I toxicity.

The objectives of the clinical study are to assess the clinical efficacy of intravenous (IV) Rexin-G and over-all safety. Clinical efficacy includes tumor response rates, progression-free survival and over-all survival. International PET criteria will be used to assess tumor response rates as CR, PR or SD. Progression-free survival is survival greater than one month and over-all being defined as survival of 6 months or longer. Over-all safety of intravenously administered Rexin-G will be measured by performance status, toxicity assessment score, hematologic, metabolic profiles, immune responses, vector integration in PBLs and recombination events.

Example 14

Case Study of a Patient with Advanced Metastatic Pancreatic C Treated with Rexin-G Followed by Reximmune-C When radiation and chemotherapy fail to control the spread of metastatic pancreatic cancer to and in the liver, the tumor burden within this vital organ can grow to enormous proportions, displacing normal liver parenchyma with massive tumor formations. At such times, compassionate use and informed consent combine to encourage the application of more aggressive protocols to reduce the lethal tumor burden. FIG. 34 shows a series of sections showing extensive necrosis of the primary tumor in an autopsied tumor specimen obtained from a patient with intractable metastatic pancreatic cancer that was treated with successive infusions of Rexin-G for 28 days (Cumulative Dose: 2×10e12 cfu) followed by Reximmune-C for 6 days (Cumulative Dose: 3×10e10 cfu). While the series of infusions were well-tolerated, and the overall tumor burden was reduced significantly, the patient failed to thrive and to readily resolve the large lesions, necessitating supportive care. Unfortunately, the patient died of a fulminant *Escherichia coli* bacterial sepsis three months after treatment, which was considered to be unrelated to the Rexin-G intervention, yet may relate to the problem of post-ablative wound healing in a more general sense. However, histological examination of the extent of the tumor destruction is informative. As seen in Panel A of FIG. 34, and enlarged in Panels B & C, post-mortem findings indicate a massive amount of necrosis (n) involving ~95% of this pancreatic tumor with various areas of fibrosis (f), flanked by degenerative (deg) and organoid structures. Immunohistochemical staining for GM-CSF identified several areas where tumor cells expressing GM-CSF (Panels E & F) were evident (arrows) in small islands (boxed area, enlarged in E), and significant immune infiltrate (im) is seen in the vicinity of what appears to be necrotic fragments of GM-CSF secreting cells (Panel F). This clinical case study highlights three important issues: (i) the overall importance of treating patients earlier, before cancer produces irreparable organ damage, (ii) the potential for Rexin-G to meet and match extremely large tumor burdens, and (iii) the potential for Reximmune-C, with its immune-stimulating payload, to participate in the process of tumor destruction.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor. N.Y., 1986).

What is claimed is:

1. A method of inhibiting tumor metastasis in a human patient having a tumor that has metastasized, said method comprising:

intravenously administering to the patient a therapeutically effective amount of retroviral particles at a cumulative dose of at least $1.8\times10^{11}$ colony forming units (cfu), wherein each of the retroviral particles comprises:

i) a modified retroviral envelope protein wherein the retroviral envelope protein includes a receptor binding region which has been modified to contain a collagen binding domain comprising the amino acid sequence Gly-His-Val-Gly-Trp-Arg-Glu-Pro-Ser-Phe-Met-Ala-Leu-Ser-Ala-Ala (SEQ ID NO:1), and ii) encodes a heterologous therapeutic polypeptide, wherein the heterologous therapeutic polypeptide is a suicide protein chosen from the group consisting of thymidine kinase, cytosine deaminase, p450 oxidoreductase, carboxypeptidase G2, beta-glucoronidase, penicillin-V-amidase, penicillin-G-amidase, beta-lactamase, nitroreductase, carboxypeptidase A, linarmarase, *E. coli* gpt gene product, and *E. coli* Deo gene product.

2. The method of claim 1, wherein the thymidine kinase is from herpes simplex virus or varicella zoster virus.

3. The method of claim 1, wherein the retroviral particles accumulate in the patient in areas of exposed collagen.

4. The method of claim 1, wherein the areas of exposed collagen include neoplastic lesions, areas of active angiogenesis, metastatic tumor invasion lesions, cancerous lesions, areas of vascular injury, surgical sites, inflammatory sites or areas of tissue destruction.

5. The method of claim 1, wherein the retroviral envelope protein is a modified 4070A amphotropic envelope protein.

6. The method of claim 1, wherein the receptor binding region is modified by inserting a peptide containing a collagen binding domain between two consecutively numbered amino acid residues of the native gp70 portion of the 4070A amphotropic envelope protein.

7. The method of claim 6, wherein the peptide is inserted between amino acids 6 and 7 of the native gp70 portion of the 4070A amphotropic envelope protein.

* * * * *

SEQUENCE LISTING

```
<160> NUMBER OF SEQ ID NOS: 11

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly His Val Gly Trp Arg Glu Pro Ser Phe Met Ala Leu Ser Ala Ala
1               5                   10                  15

<210> SEQ ID NO 2
<211> LENGTH: 770
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 2

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca tagggactt tccattgacg tcaatgggtg gagtatttac ggtaaactgc     360
ccacttggca gtacatcaag tgtatcatat gccaagtccg cccctattg acgtcaatga     420
cggtaaatgg cccgcctggc attatgccca gtacatgacc ttcgggact ttcctacttg     480
gcagtacatc tacgtattag tcatcgctat taccatggta tgcggtttt ggcagtacac     540
caatgggcgt ggatagcggt ttgactcacg ggatttcca agtctccacc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt             770
```

<210> SEQ ID NO 3
<211> LENGTH: 770
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
accgcaataa agcttctagt gatctgacgg ttcactaaac gagctctgct tatatagacc      60
tcccaccgta cacgcctacc gcccatttgc gtcaacgggg cggcgatcg cagttgttac     120
gacattttgg aaagtcccgt tgattttggt gccaaaacaa actcccattg acgtcaatgg     180
ggtggagact tggaaatccc cgtgagtcaa accgctatcc acgccattg gtgtactgcc     240
aaaaccgcat caccatggta atagcgatga ctaatacgta gatgtactgc caagtaggaa     300
agtcccgtaa ggtcatgtac tgggcataat gccaggcggg ccatttaccg tcattgacgt     360
caatagggg cggacttggc atatgataca cttgatgtac tgccaagtgg gcagtttacc     420
gtaaatactc cacccattga cgtcaatgga aagtccctat ggcgttact atgggaacat     480
acgtcattat tgacgtcaat gggcgggggt cgttgggcgg tcagccaggc gggccattta     540
ccgtaagtta tgtaacgcgg aactccatat atgggctatg aactaatgac cccgtaattg     600
attactatta ataactagtc aataatcaat gccaacatgg cggtcatatt ggacatgagc     660
caatataaat gtacatatta tgatatagat acaacgtatg caatggccaa tagccaatat     720
tgatttatgc tatataacca atgaataata tggctaatgg ccaatattga             770
```

<210> SEQ ID NO 4
<211> LENGTH: 10
<212> TYPE: PRT
<213> ORGANISM: Homo sapiens

<400> SEQUENCE: 4

Trp Arg Glu Pro Ser Phe Met Ala Leu Ser
1              5                    10

<210> SEQ ID NO 5
<211> LENGTH: 6
<212> TYPE: PRT
<213> ORGANISM: Moloney murine leukemia virus

<400> SEQUENCE: 5

Gly Gly Trp Ser His Trp
1               5

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggacatgtag gatggagaga accatcattc atggctctgt cagctgca                48

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgcggccgc ccaccatggc gcgttcaacg ctctcaaaac cccctcaaga ta            52

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctctagatt atcatggctc gtactctatg ggttttagct gg                      42

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly His Val Gly Trp Arg Glu Pro Ser Phe Met Ala Lys Ser Ala Ala
1               5                   10                  15

<210> SEQ ID NO 10
<211> LENGTH: 97
<212> TYPE: DNA
<213> ORGANISM: Moloney murine leukemia virus

<400> SEQUENCE: 10
cccccgcccc ttgtaaactt ccctgaccct gacatgacaa gagttactaa cagcccctct   60
ctccaagctc acttacaggc tctctactta gtccagc                            97

<210> SEQ ID NO 11
<211> LENGTH: 96
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 11
cccccgcccc ttgtaaactt ccctgaccct gacatgcaag agttactaac agcccctctc     60
tccaagctca cttacaggct ctctacttag tccagc                               96
```